United States Patent [19]
Sakamoto et al.

[11] Patent Number: 6,159,904
[45] Date of Patent: *Dec. 12, 2000

[54] PYRAZOLE DERIVATIVES

[75] Inventors: Masashi Sakamoto; Hideki Kamano; Hiroshi Yamamoto; Hidetsugu Ikeda, all of Sodegaura, Japan

[73] Assignee: Idemitsu Kosan Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/276,740

[22] Filed: Mar. 26, 1999

Related U.S. Application Data

[63] Continuation of application No. 09/043,917, filed as application No. PCT/JP96/02879, Oct. 3, 1996, abandoned.

[30] Foreign Application Priority Data

Oct. 4, 1995 [JP] Japan ................................. 7-257973
Dec. 11, 1995 [JP] Japan ................................. 7-322030

[51] Int. Cl.[7] ....................... A01N 43/56; C07D 409/06; C07D 335/06
[52] U.S. Cl. .......................... 504/282; 549/23; 548/364.4
[58] Field of Search .................... 549/23; 504/282

[56] References Cited

U.S. PATENT DOCUMENTS

| | | | |
|---|---|---|---|
| 5,468,722 | 11/1995 | Shibata et al. | 504/282 |
| 5,480,858 | 1/1996 | Sakamoto et al. | 504/288 |
| 5,506,194 | 4/1996 | Nasuno et al. | 504/282 |
| 5,587,484 | 12/1996 | Shibata et al. | 549/23 X |
| 5,591,868 | 1/1997 | Nasuno et al. | 549/23 |
| 5,607,898 | 3/1997 | Nakamura et al. | 504/282 |
| 5,756,759 | 5/1998 | Shibata et al. | 504/282 X |
| 5,801,121 | 9/1998 | Kamano et al. | 504/288 |

FOREIGN PATENT DOCUMENTS

| | | |
|---|---|---|
| 3-505204 | 11/1991 | Japan . |
| 93/18031 | 3/1993 | WIPO . |
| 94/04524 | 3/1994 | WIPO . |
| 95/13275 | 5/1995 | WIPO . |
| 96/25412 | 8/1996 | WIPO . |
| 96/25413 | 8/1996 | WIPO . |

*Primary Examiner*—Fiona T. Powers
*Attorney, Agent, or Firm*—Oblon, Spivak, McClelland, Maier & Neustadt, P.C.

[57] ABSTRACT

Pyrazole derivatives of the general formula (I) or salts thereof,

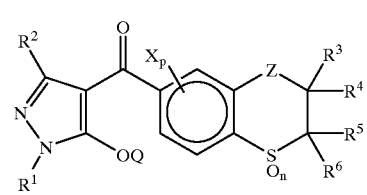

(I)

wherein each symbols are as defined in the specification, herbicides containing the above compounds as active ingredients, and aromatic carboxylic acid derivatives or salts thereof suitable as intermediates for the production of the above pyrazole derivatives.

The above pyrazole derivatives or salts thereof, provided by the present invention, cause no phytotoxicity on upland field crops such as corn, etc., and can selectively control a broad range of upland weeds such as grass weeds and broad-leaved weeds at a low dosage in pre-emergence treatment and in post-emergence treatment.

19 Claims, No Drawings

PYRAZOLE DERIVATIVES

This application is a Continuation of application Ser. No. 09/043,917, filed on May 19, 1998, now abandoned, which was originally filed as International Application No. PCT/JP96/02879, filed on Oct. 3, 1996.

TECHNICAL FIELD

The present invention relates to novel pyrazole derivatives, herbicides containing them, and aromatic carboxylic acid derivatives. More specifically, it relates to a pyrazole derivative which can control a broad range of weeds at a low dosage without causing phytotoxicity on field crops such as a corn, a herbicide containing the pyrazole derivative as an active ingredient, and an aromatic carboxylic acid derivative useful as an intermediate for the production of the pyrazole derivative.

TECHNICAL BACKGROUND

During a planting time of corn, etc., a triazine-based herbicide such as atrazine and acid anilide-based herbicides such as alachlor and metolachlor have been mainly used. However, these herbicides are causing environmental problems such as the pollution of ground water, etc., due to their high dosage requirement.

Further, it is a known fact that when herbicides of specific series are used for a long period of time, some weeds begin to exhibit resistance to the herbicides. Those weeds which are difficult to control, including the above resistant weeds, are becoming non-negligible. In view of this fact, herbicidal compounds having a novel skeleton and herbicidal compositions containing these compounds are still highly demanded.

Pyrazole-containing herbicides which can replace the above triazine-based herbicides and the above acid anilide-based herbicides are known, and those of the following formulae are commercially available.

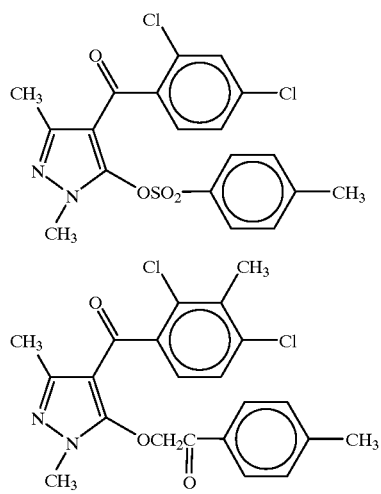

However, the above compounds are both used as herbicides for paddy rice, and have been used during a planting time of field crops such as corn in no case.

International Laid-open Patent Publication No. WO93/18031 discloses a herbicidally active pyrazole derivative having a thiochroman ring. The typical compounds (A) and (B) thereof have structures as shown below.

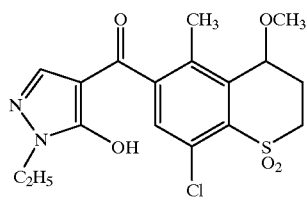
(A)

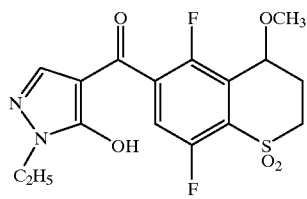
(B)

The above compounds (A) and (B) exhibit good herbicidal efficacy both in post-emergence treatment. Especially compound (A) exhibits an excellent herbicidal efficacy on broad-leaved weeds in post-emergence treatment, while it shows insufficient efficacy on grass weeds. Further, compounds (A) and (B) show somewhat insufficient efficacy when used in pre-emergence treatment.

Further, International Laid-open Patent Publication No. WO95/04054 discloses herbicidally active pyrazole derivatives having a thiochroman ring, represented by the following general formula.

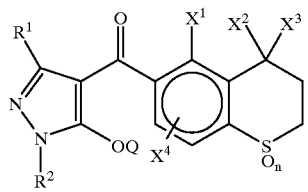

wherein each of $X^2$ and $X^3$ is a $C_1$~$C_4$ alkyl group. The explanation of the other symbols is omitted.

The structures of the typical compounds (C) and (D) in the above International Laid-open Patent Publication are as shown below.

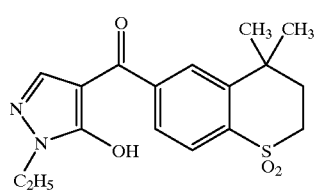
(C)

-continued

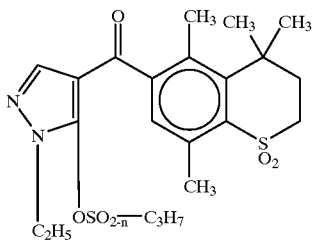

(D)

The above compound (D) exhibits sufficient herbicidal efficacy against several kinds of broad-leaved and grass weeds even when the treatment is carried out at an effective dose of as low as 100 g per hectare, while there are some weeds, some grass weeds in particular, against which its efficacy is insufficient when it is applied to a broader range of weeds.

DISCLOSURE OF THE INVENTION

Under the above circumstances, it is the first object of the present invention to provide a novel pyrazole derivative which can control wide-ranging kinds of weeds which occur at the time of planting field crops such as corn, etc., simultaneously at a low dosage without causing phytotoxicity on these crops.

It is the second object of the present invention to provide a herbicide containing the above novel pyrazole derivative as an active ingredient.

Further, it is the third object of the present invention to provide an intermediate for the production of the above pyrazole derivative.

The present inventors have made diligent studies, and as a result, have found that specifically structured pyrazole derivatives having a thiochroman ring can control wide-ranging kinds of weeds at a low dosage and show safety to crops such as corn, etc., and that specifically structured aromatic carboxylic acid derivatives are suitable as an intermediate for the production of the above pyrazole derivatives. On the basis of the above findings, the present invention has been arrived at.

That is, the first object of the present invention is achieved by pyrazole derivatives of the following general formula (I) or salts thereof (to be sometimes referred to as "pyrazole derivative of the present invention" hereinafter).

General Formula (I)

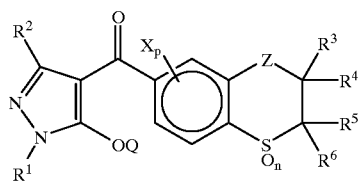

(I)

wherein $R^1$ is a $C_1$~$C_4$ alkyl group, a $C_2$~$C_4$ alkenyl group or a $C_2$~$C_4$ haloalkenyl group, $R^2$ is a hydrogen atom, a $C_1$~$C_4$ alkyl group, a $C_1$~$C_4$ haloalkyl group or a $C_2$~$C_4$ alkoxyalkyl group, X is a $C_1$~$C_4$ alkyl group, a $C_1$~$C_4$ haloalkyl group, $C_2$~$C_4$ alkoxyalkyl group, a halogen atom, a $C_1$~$C_4$ alkoxy group or a $C_1$~$C_4$ haloalkoxy group, p is an integer of 0, 1, or 2, each of $R^3$, $R^4$, $R^5$ and $R^6$ is independently a hydrogen atom, a $C_1$~$C_4$ alkyl group, a $C_1$~$C_4$ haloalkyl group, a $C_2$~$C_4$ alkoxyalkyl group or a halogen atom, or $R^3$ or $R^4$ may form a bonding with $R^5$ or $R^6$, n is an integer of 0, 1 or 2, Q is a hydrogen atom or a group of -A-B in which A is

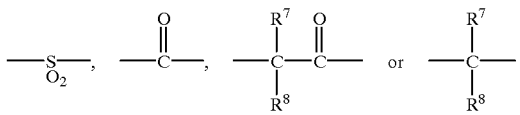

in which each of $R^7$ and $R^8$ is independently a hydrogen atom or a $C_1$~$C_4$ alkyl group, and B is a $C_1$~$C_{12}$ alkyl group, a $C_3$~$C_{10}$ cycloalkyl group or

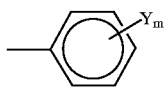

in which Y is a $C_1$~$C_4$ alkyl group, a $C_1$~$C_4$ alkoxy group, a $C_1$~$C_4$ haloalkyl group, a nitro group or a halogen atom, and m is an integer of 0 to 3, and Z is a group of the following (a), (b) or (c),

(a)

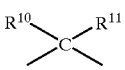

(b)

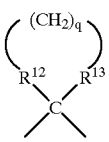

(c)

in which $R^9$ in the formula (a) is an oxygen atom or a sulfur atom, $R^{10}$ in the formula (b) is a halogen atom, a $C_1$~$C_4$ alkoxy group, a $C_1$~$C_4$ alkylthio group, a $C_2$~$C_6$ alkoxyalkyl group or any group of the following formulae,

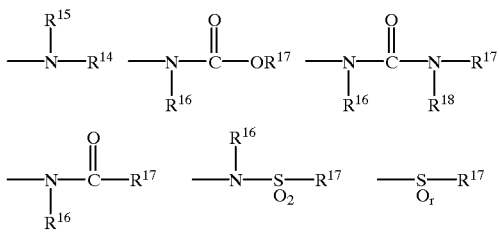

-continued

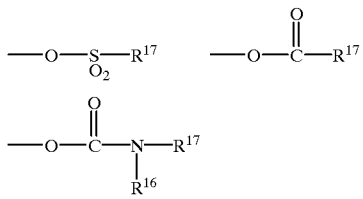

in which each of $R^{14}$ and $R^{15}$ is independently a hydrogen atom, an oxygen atom or a $C_1~C_4$ alkyl group, $R^{16}$ is a hydrogen atom or a $C_1~C_4$ alkyl group, each of $R^{17}$ and $R^{18}$ is independently a $C_1~C_4$ alkyl group or a $C_1~C_4$ haloalkyl group, and r is an integer of 0, 1 or 2, $R^{11}$ is a hydrogen atom, a $C_1~C_4$ alkyl group, a $C_1~C_4$ alkoxy group or a $C_1~C_4$ alkylthio group, or $R^{11}$ may form a bonding with $R^3$, provided that in no case $R^{10}$ is a $C_1~C_4$ alkoxy group and $R^{11}$ is a hydrogen atom, q in the formula (c) is an integer of 2 to 4, and each of $R^{12}$ and $R^{13}$ is independently an oxygen atom, a sulfur atom or —$CH_2$—.

The second object of the present invention is achieved by a herbicide containing, as an active ingredient, at least one selected from the pyrazole derivatives of the above general formula (I) and salts thereof (to be sometimes referred to as "herbicide of the present invention" hereinafter).

Further, the third object of the present invention is achieved by aromatic carboxylic acid derivatives of the following general formula (II) or salts thereof (to be sometimes referred to as "intermediate of the present invention" hereinafter).

General Formula (II)

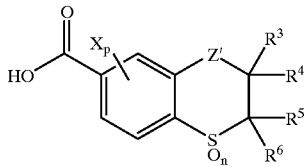

wherein:

X is a $C_1~C_4$ alkyl group, a $C_1~C_4$ haloalkyl group, a $C_2~C_4$ alkoxyalkyl group, a halogen atom, a $C_1~C_4$ alkoxy group or a $C_1~C_4$ haloalkoxy group, p is an integer of 0, 1 or 2, each of $R^3$, $R^4$, $R^5$ and $R^6$ is independently a hydrogen atom, a $C_1~C_4$ alkyl group, a $C_1~C_4$ haloalkyl group, a $C_2~C_4$ alkoxyalkyl group or a halogen atom, or $R^3$ or $R^4$ may form a bonding with $R^5$ or $R^6$, n is an integer of 0, 1 or 2, and Z' is a group of the following (a), (b') or (c),

 (a)

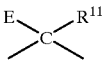 (b')

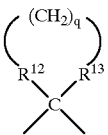 (c)

in which $R^9$ in the formula (a) is an oxygen atom or a sulfur atom, $R^{11}$ in the formula (b') is a hydrogen atom, a $C_1~C_4$ alkyl group, a $C_1~C_4$ alkoxy group or a $C_1~C_4$ alkylthio group, or $R^{11}$ may form a bonding with $R^3$, E is a hydroxyl group, a halogen atom, a $C_1~C_4$ alkoxy group, a $C_1~C_4$ alkylthio group, a $C_2~C_6$ alkoxyalkyl group or any group of the following formulae,

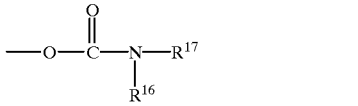

in which each of $R^{14}$ and $R^{15}$ is independently a hydrogen atom, an oxygen atom or a $C_1~C_4$ alkyl group, $R^{16}$ is a hydrogen atom or a $C_1~C_4$ alkyl group, each of $R^{17}$ and $R^{18}$ is independently a $C_1~C_4$ alkyl group or a $C_1~C_4$ haloalkyl group, and r is an integer of 0, 1 or 2, provided that when $R^{11}$ and $R^3$ do not form a bonding, E may form a bonding with $R^3$ and that in no case E is a $C_1~C_4$ alkoxy group and $R^{11}$ is a hydrogen atom, q in the formula (c) is an integer of 2 to 4, and each of $R^{12}$ and $R^{13}$ is independently an oxygen atom, a sulfur atom or —$CH_2$—, provided that the compound is excluded in which in the general formula (II), p is 0, Z' is carbonyl group (in above (a), $R^9$=oxygen atom), n is 0 and all of $R^3$, $R^4$, $R^5$ and $R^6$ are hydrogen atoms,

PREFERRED EMBODIMENTS OF THE INVENTION

The pyrazole derivative of the present invention will be explained first.

The pyrazole derivative of the present invention is a compound of the general formula (I).

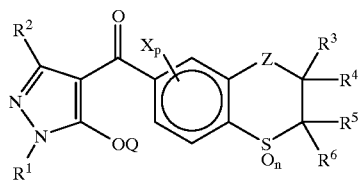

(I)

In the general formula (I), $R^1$ is a $C_1 \sim C_4$ alkyl group, a $C_2 \sim C_4$ alkenyl group or a $C_2 \sim C_4$ haloalkenyl group. Specific examples of the $C_1 \sim C_4$ alkyl group include methyl, ethyl, propyl and butyl. The propyl and the butyl may be linear, cyclic or branched. Specific examples of the $C_2 \sim C_4$ alkenyl group include vinyl, allyl, propen-1-yl, propen-2-yl, n-1-buten-1-yl, n-1-buten-2-yl, n-1-buten-3-yl, n-1-buten-4-yl, n-2-buten-1-yl, n-2-buten-2-yl, i-buten-1-yl and i-buten-3-yl. The $C_2 \sim C_4$ haloalkenyl group refers to a substituent formed by replacing 1 to 7 hydrogen atoms of the above $C_2 \sim C_4$ alkenyl group with halogen atom(s) (e.g., chlorine, fluorine, bromine or iodine).

$R^1$ is preferably a $C_1 \sim C_4$ alkyl group, more preferably methyl or ethyl, particularly preferably ethyl.

In the general formula (I), $R^2$ is a hydrogen atom, a $C_1 \sim C_4$ alkyl group, a $C_1 \sim C_4$ haloalkyl group or a $C_2 \sim C_4$ alkoxyalkyl group. Specific examples of the $C_1 \sim C_4$ alkyl group include those specified concerning $R^1$. The $C_1 \sim C_4$ haloalkyl group refers to a substituent formed by replacing 1 to 9 hydrogen atoms of the above $C_1 \sim C_4$ alkyl group with halogen atom(s) (e.g., chlorine, fluorine, bromine or iodine). Specific examples thereof include —$CF_3$, —$C_2F_5$, —$C_2H_4F$, —$CH_2Cl$, —$CHF_2$, —$CCl_3$, —$C_2H_3Cl_2$, —$C_2H_3F_2$, —$C_2H_2F_3$, —$C_2H_2Cl_3$, —$C_3H_6F$, —$C_4H_8F$, —$CH_2Br$, —$CH_2I$, —$C_3H_4F_3$ and —$C_4H_6F_3$. The $C_2 \sim C_4$ alkoxyalkyl group refers to a substituent formed by replacing one hydrogen atom of the above alkyl group with a $C_1 \sim C_3$ alkoxy group (any one of methoxy, ethoxy, n-propyloxy and i-propyloxy). Specific examples thereof include —$CH_2$—$OCH_3$, —$CH_2$—$OC_2H_5$, —$CH_2$—$OC_3H_7$, —$CH(CH_3)$$OCH_3$, —$CH(CH_3)OC_2H_5$, —$CH_2CH_2OCH_3$, —$CH_2CH_2OC_2H_5$, —$C(CH_3)_2OCH_3$, —$CH_2CH(CH_3)$$OCH_3$ and —$CH_2$—$CH_2$—$CH_2$—$OCH_3$.

$R^2$ is preferably a hydrogen atom or a $C_1 \sim C_4$ alkyl group such as methyl, particularly preferably a hydrogen atom.

In the general formula (I), X is a $C_1 \sim C_4$ alkyl group, a $C_1 \sim C_4$ haloalkyl group, a $C_2 \sim C_4$ alkoxyalkyl group, a halogen atom, a $C_1 \sim C_4$ alkoxy group or a $C_1 \sim C_4$ haloalkoxy group. Specific examples of the $C_1 \sim C_4$ alkyl group, the $C_1 \sim C_4$ haloalkyl group and the $C_2 \sim C_4$ alkoxyalkyl group include those specified concerning $R^2$. Specific examples of the halogen atom include chlorine, fluorine, bromine and iodine. Specific examples of the $C_1 \sim C_4$ alkoxy group include methoxy, ethoxy, propoxy and butoxy. The propoxy and the butoxy may be linear, cyclic or branched. The $C_1 \sim C_4$ haloalkoxy group refers to a substituent formed by replacing 1 to 9 hydrogen atoms with halogen atom(s) (e.g., chlorine, fluorine, bromine or iodine). Examples thereof include —$OCF_3$, —$OC_2F_5$, —$OC_2H_4F$, —$OC_2H_4Cl$, —$OCHF_2$, —$OCH_2F$, —$OCCl_3$, —$OC_2H_3Cl_2$, —$OC_2H_3F_2$, —$OCH_2Br$ and —$OCH_2I$.

X is preferably a $C_1 \sim C_4$ alkyl group, $C_1 \sim C_4$ alkoxy group or a halogen atom, particularly preferably methyl, methoxy or chlorine.

In the general formula (I), p is the number of substituents X, and it is an integer of 0, 1 or 2, preferably 1 or 2. When p is 1 or 2, the position on which X is substituted is at least one of the 5-position, the 7-position and the 8-position on the thiochroman ring. When p is 1, X is preferably substituted on the 5-position. When p is 2, the substituents X are preferably substituted on the 5- and 8-positions.

In the general formula (I), each of $R^3$, $R^4$, $R^5$ and $R^6$ is independently a hydrogen atom, a $C_1 \sim C_4$ alkyl group, a $C_1 \sim C_4$ haloalkyl group, a $C_2 \sim C_4$ alkoxyalkyl group or a halogen atom. Specific examples of the $C_1 \sim C_4$ alkyl group, the $C_1 \sim C_4$ haloalkyl group and the $C_2 \sim C_4$ alkoxyalkyl group include those specified concerning $R^1$ or $R^2$. Specific examples of the halogen atom includes those specified concerning X.

Each of $R^3$, $R^4$, $R^5$ and $R^6$ is independently preferably a hydrogen atom or a $C_1 \sim C_4$ alkyl group such as methyl. Particularly preferably , each of $R^5$ and $R^6$ is a hydrogen atom. Further, $R^3$ or $R^4$ may form a bonding with $R^5$ or $R^6$.

In the general formula (I), n is the number of oxygen atoms bonding to the sulfur atom of the thiochroman ring, and it is an integer of 0 (sulfide), 1 (sulfoxide) or 2 (sulfone), preferably 0 (sulfide) or 2 (sulfone).

In the general formula (I), Q is a group of -A-B.

In Q, A is a group of

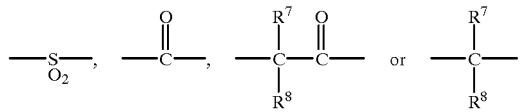

in which each of $R^7$ and $R^8$ is independently a hydrogen atom or a $C_1 \sim C_4$ alkyl group.

Specific examples of the $C_1 \sim C_4$ alkyl group include those specified concerning $R^1$. Preferably, each of $R^7$ and $R^8$ is a hydrogen atom.

In Q, B is a $C_1 \sim C_{12}$ alkyl group, a $C_3 \sim C_{10}$ cycloalkyl group or a group of

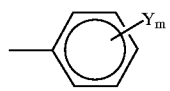

Specific examples of the $C_1 \sim C_{12}$ alkyl group include pentyl, hexyl, heptyl, octyl, nonyl, decyl, undecyl and dodecyl in addition to those of the $C_1 \sim C_4$ alkyl group specified concerning $R^1$. The alkyl group having at least 3 carbon atoms may be linear, cyclic or branched. The $C_1 \sim C_{12}$ alkyl group is preferably a $C_1 \sim C_8$ alkyl group. Specific examples of the $C_3 \sim C_{10}$ cycloalkyl group include cyclopropyl, cyclobutyl, cyclopentyl, cyclohexyl, cycloheptyl, cyclooctyl, cyclononyl and cyclodecyl. The number of carbon atoms of the cycloalkyl group is 3 to 10 as described above, and 1 or more $C_1$~$C_4$ alkyl groups may be substituted on the ring of the cycloalkyl group so long as the total number of carbon atoms is within the above range.

In the group of

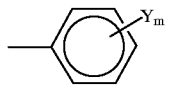

which is one definition of B, Y is a $C_{1\sim C4}$ alkyl group, a $C_1$~$C_4$ alkoxy group, a $C_1$~$C_4$ haloalkyl group, a nitro group or a halogen atom. Specific examples of the $C_1$~$C_4$ alkyl group, the $C_1$~$C_4$ alkoxy group, the $C_1$~$C_4$ haloalkyl group and the halogen atom include those specified concerning $R^2$ or X. The $C_1$~$C_4$ alkyl group is preferably methyl. The $C_1$~$C_4$ alkoxy group is preferably methoxy. The halogen atom is preferably chlorine or fluorine.

m is the number of substituents(s) Y, and it is an integer of 0 to 3, preferably 0 or 1, particularly preferably 1. Y may be substituted on any of the 2- to 6-positions on the phenyl group, while the position for its substitution is preferably 2-position (o-position) or 4-position (p-position).

Preferably, B is ethyl, n-propyl, phenyl, 2-methylphenyl or 4-methylphenyl.

Preferably, Q is a hydrogen atom, or when Q is a group of -A-B, Q is a combination of A which is —$SO_2$— and B which is ethyl, n-propyl, 2-methylphenyl or 4-methylphenyl.

Z is a group of the following (a), (b) or (c).

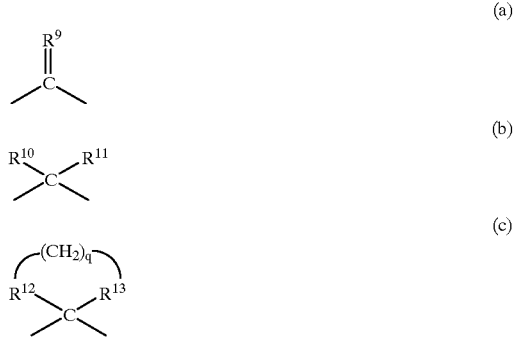

In the formula (a) in the definition of Z, $R^9$ is an oxygen or sulfur atom, preferably an oxygen atom.

In the formula (b) in the definition of Z, $R^{10}$ is a halogen atom, a $C_1$~$C_4$ alkoxy group, a $c_1$~$C_4$ alkylthio group, a $C_2$-$C_6$ alkoxyalkyl group or any group of the following formulae.

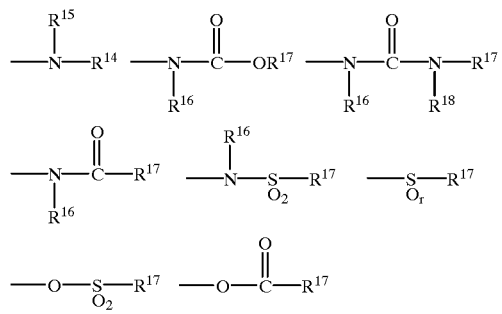

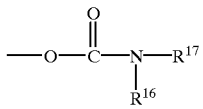

In the above formulae, each of $R^{14}$ and $R^{15}$ is independently a hydrogen atom, an oxygen atom or a $C_1$~$C_4$ alkyl group, $R^{16}$ is a hydrogen atom or a $C_1$~$C_4$ alkyl group, each of $R^{17}$ and $R^{18}$ is independently a $C_1$~$C_4$ alkyl group or a $C_1$~$C_4$ haloalkyl group, and r is an integer of 1 or 2.

$R^{11}$ is a hydrogen atom, a $C_1$~$C_4$ alkyl group, a $C_1$~$C_4$ alkoxy group or a $C_1$~$C_4$ alkylthio group, or $R^{11}$ may form a bonding with $R^3$, provided that in no case $R^{10}$ is a $C_1$~$C_4$ alkoxy group and $R^{11}$ is a hydrogen atom.

When $R^{10}$ is a halogen atom, specific examples of the halogen atom include fluorine, chlorine, bromine and iodine. When $R^{10}$ is a substituent containing $R^{14}$ and $R^{15}$, specific examples thereof include amino; nitro; a monoalkylamino group such as methylamino, ethylamino and propylamino; and dialkylamino groups such as dimethylamino, diethylamino, di-n-propylamino, di-n-butylamino, methylethylamino, methyl-n-propylamino and methyl-n-butylamino. Specific examples of the other substituents containing at least one of $R^{16}$ to $R^{18}$ include carbonylamino groups such as N-methyl-N-methoxycarbonylamino and N-methyl-N-(N',N'-dimethylaminocarbonyl)amino; alkanoylamino groups such as N-methyl-N-acetylamino; alkanesulfonylamino groups such as N-methyl-N-methanesulfonylamino; alkylsulfinyl groups such as methylsulfinyl, ethylsulfinyl, propylsulfinyl and butylsulfinyl; alkanesulfonyl groups such as methanesulfonyl, ethanesulfonyl, propanesulfonyl and butanesulfonyl; sulfonyloxy groups such as methanesulfonyloxy, trifluoromethanesulfonyloxy, ethanesulfonyloxy, propanesulfonyloxy and butanesulfonyloxy; acetoxy groups such as acetoxy, trifluoroacetoxy and trichloroacetoxy; alkanoyloxy groups such as propionyloxy and butyloyloxy; and carbamoyloxy groups such as N-methylcarbamoyloxy and N,N-dimethylcarbamoyloxy.

The $C_2$~$C_6$ alkoxyalkyl group which is one definition of $R^{10}$ refers, for example, to a substituent formed by replacing one hydrogen atom of an alkyl group with an alkoxy group such as methoxy, ethoxy, n-propoxy or i-propoxy. When the alkyl portion of the alkoxyalkyl group has at least 3 carbon atoms, the alkyl portion may be linear, cyclic or branched. Specific examples of the alkoxyalkyl group include —$CH_2OCH_3$, —$CH_2OC_2H_5$, —$CH_2OC_3H_7$, —$CH_2OC_4H_9$, —$CH(CH_3)OCH_3$, —$CH(CH_3)OC_2H_5$, —$CH_2CH_2OCH_3$, —$CH_2CH_2OC_2H_5$, —$C(CH_3)_2OCH_3$, and —$CH_2CH(CH_3)OCH_3$, —$(CH_2)_3$—O—$CH_3$, and —$(CH_2)_4$—$OCH_3$.

When $R^{10}$ and $R^{11}$ are $C_1$~$C_4$ alkoxy groups, examples of the alkoxy groups include methoxy, ethoxy, propoxy and butoxy. When $R^{10}$ and $R^{11}$ are $C_1$~$C_4$ alkylthio groups, examples of the alkylthio groups include methylthio, ethylthio, propylthio and butylthio. When $R^{11}$ is a $C_1$~$C_4$ alkyl group, examples the alkyl group include methyl, ethyl, propyl and butyl. When the alkyl portion of each of these groups has at least 3 carbon atoms, the alkyl portion may be linear, cyclic or branched.

In the group (c) in the definition of Z, each of $R^{12}$ and $R^{13}$ is independently an oxygen atom, a sulfur atom or —$CH_2$—. q is the number of a methylene chain, and it is 2, 3 or 4, preferably 2. Preferably, both $R^{12}$ and $R^{13}$ are both oxygen atoms or sulfur atoms.

The pyrazole derivatives of the above general formula (I) preferably include compounds of the following general formulae (I-1), (I-2) and (I-3).

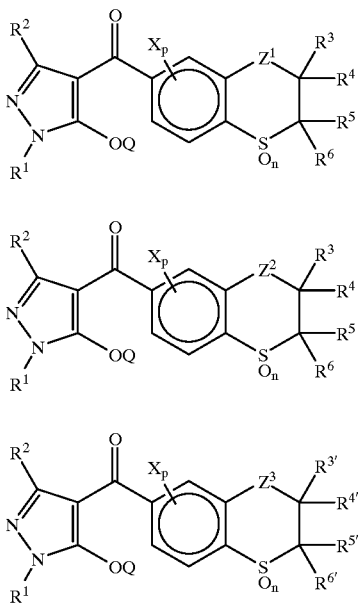
(I-1)

(I-2)

(I-3)

In the above general formula (I-1), $R^1$ to $R^6$, X, Q, n and p are as defined in the general formula (I). $Z^1$ is a group of the following (a), (b-1) or (c-1).

(a)

(b-1)

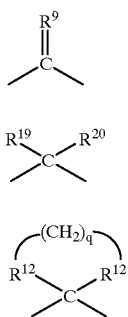
(c-1)

$R^9$ in the formula (a) is an oxygen atom or a sulfur atom, $R^{19}$ in the formula (b-1) is a halogen atom, a $C_1\sim C_4$ alkoxy group, a $C_1\sim C_4$ alkylthio group or any group of the following formulae,

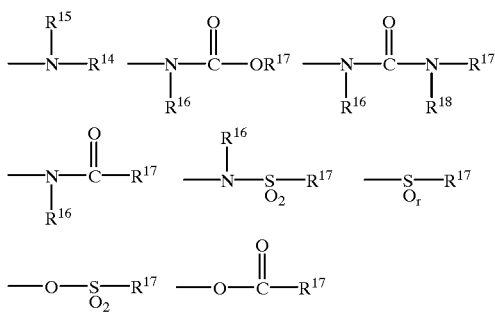

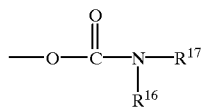

in which each of $R^{14}$ and $R^{15}$ is independently a hydrogen atom, an oxygen atom or a $C_1\sim C_4$ alkyl group, $R^{16}$ is a hydrogen atom or a $C_1\sim C_4$ alkyl group, each of $R^{17}$ and $R^{18}$ is independently a $C_1\sim C_4$ alkyl group or a $C_1\sim C_4$ haloalkyl group, and r is an integer of 0, 1 or 2, and $R^{20}$ is a hydrogen atom, a $C_1\sim C_4$ alkyl group, a $C_1\sim C_4$ alkoxy group or a $C_1\sim C_4$ alkylthio group, or may form a bonding with $R^3$, provided that in no case, $R^{19}$ is a $C_1\sim C_4$ alkoxy group and $R^{20}$ is a hydrogen atom. Specific examples of these groups include those specified in the explanation of $R^{10}$ and $R^{11}$ in the formula (b) in the definition of Z in the general formula (I). In the formula (c-1), q is an integer of 2 to 4, and $R^{12}$ is an oxygen atom, a sulfur atom or —$CH_2$—.

In the above general formula (I-2), $R^1$ to $R^6$, X, Q, n and p are as defined in the general formula (I). $Z^2$ is a group of the following (a), (b-2) or (c-1).

(a)

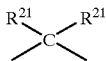
(b-2)

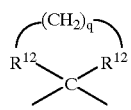
(c-1)

The group (a) and the group (c-1) are as defined above. $R^{21}$ in the formula (b-2) is a $C_1\sim C_4$ alkoxy group or a $C_1\sim C_4$ alkylthio group. Specific examples of these groups are as specified above.

Of the pyrazole derivatives of the above general formulae (I-1) and (I-2), compounds of the following general formula (I-4) are preferred.

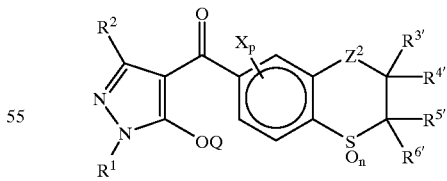
(I-4)

In the above general formula (I-4), $R^1$, $R^2$, X, Q, $Z^2$, n and p are as defined above. $R^{3'}$, $R^{4'}$, $R^{5'}$ and $R^{6'}$ have the same meanings as those of $R^3$, $R^4$, $R^5$ and $R^6$ from which the definition of "$R^3$ or $R^4$ may form a bonding with $R^5$ or $R^6$" is excluded.

Of the pyrazole derivatives of the above general formula (I-4), particularly preferred are compounds of the general formula (I-4) wherein $Z^2$ is a group of

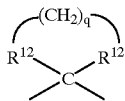

in which q is 2 and $R^{12}$ is an oxygen atom or a sulfur atom, and compounds of the general formula (I-4) wherein $Z^2$ is a carbonyl group [$R^9$ in the formula (a) is an oxygen atom].

In the above general formula (I-3), $R^1$, $R^2$, $R^{3'}$, $R^{4'}$, $R^{5'}$, $R^{6'}$, X, Q, n and p are as defined above. $Z^3$ is a group of

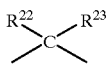

wherein $R^{22}$ is a halogen atom, a $C_1\sim C_4$ alkylthio group a $C_2\sim C_6$ alkoxyalkyl group or any group of the following formulae,

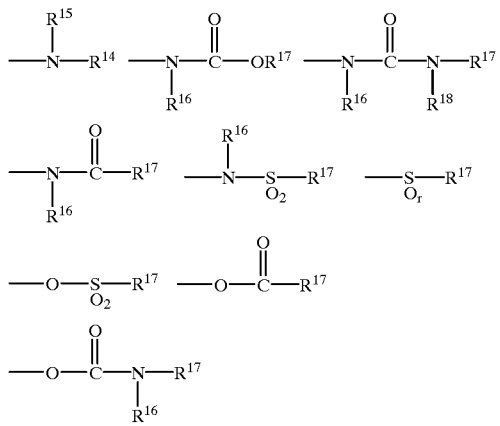

in which each of $R^{14}$ and $R^{15}$ is independently a hydrogen atom, an oxygen atom or a $C_1\sim C_4$ alkyl group, $R^{16}$ is a hydrogen atom or a $C_1\sim C_4$ alkyl group, each of $R^{17}$ and $R^{18}$ is independently a $C_1\sim C_4$ alkyl group or a $C_1\sim C_4$ haloalkyl group, and r is an integer of 0, 1 or 2, $R^{23}$ is a hydrogen atom or a $C_1\sim C_4$ alkyl group, or $R^{23}$ may form a bonding with $R^{3'}$. Specific examples of these groups and the halogen atom include those specified in the explanation of $R^{10}$ and $R^{11}$ in the formula (b) in the definition of Z in the general formula (I).

Of the pyrazole derivatives of the above general formula (I-3), preferred are compounds of the following general formula (I-5).

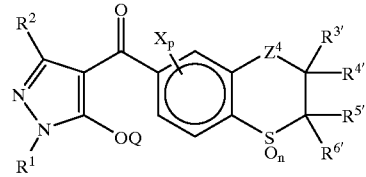

(I-5)

In the above general formula (I-5), $R^1$, $R^2$, $R^{3'}$, $R^{4'}$, $R^{5'}$, $R^{6'}$, X, Q, n and p are as defined above. $Z^4$ is a group of

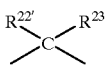

in which $R^{23}$ is the same as $R^{23}$ in the definition of $Z^3$ in the above general formula (I-3), and $R^{22'}$ has the same meaning as that of $R^{22'}$ in the definition of said $Z^3$ from which a $C_2\sim C_6$ alkoxyalkyl group is excluded.

Of the pyrazole derivatives of the above general formula (I-5), particularly preferred are compounds of the general formula (I-5) in which $R^{22'}$ in the definition of the above $Z^4$ is a chlorine atom, ethylthio, methylamino, N-methylcarbamoyloxy or N-methyl-N-methoxycarbonylamino.

Preferred combinations of substituents of the pyrazole derivatives of the general formula (I) are as shown in the following Tables 1 to 19. Concerning Xp in Tables, for example, 5-$CH_3$ means that methyl is substituted on the 5-position of the thiochroman ring, 5,8-$(CH_3)_2$ means that methyl groups are substituted both on the 5-position and on the 8-position of the thiochroman ring, and 5-$CH_3$-8-Cl means that methyl is substituted on the 5-position of the thiochroman ring and that a chlorine atom is substituted on the 8-position of the thiochroman ring. Further, "-" in Xp is p=0 and it means that no substituent X is possessed.

TABLE 1

$R^1 = C_2H_5$    $R^5 = R^6 = H$
$R^2 = H$    n = 2

| $R^3$ | $R^4$ | $X_p$ | Z | Q |
|---|---|---|---|---|
| H | H | 5-$CH_3$ | (C=O) | H |

TABLE 1-continued
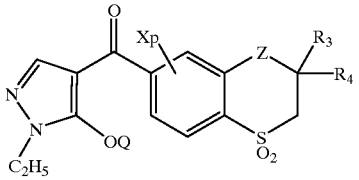
$R^1 = C_2H_5$  $R^5 = R^6 = H$
$R^2 = H$  $n = 2$
| $R^3$ | $R^4$ | $X_p$ | Z | Q |
|---|---|---|---|---|
| H | H | 5-CH$_3$ |  | —SO$_2$-n-C$_3$H$_7$ |
| CH$_3$ | CH$_3$ | 5-CH$_3$ |  | H |
| CH$_3$ | CH$_3$ | 5-CH$_3$ |  | —SO$_2$-n-C$_3$H$_7$ |
| CH$_3$ | CH$_3$ | 5-CH$_3$ |  | 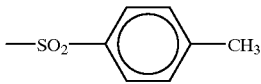 |
| CH$_3$ | CH$_3$ | 5-CH$_3$ |  | 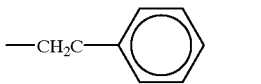 |
| H | H | 5-CH$_3$ |  | H |
| H | H | 5-CH$_3$ |  | —SO$_2$-n-C$_3$H$_7$ |
| CH$_3$ | CH$_3$ | 5-CH$_3$ |  | H |
| CH$_3$ | CH$_3$ | 5-CH$_3$ |  | —SO$_2$-n-C$_2$H$_7$ |
| H | H | 5,8-(CH$_3$)$_2$ |  | H |
| H | H | 5,8-(CH$_3$)$_2$ |  | —SO$_2$-n-C$_3$H$_7$ |
| CH$_3$ | CH$_3$ | 5,8-(CH$_3$)$_2$ |  | H |

TABLE 2

[Structure: pyrazole ring (N-C₂H₅, OQ) with C(=O) linker to benzene ring bearing Xp substituents, fused to a ring containing Z, R₃, R₄, and S(O₂)]

$R^1 = C_2H_5$  $R^6 = R^5 = H$
$R^2 = H$  $n = 2$

| R³ | R⁴ | Xₚ | Z | Q |
|---|---|---|---|---|
| CH₃ | CH₃ | 5,8-(CH₃)₂ | C=O | —SO₂-n-C₃H₇ |
| CH₃ | CH₃ | 5,8-(CH₃)₂ | C=O | —SO₂-C₆H₄-CH₃ |
| CH₃ | CH₃ | 5,8-(CH₃)₂ | C=O | —CH₂-C₆H₅ |
| CH₃ | CH₃ | 5,8-(CH₃)₂ | C=S | H |
| CH₃ | CH₃ | 5,8-(CH₃)₂ | C=S | —SO₂-n-C₃H₇ |
| CH₃ | CH₃ | 5-CH₃-8-Cl | C=O | H |
| CH₃ | CH₃ | 5-CH₃-8-Cl | C=O | —SO₂-n-C₃H₇ |
| CH₃ | CH₃ | 5-CH₃-8-F | C=O | H |
| CH₃ | CH₃ | 5-CH₃8-F | C=O | —SO₂-n-C₃H₇ |
| CH₃ | CH₃ | 5-Cl | C=O | H |
| CH₃ | CH₃ | 5-Cl | C=O | —SO₂-n-C₃H₇ |
| CH₃ | CH₃ | 5-CF₃ | C=O | H |

TABLE 2-continued

[Structure: pyrazole-C(=O)-benzene(Xp)-fused ring with Z, R3, R4, S(O2); N-C2H5, OQ]

$R^1 = C_2H_5$  $R^6 = R^5 = H$
$R^2 = H$  $n = 2$

| $R^3$ | $R^4$ | $X_p$ | Z | Q |
|---|---|---|---|---|
| CH$_3$ | CH$_3$ | 5-CF$_3$ | C(=O)CH$_3$ (acetyl) | —SO$_2$-n-C$_3$H$_7$ |
| CH$_3$ | CH$_3$ | 5-OCH$_3$ | C(=O)CH$_3$ | H |
| CH$_3$ | CH$_3$ | 5-OCH$_3$ | C(=O)CH$_3$ | —SO$_2$-n-C$_3$H$_7$ |

TABLE 3

[Structure: pyrazole-C(=O)-benzene(Xp)-fused ring with Z, R3, R4, S(O2); N-C2H5, OQ]

$R^1 = C_2H_5$  $R^5 = R^6 = H$
$R^2 = H$  $n = 2$

| $R^3$ | $R^4$ | $X_p$ | Z | Q |
|---|---|---|---|---|
| CH$_3$ | CH$_3$ | 5-OCF$_3$ | C(=O)CH$_3$ | H |
| CH$_3$ | CH$_3$ | 5-OCF$_3$ | C(=O)CH$_3$ | —SO$_2$-n-C$_3$H$_7$ |
| H | H | 5-CH$_3$ | 2-methyl-1,3-dioxolane | H |
| H | H | 5-CH$_3$ | 2-methyl-1,3-dioxolane | —SO$_2$-n-C$_3$H$_7$ |
| H | H | 5-CH$_3$-8-F | 2-methyl-1,3-dioxolane | H |

TABLE 3-continued

[Structure: pyrazole-C(=O)- connected to a benzothiopyran-S(O)₂ ring system with substituents Xp, Z, R₃, R₄; pyrazole bears N-C₂H₅ and OQ]

$R^1 = C_2H_5$   $R^5 = R^6 = H$
$R^2 = H$   $n = 2$

| R³ | R⁴ | X_p | Z | Q |
|---|---|---|---|---|
| H | H | 5-CH₃-8-F | C(CH₃)₂ with 1,3-dioxolane (O-C-O) | —SO₂-n-C₃H₇ |
| H | H | 5-CH₃ | C(CH₃)₂ with 1,3-dithiolane (S-C-S) | H |
| H | H | 5-CH₃ | C(CH₃)₂ with 1,3-dithiolane (S-C-S) | —SO₂n-C₃H₇ |
| H | H | 3-CH₃-8-F | C(CH₃)₂ with 1,3-dithiolane (S-C-S) | H |
| H | H | 5-CH₃-8-F | C(CH₃)₂ with 1,3-dithiolane (S-C-S) | —SO₂-n-C₃H₇ |
| H | H | 5-CH₃ | C(CH₃)(OCH₃)₂ | H |
| H | H | 5-CH₂ | C(CH₃)(OCH₃)₂ | —SO₂-n-C₃H₇ |
| H | H | 5-CH₃ | C(CH₃)(SCH₃)₂ | H |
| H | H | 5-CH₃ | C(CH₃)(SCH₃)₂ | —SO₂-n-C₃H₇ |
| F | F | 5-CH₂ | C(=O)CH₃ | H |

TABLE 4

[Structure: pyrazole-carbonyl-benzothiine with substituents; pyrazole has CH₃ at 3-position, OQ at 5-position, N-CH₃; benzo ring has Xp; fused ring contains Z, R₃, R₄, and S O₂]

R¹ = CH₃    R⁵ = R⁶ = H
R² = CH₃    n = 2

| R³ | R⁴ | X_p | Z | Q |
|---|---|---|---|---|
| H | H | 5-CH₃ | C=O (CH₃, CH₃) | H |
| H | H | 5-CH₃ | C=O (CH₃, CH₃) | —SO₂-n-C₃H₇ |
| CH₃ | CH₃ | 5-CH₃ | C=O (CH₃, CH₃) | H |
| CH₃ | CH₃ | 5-CH₃ | C=O (CH₃, CH₃) | —SO₂-n-C₃H₇ |
| CH₃ | CH₃ | 5-CH₃ | C=O (CH₃, CH₃) | —SO₂—C₆H₄—CH₃ |
| CH₃ | CH₃ | 5-CH₃ | C=O (CH₃, CH₃) | —CH₂—C₆H₅ |
| H | H | 5-CH₃ | C=S (CH₃, CH₃) | H |
| H | H | 5-CH₃ | C=S (CH₃, CH₃) | —SO₂-n-C₃H₇ |
| CH₃ | CH₃ | 5-CH₃ | C=S (CH₃, CH₃) | H |
| CH₃ | CH₃ | 5-CH₃ | C=S (CH₃, CH₃) | —SO₂-n-C₃H₇ |
| H | H | 5,8-(CH₃)₂ | C=O (CH₃, CH₃) | H |
| H | H | 5,8-(CH₃)₂ | C=O (CH₃, CH₃) | —SO₂-n-C₃H₇ |

TABLE 4-continued

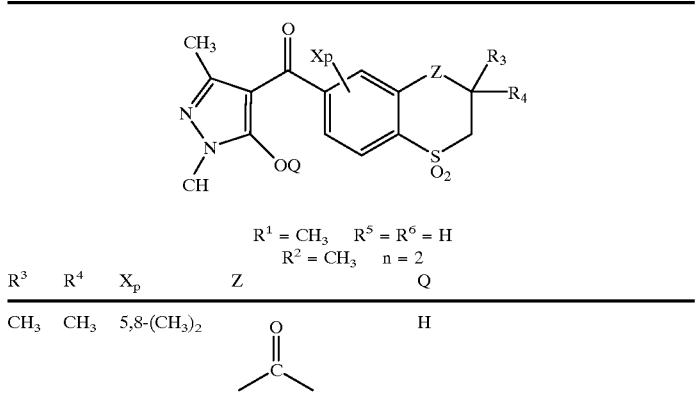

$R^1 = CH_3$  $R^5 = R^6 = H$
$R^2 = CH_3$  $n = 2$

| $R^3$ | $R^4$ | $X_p$ | Z | Q |
|---|---|---|---|---|
| CH$_3$ | CH$_3$ | 5,8-(CH$_3$)$_2$ | (C=O, CH$_3$, CH$_3$) | H |

TABLE 5

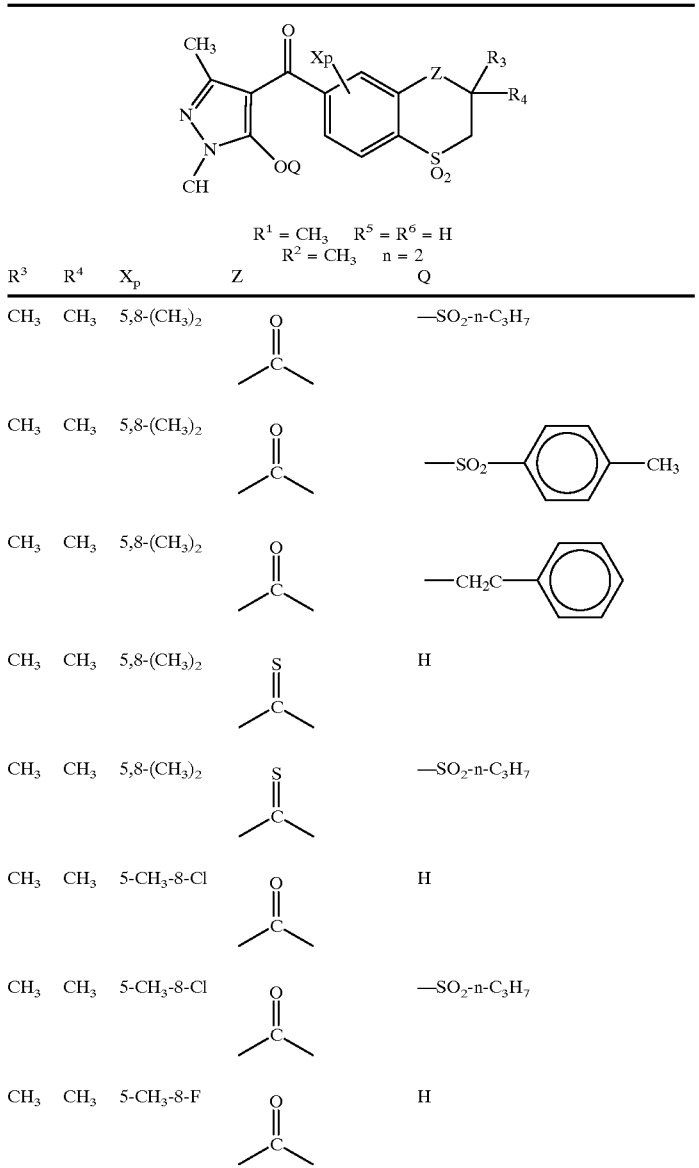

$R^1 = CH_3$  $R^5 = R^6 = H$
$R^2 = CH_3$  $n = 2$

| $R^3$ | $R^4$ | $X_p$ | Z | Q |
|---|---|---|---|---|
| CH$_3$ | CH$_3$ | 5,8-(CH$_3$)$_2$ | (C=O, CH$_3$, CH$_3$) | —SO$_2$-n-C$_3$H$_7$ |
| CH$_3$ | CH$_3$ | 5,8-(CH$_3$)$_2$ | (C=O, CH$_3$, CH$_3$) | —SO$_2$—C$_6$H$_4$—CH$_3$ |
| CH$_3$ | CH$_3$ | 5,8-(CH$_3$)$_2$ | (C=O, CH$_3$, CH$_3$) | —CH$_2$—C$_6$H$_5$ |
| CH$_3$ | CH$_3$ | 5,8-(CH$_3$)$_2$ | (C=S, CH$_3$, CH$_3$) | H |
| CH$_3$ | CH$_3$ | 5,8-(CH$_3$)$_2$ | (C=S, CH$_3$, CH$_3$) | —SO$_2$-n-C$_3$H$_7$ |
| CH$_3$ | CH$_3$ | 5-CH$_3$-8-Cl | (C=O, CH$_3$, CH$_3$) | H |
| CH$_3$ | CH$_3$ | 5-CH$_3$-8-Cl | (C=O, CH$_3$, CH$_3$) | —SO$_2$-n-C$_3$H$_7$ |
| CH$_3$ | CH$_3$ | 5-CH$_3$-8-F | (C=O, CH$_3$, CH$_3$) | H |

TABLE 5-continued
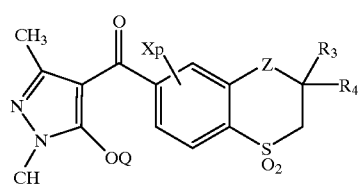
$R^1 = CH_3$   $R^5 = R^6 = H$
$R^2 = CH_3$   $n = 2$
| $R^3$ | $R^4$ | $X_p$ | Z | Q |
|-------|-------|-------|---|---|
| $CH_3$ | $CH_3$ | 5-$CH_3$-8-F |  | —$SO_2$-n-$C_3H_7$ |
| $CH_3$ | $CH_3$ | 5-Cl |  | H |
| $CH_3$ | $CH_3$ | 5-Cl | 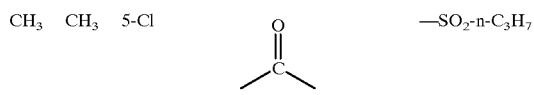 | —$SO_2$-n-$C_3H_7$ |
| $CH_3$ | $CH_3$ | 5-$CF_3$ |  | H |
| $CH_3$ | $CH_3$ | 5-$CF_3$ | 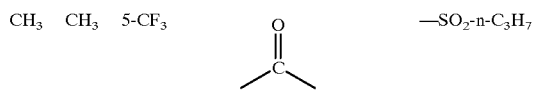 | —$SO_2$-n-$C_3H_7$ |
| $CH_3$ | $CH_3$ | 5-$OCH_3$ | 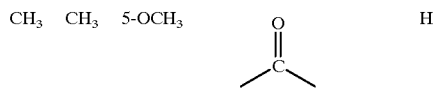 | H |

TABLE 5-continued
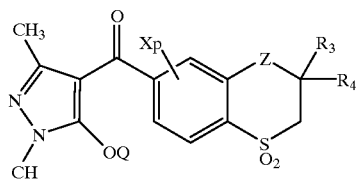
R¹ = CH₃  R⁵ = R⁶ = H
R² = CH₃  n = 2
| R³ | R⁴ | Xₚ | Z | Q |
|---|---|---|---|---|
| CH₃ | CH₃ | 5-OCH₃ | 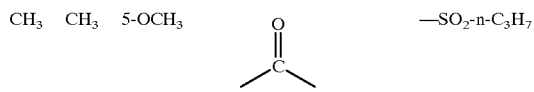 | —SO₂-n-C₃H₇ |
TABLE 6
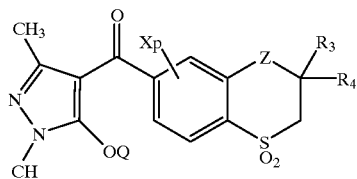
R¹ = CH₃  R⁵ = R⁶ = H
R² = CH₃  n = 2
| R³ | R⁴ | Xₚ | Z | Q |
|---|---|---|---|---|
| CH₃ | CH₃ | 5-OCF₃ | 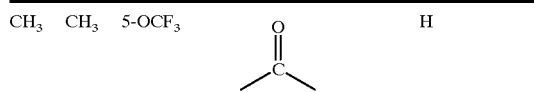 | H |
| CH₃ | CH₃ | 5-OCF₃ | 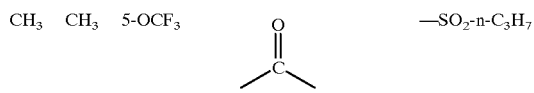 | —SO₂-n-C₃H₇ |
| H | H | 5-CH₃ | 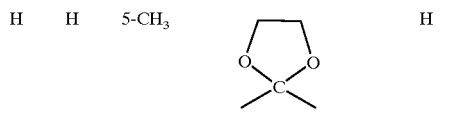 | H |
| H | H | 5-CH₃ | 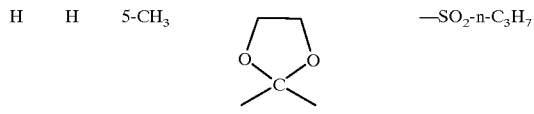 | —SO₂-n-C₃H₇ |
| H | H | 5-CH₃-8-F | 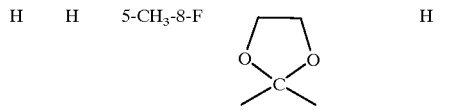 | H |

TABLE 6-continued

[Structure: pyrazole-methanone connected to benzothiopyran-S,S-dioxide system]

$R^1 = CH_3$  $R^5 = R^6 = H$
$R^2 = CH_3$  $n = 2$

| $R^3$ | $R^4$ | $X_p$ | Z | Q |
|---|---|---|---|---|
| H | H | 5-CH$_3$-8-F | 2,2-dimethyl-1,3-dioxolane | —SO$_2$-n-C$_3$H$_7$ |
| H | H | 5-CH$_3$ | 2-methyl-1,3-dithiolane | H |
| H | H | 5-CH$_3$ | 2-methyl-1,3-dithiolane | —SO$_2$-n-C$_3$H$_7$ |
| H | H | 5-CH$_3$-8-F | 2-methyl-1,3-dithiolane | H |
| H | H | 5-CH$_3$-8-F | 2-methyl-1,3-dithiolane | —SO$_2$-n-C$_3$H$_7$ |
| H | H | 5-CH$_3$ | C(OCH$_3$)$_2$CH$_3$ | H |
| H | H | 5-CH$_3$ | C(OCH$_3$)$_2$CH$_3$ | —SO$_2$-n-C$_3$H$_7$ |
| H | H | 5-CH$_3$ | C(SCH$_3$)$_2$CH$_3$ | H |
| H | H | 5-CH$_3$ | C(SCH$_3$)$_2$CH$_3$ | —SO$_2$-n-C$_3$H$_7$ |
| F | F | 5-CH$_3$ | C(=O)CH$_3$ | H |

TABLE 7
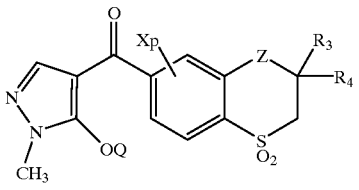
$R^1 = CH_3$   $R^5 = R^6 = H$
$R^2 = H$   $n = 2$
| $R^3$ | $R^4$ | $X_p$ | Z | Q |
|---|---|---|---|---|
| H | H | 5-CH$_3$ | C(=O) | H |
| H | H | 5-CH$_3$ | C(=O) | —SO$_2$-n-C$_3$H$_7$ |
| CH$_3$ | CH$_3$ | 5-CH$_3$ | C(=O) | H |
| CH$_3$ | CH$_3$ | 5-CH$_3$ | C(=O) | H |
| CH$_3$ | CH$_3$ | 5-CH$_3$ | C(=O) | —SO$_2$-n-C$_3$H$_7$ |
| CH$_3$ | CH$_3$ | 5-CH$_3$ | C(=O) | —SO$_2$-C$_6$H$_4$-CH$_3$ |
| CH$_3$ | CH$_3$ | 5-CH$_3$ | C(=O) | —CH$_2$C$_6$H$_5$ |
| H | H | 5-CH$_3$ | C(=S) | H |
| H | H | 5-CH$_3$ | C(=S) | —SO$_2$-n-C$_3$H$_7$ |
| CH$_3$ | CH$_3$ | 5-CH$_3$ | C(=S) | H |
| CH$_3$ | CH$_3$ | 5-CH$_3$ | C(=S) | —SO$_2$-n-C$_3$H$_7$ |
| H | H | 5,8-(CH$_3$)$_2$ | C(=O) | H |

TABLE 7-continued

[Structure: pyrazole-C(=O)-benzothiine-SO2 core with substituents Xp, Z, R3, R4, OQ, CH3, N-N]

R¹ = CH₃   R⁵ = R⁶ = H
R² = H     n = 2

| R³ | R⁴ | Xₚ | Z | Q |
|---|---|---|---|---|
| H | H | 5,8-(CH₃)₂ | C(=O) | —SO₂-n-C₃H₇ |
| CH₃ | CH₃ | 5,8-(CH₃)₂ | C(=O) | H |

TABLE 8

[Structure: pyrazole-C(=O)-benzothiine-SO2 core with substituents Xp, Z, R3, R4, OQ, CH3, N-N]

R¹ = CH₃   R⁵ = R⁶ = H
R² = H     n = 2

| R³ | R⁴ | Xₚ | Z | Q |
|---|---|---|---|---|
| CH₃ | CH₃ | 5,8-(CH₃)₂ | C(=O) | —SO₂-n-C₃H₇ |
| CH₃ | CH₃ | 5,8-(CH₃)₂ | C(=O) | —SO₂-C₆H₄-CH₃ |
| CH₃ | CH₃ | 5,8-(CH₃)₂ | C(=O) | —CH₂-C₆H₅ |
| CH₃ | CH₃ | 5,8-(CH₃)₂ | C(=S) | H |
| CH₃ | CH₃ | 5,8-(CH₃)₂ | C(=S) | —SO₂-n-C₃H₇ |
| CH₃ | CH₃ | 5-CH₃-8-Cl | C(=O) | H |
| CH₃ | CH₃ | 5-CH₃8-Cl | C(=O) | —SO₂-n-C₃H₇ |

TABLE 8-continued

[Structure: pyrazole-methyl with C(=O) linker to benzothiopyran-S,S-dioxide bearing Xp, Z, R3, R4, OQ substituents]

$R^1 = CH_3$  $R^5 = R^6 = H$
$R^2 = H$  $n = 2$

| $R^3$ | $R^4$ | $X_p$ | Z | Q |
|---|---|---|---|---|
| $CH_3$ | $CH_3$ | 5-$CH_3$-8-F | –C(=O)–CH(CH$_3$)– | H |
| $CH_3$ | $CH_3$ | 5-$CH_3$-8-F | –C(=O)–CH(CH$_3$)– | —SO$_2$-n-C$_3$H$_7$ |
| $CH_3$ | $CH_3$ | 5-Cl | –C(=O)–CH(CH$_3$)– | H |
| $CH_3$ | $CH_3$ | 5-Cl | –C(=O)–CH(CH$_3$)– | —SO$_2$-n-C$_3$H$_7$ |
| $CH_3$ | $CH_3$ | 5-$CF_3$ | –C(=O)–CH(CH$_3$)– | H |
| $CH_3$ | $CH_3$ | 5-$CF_3$ | –C(=O)–CH(CH$_3$)– | —SO$_2$-n-C$_3$H$_7$ |
| $CH_3$ | $CH_3$ | 5-$OCH_3$ | –C(=O)–CH(CH$_3$)– | H |
| $CH_3$ | $CH_3$ | 5-$OCH_3$ | –C(=O)–CH(CH$_3$)– | —SO$_2$-n-C$_3$H$_7$ |

TABLE 9

[Structure: pyrazole-methyl with C(=O) linker to benzothiopyran-S,S-dioxide bearing Xp, Z, R3, R4, OQ substituents]

$R^1 = CH_3$  $R^5 = R^6 = H$
$R^2 = H$  $n = 2$

| $R^3$ | $R^4$ | $X_p$ | Z | Q |
|---|---|---|---|---|
| $CH_3$ | $CH_3$ | 5-$OCF_3$ | –C(=O)–CH(CH$_3$)– | H |

TABLE 9-continued

[Structure: pyrazole-carbonyl-benzothiopyran-S,S-dioxide scaffold with substituents $X_p$, Z, $R_3$, $R_4$, OQ, and N-CH$_3$]

$R^1 = CH_3$  $R^5 = R^6 = H$
$R^2 = H$  $n = 2$

| $R^3$ | $R^4$ | $X_p$ | Z | Q |
|---|---|---|---|---|
| CH$_3$ | CH$_3$ | 5-OCF$_3$ | C(=O)CH$_3$ (acetyl) | —SO$_2$-n-C$_3$H$_7$ |
| H | H | 5-CH$_3$ | 2-methyl-1,3-dioxolan-2-yl | H |
| H | H | 5-CH$_3$ | 2-methyl-1,3-dioxolan-2-yl | —SO$_2$-n-C$_3$H$_7$ |
| H | H | 5-CH$_3$-8-F | 2-methyl-1,3-dioxolan-2-yl | H |
| H | H | 5-CH$_3$-8-F | 2-methyl-1,3-dioxolan-2-yl | —SO$_2$-n-C$_3$H$_7$ |
| H | H | 5-CH$_3$ | 2-methyl-1,3-dithiolan-2-yl | H |
| H | H | 5-CH$_3$ | 2-methyl-1,3-dithiolan-2-yl | —SO$_2$-n-C$_3$H$_7$ |
| H | H | 5-CH$_3$-8-F | 2-methyl-1,3-dithiolan-2-yl | H |
| H | H | 5-CH$_3$-8-F | 2-methyl-1,3-dithiolan-2-yl | —SO$_2$-n-C$_3$H$_7$ |
| H | H | 5-CH$_3$ | C(CH$_3$)(OCH$_3$)$_2$ | H |
| H | H | 5-CH$_3$ | C(CH$_3$)(OCH$_3$)$_2$ | —SO$_2$-n-C$_3$H$_7$ |

TABLE 9-continued

[Structure: pyrazole-carbonyl linked to benzothiopyran-S,S-dioxide with OQ, Xp, Z, R3, R4 substituents; N-CH3]

R¹ = CH₃    R⁵ = R⁶ = H
R² = H      n = 2

| R³ | R⁴ | Xₚ | Z | Q |
|---|---|---|---|---|
| H | H | 5-CH₃ | C(SCH₃)₂ (gem-dimethyl) | H |
| H | H | 5-CH₃ | C(SCH₃)₂ (gem-dimethyl) | —SO₂-n-C₃H₇ |
| F | F | 5-CH₃ | C(=O)CH₃ | H |

TABLE 10

[Structure: pyrazole-carbonyl linked to benzothiopyran-S,S-dioxide with OQ, Xp, Z, R3, R4 substituents; N-C₂H₅]

R¹ = C₂H₅   R⁵ = R⁶ = H
R² = H      n = 2

| R³ | R⁴ | Xₚ | Z | Q |
|---|---|---|---|---|
| H | H | — | C(=O)CH₃ | H |
| H | H | 5-CH₃-8-F | C(=O)CH₃ | H |
| H | H | 5-CH₃ | C(=O)CH₃ | —SO₂—C₆H₄—CH₃ |
| CH₃ | CH₃ | 5-Cl-8-CH₃ | C(=O)CH₃ | H |
| CH₃ | CH₃ | 5-Cl-8-CH₃ | C(=O)CH₃ | —SO₂-n-C₃H₇ |
| CH₃ | CH₃ | 5-Cl-8-CH₃ | C(=O)CH₃ | —SO₂—C₆H₄—CH₃ |

TABLE 10-continued

[Structure: pyrazole-C(=O)-benzothiane-SO2 core with Xp, Z, R3, R4, OQ substituents]

$R^1 = C_2H_5$  $R^5 = R^6 = H$
$R^2 = H$  $n = 2$

| $R^3$ | $R^4$ | $X_p$ | Z | Q |
|---|---|---|---|---|
| $CH_3$ | $CH_3$ | 5-$CF_3$-8-$CH_3$ | C(=O)(CH₃)₂ | H |
| $CH_3$ | $CH_3$ | 5-$CF_3$-8-$CH_3$ | C(=O)(CH₃)₂ | —CO—cyclohexyl |
| $CH_3$ | $CH_3$ | 5-$OCH_3$ | C(=O)(CH₃)₂ | —$SO_2$—C₆H₄—$CH_3$ |
| $CH_3$ | $CH_3$ | 5-$OCH_3$-8-Cl | C(=O)(CH₃)₂ | $SO_2$-n-$C_3H_7$ |
| H | H | 5-$CH_3$ | 1,3-dioxolane-2,2-dimethyl | —$SO_2$—C₆H₄—$CH_3$ |
| H | H | 5-Cl-8-$CH_3$ | 1,3-dithiolane-2,2-dimethyl | H |
| H | H | 5-Cl-8-$CH_3$ | 1,3-dithiolane-2,2-dimethyl | $SO_2$-n-$C_3H_7$ |

TABLE 11

[Structure: pyrazole-C(=O)-benzothiane-SO2 core with Xp, Z, R3, R4, OQ substituents]

$R^1 = C_2H_5$  $R^5 = R^6 = H$
$R^2 = H$  $n = 0$

| $R^3$ | $R^4$ | $X_p$ | Z | Q |
|---|---|---|---|---|
| H | H | — | C(=O)(CH₃)₂ | H |

TABLE 11-continued

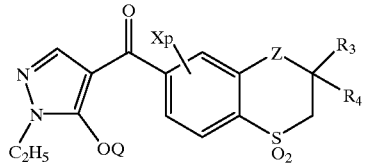

$R^1 = C_2H_5$, $R^5 = R^6 = H$
$R^2 = H$, $n = 0$

| $R^3$ | $R^4$ | $X_p$ | Z | Q |
|---|---|---|---|---|
| H | H | 5-CH$_3$ | | H |
| H | H | 5,8-(CH$_3$)$_2$ | | H |

TABLE 12

$R^1 = C_2H_5$, $R^5 = R^6 = H$
$R^2 = H$, $n = 1$

| $R^3$ | $R^4$ | $X_p$ | Z | Q |
|---|---|---|---|---|
| CH$_3$ | CH$_3$ | 5,8-(CH$_3$)$_2$ | | H |
| CH$_3$ | CH$_3$ | 5,8-(CH$_3$)$_2$ | | —SO$_2$-n-C$_3$H$_7$ |

TABLE 13

$R^1 = C_2H_5$, $R^3 = R^5 = H$
$R^2 = H$, $R^4$ and $R^6$ forms a bond

| n | $X_p$ | Z | Q |
|---|---|---|---|
| 0 | 5,8-(CH$_3$)$_2$ | | H |

TABLE 13-continued

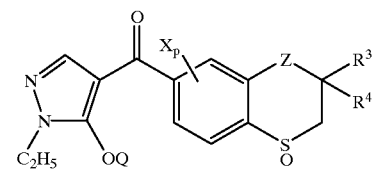

$R^1 = C_2H_5$, $R^3 = R^5 = H$
$R^2 = H$, $R^4$ and $R^6$ forms a bond

| n | $X_p$ | Z | Q |
|---|---|---|---|
| 2 | 5,8-(CH$_3$)$_2$ | | H |

TABLE 14

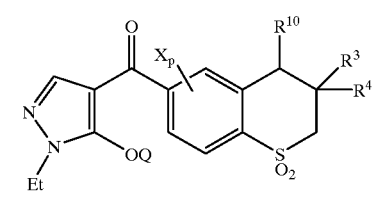

$R^1 = C_2H_5$, $R^2 = H$, $R^5 = R^6 = H$, $R^{11} = H$, $n = 2$

| $R^3$ | $R^4$ | $R^{10}$ | X | Q |
|---|---|---|---|---|
| H | H | Cl | 5-CH$_3$ | H |
| H | H | Cl | 5-CH$_3$ | —SO$_2$-n-C$_3$H$_7$ |
| H | H | Cl | 5-CH$_3$ | —SO$_2$-p-C$_6$H$_4$—CH$_3$ |
| H | H | Cl | 5-CH$_3$ | —CH$_2$COC$_6$H$_5$ |
| H | Cl | Cl | 5-CH$_3$ | H |
| H | Cl | Cl | 5-CH$_3$ | —SO$_2$-n-C$_3$H$_7$ |
| H | H | Cl | 5-CH$_3$-8-Cl | —SO$_2$-n-C$_3$H$_7$ |
| H | H | Cl | 5,8-(CH$_3$)$_2$ | H |
| F | F | Cl | 5,8-(CH$_3$)$_2$ | H |
| CH$_3$ | CH$_3$ | Cl | 5-CH$_3$ | H |
| CH$_3$ | CH$_3$ | Cl | 5-CH$_3$ | —SO$_2$-n-C$_3$H$_7$ |
| CH$_3$ | CH$_3$ | Cl | 5-CF$_3$ | H |
| CH$_3$ | CH$_3$ | Cl | 5-OCH$_3$ | H |
| CH$_3$ | CH$_3$ | Cl | 5,8-(CH$_3$)$_2$ | H |

TABLE 14-continued $R^1 = C_2H_5$, $R^2 = H$, $R^5 = R^6 = H$, $R^{11} = H$, n = 2

| $R^3$ | $R^4$ | $R^{10}$ | X | Q |
|---|---|---|---|---|
| CH₃ | CH₃ | Cl | 5-CH₃-8-F | H |
| CH₃ | CH₃ | Br | 5-CH₃ | H |
| CH₃ | CH₃ | I | 5-CH₃ | H |
| H | H | —SCH₃ | 5-CH₃ | H |
| H | H | —SC₂H₅ | 5-CH₃ | H |
| H | H | —SC₂H₅ | 5-CH₃ | —SO₂-n-C₃H₇ |
| H | H | —SO₂CH₃ | 5-CH₃ | H |
| H | H | —SO₂C₂H₅ | 5-CH₃ | H |
| CH₃ | CH₃ | —SC₂H₅ | 5-CH₃ | H |
| CH₃ | CH₃ | —SC₂H₅ | 5-CH₃ | —SO₂-n-C₃H₇ |
| H | H | —NH₂ | 5-CH₃ | H |
| H | H | —NHCH₃ | 5-CH₃ | —SO₂-n-C₃H₇ |
| H | H | —NHC₂H₅ | 5-CH₃ | H |
| H | H | —NHC₃H₇ | 5-CH₃ | H |
| H | H | —N(CH₃)₂ | 5-CH₃ | H |

TABLE 15

$R^1 = C_2H_5$, $R^2 = H$, $R^5 = R^6 = H$, $R^{11} = H$, n = 2

| $R^3$ | $R^4$ | $R^{10}$ | X | Q |
|---|---|---|---|---|
| H | H | —N(CH₃)CO₂CH₃ | 5-CH₃ | H |
| H | H | —N(CH₃)CO₂C₂H₅ | 5-CH₃ | H |
| H | H | —N(CH₃)CONHCH₃ | 5-CH₃ | H |
| H | H | —N(CH₃)CONHC₂H₅ | 5-CH₃ | H |
| H | H | —N(CH₃)CONH-n-C₃H₇ | 5-CH₃ | H |
| H | H | —N(CH₃)COCH₃ | 5-CH₃ | H |
| H | H | —N(CH₃)COC₂H₅ | 5-CH₃ | H |
| H | H | —N(CH₃)SO₂CH₃ | 5-CH₃ | H |
| H | H | —N(CH₃)SO₂C₂H₅ | 5-CH₃ | H |
| H | H | —N(CH₃)SO₂-n-C₃H₇ | 5-CH₃ | —SO₂-n-C₃H₇ |
| H | H | NO₂ | 5-CH₃ | H |
| H | H | —OSO₂CH₃ | 5-CH₃ | H |
| H | H | —OSO₂C₂H₅ | 5-CH₃ | H |
| H | H | —OSO₂-n-C₃H₇ | 5-CH₃ | H |
| H | H | —OCON(CH₃)₂ | 5-CH₃ | H |
| H | H | —OCOCH₃ | 5-CH₃ | H |
| H | H | —OCOC₂H₅ | 5-CH₃ | H |
| H | H | —OCO-n-C₃H₇ | 5-CH₃ | H |
| CH₃ | CH₃ | —N(CH₃)CO₂CH₃ | 5-CH₃ | H |
| CH₃ | CH₃ | —N(CH₃)CONHCH₃ | 5-CH₃ | H |
| CH₃ | CH₃ | —N(CH₃)COCH₃ | 5-CH₃ | H |
| CH₃ | CH₃ | —N(CH₃)SO₂CH₃ | 5-CH₃ | H |
| CH₃ | CH₃ | NO₂ | 5-CH₃ | H |
| CH₃ | CH₃ | —OSO₂CH₃ | 5-CH₃ | H |
| CH₃ | CH₃ | —OCON(CH₃)₂ | 5-CH₃ | H |
| CH₃ | CH₃ | —OCOCH₃ | 5-CH₃ | H |

TABLE 16

$R^1 = C_2H_5$, $R^2 = H$, $R^5 = R^6 = H$, $R^{11} = H$, n = 2

| $R^3$ | $R^4$ | $R^{10}$ | X | Q |
|---|---|---|---|---|
| H | H | —N(CH₃)CO₂CH₃ | 5-CH₃ | —SO₂-n-C₃H₇ |
| H | H | —N(CH₃)CONHCH₃ | 5-CH₃ | —SO₂-n-C₃H₇ |
| H | H | —N(CH₃)COCH₃ | 5-CH₃ | —SO₂-n-C₃H₇ |
| H | H | —N(CH₃)SO₂CH₃ | 5-CH₃ | —SO₂-n-C₃H₇ |
| H | H | —N(CH₃)SO₂-n-C₃H₇ | 5-CH₃ | —SO₂-n-C₃H₇ |
| H | H | NO₂ | 5-CH₃ | —SO₂-n-C₃H₇ |
| H | H | —OSO₂CH₃ | 5-CH₃ | —SO₂-n-C₃H₇ |
| H | H | —OSO₂-n-C₃H₇ | 5-CH₃ | —SO₂-n-C₃H₇ |
| H | H | —OCONHCH₃ | 5-CH₃ | —SO₂-n-C₃H₇ |
| H | H | —OCON(CH₃)₂ | 5-CH₃ | —SO₂-n-C₃H₇ |
| H | H | —OCOCH₃ | 5-CH₃ | —SO₂-n-C₃H₇ |

TABLE 17

$R^1 = C_2H_5$, $R^2 = H$, $R^3$ and $R^{11}$ forms a bond. $R^5 = R^6 = H$, n = 2

| $R^4$ | $R^{10}$ | X | Q |
|---|---|---|---|
| H | Cl | 5-CH₃ | H |
| CH₃ | F | 5-CH₃ | —SO₂-n-C₃H₇ |
| F | —SC₂H₅ | 5-CH₃ | —SO₂-p-C₆H₄—CH₃ |
| H | —SC₂H₅ | 5-CH₃ | —CH₂COC₆H₅ |
| Cl | —SO₂C₂H₅ | 5-CH₃ | H |
| H | —SO₂C₂H₅ | 5-CH₃ | H |
| H | —N(CH₃)₂ | 5-CH₃ | H |
| H | —N(CH₃)CO₂CH₃ | 5-CH₃ | H |
| H | —N(CH₃)CONHCH₃ | 5-CH₃ | H |
| H | —OCON(CH₃)₂ | 5-CH₃ | H |
| H | —NO₂ | 5-CH₃ | H |

TABLE 18

$R^1 = C_2H_5$, $R^5 = R^6 = H$, $R^2 = H$, n = 2, $R^{11} = H$

| $R^3$ | $R^4$ | $R^{10}$ | $X_p$ | Q |
|---|---|---|---|---|
| H | H | Cl | — | H |
| H | H | —NHCOCH₃ | 5,8-(CH₃)₂ | H |
| H | H | —SC₂H₅ | 5-CH₃ | H |
| H | H | —CH₂OCH₃ | 5,8-(CH₃)₂ | H |

TABLE 19

$R^1 = C_2H_5$  $R^5 = R^6 = H$
$R^2 = H$  $R^{11} = H$  $n = 0$

| $R^3$ | $R^4$ | $R^{10}$ | $X_P$ | Q |
|---|---|---|---|---|
| H | H | Cl | — | H |
| H | H | —NHCOCH$_3$ | 5,8-(CH$_3$)$_2$ | H |

The pyrazole derivatives of the general formula (I) in which Q is a hydrogen atom, i.e., the compounds of the general formula (Ia), include the following four structures due to tautomerism, and the pyrazole derivative of the present invention includes all of these compounds.

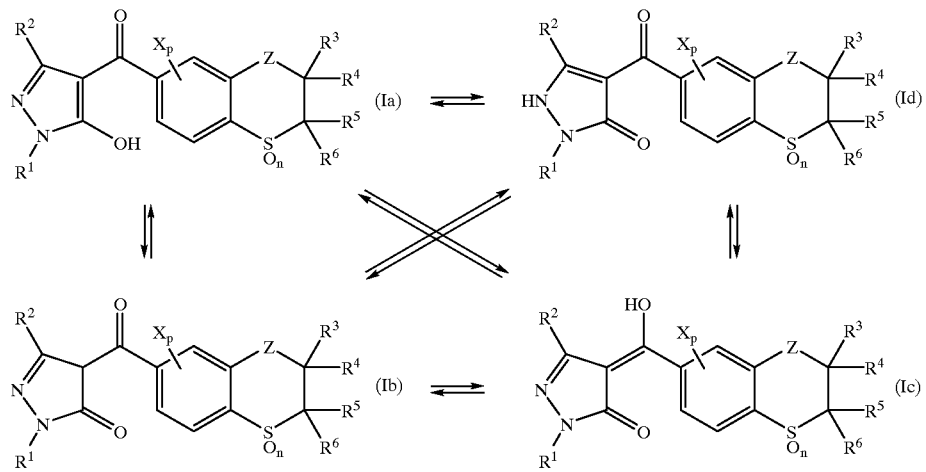

Further, the pyrazole derivatives of the formula (I) have asymmetric carbons depending upon kinds of substituents $R^3$, $R^4$, $R^5$, $R^6$ and Z, and various stereo-isomers are therefore present. The pyrazole derivatives of he present invention include all of these isomers and mixtures of these.

The pyrazole derivatives of the formula (Ia) are acidic substances, and can be easily converted to salts by treating them with a base. These salts are also included in the pyrazole derivative of the present invention.

The above base can be selected from known bases without any limitation. The base includes organic bases such as amines and anilines and inorganic bases such as sodium compounds and potassium compounds. Examples of the amines include monoalkylamine, dialkylamine and trialkylamine. Alkyl groups of the alkylamines are generally $C_1$~$C_4$ alkyl groups. Examples of the anilines include aniline, monoalkylaniline and dialkylaniline. Alkyl groups of the alkylanilines are generally $C_1$~$C_4$ alkyl groups. Examples of the sodium compounds include sodium hydroxide and sodium carbonate. Examples of the potassium compounds include potassium hydroxide and potassium carbonate.

The herbicide of the present invention contains at least one of the novel pyrazole derivatives of the general formula (1) and/or the salts thereof, provided by the present invention, as an active ingredient. These compounds are used by mixing them with a liquid carrier such as a solvent or a solid carrier such as a mineral fine powder and preparing the resultant mixtures in the form of a wettable powder, an emulsifiable concentrate, a dust or granules. These compounds can be imparted with emulsifiability, dispersibility or spreadability by adding a surfactant when the above preparations are formed.

When the herbicide of the present invention is used in the form of a wettable powder, generally, 10 to 55% by weight of the pyrazole derivative and/or the salt thereof, provided by the present invention, 40 to 88% by weight of a solid carrier and 2 to 5% by weight of a surfactant are mixed to prepare a composition, and the composition can be used. When the herbicide of the present invention is used in the form of an emulsifiable concentrate, generally, the emulsifiable concentrate can be prepared by mixing 20 to 50% by weight of the pyrazole derivative and/or the salt thereof, provided by the present invention, 35 to 75% by weight of a solvent and 5 to 15% by weight of a surfactant.

When the herbicide of the present invention is used in the form of a dust, generally, the dust can be prepared by mixing 1 to 15% by weight of the pyrazole derivative and/or the salt thereof, provided by the present invention, 80 to 97% by weight of a solid carrier and 2 to 5% by weight of a surfactant. Further, when the herbicide of the present invention is used in the form of granules, the granules can be prepared by mixing 1 to 15% by weight of the pyrazole derivative or the salt thereof, provided by the present invention, 80 to 97% by weight of a sold carrier and 2 to 5% by weight of a surfactant. The above solid carrier is selected from fine mineral powders. Examples of the fine mineral powders include oxides such as diatomaceous earth and slaked lime, phosphates such as apatite, sulfates such as gypsum and silicates such as talc, pyrophyllite, clay, kaolin, bentonite, acidic terra alba, white carbon, powdered quartz and powdered silica.

The solvent is selected from organic solvents. Specific examples of the organic solvent include aromatic hydrocarbons such as benzene, toluene and xylene, chlorinated hydrocarbons such as o-chlorotoluene, trichloroethane and trichloroethylene, alcohols such as cyclohexanol, amyl alcohol and ethylene glycol, ketones such as isophorone, cyclohexanone and cyclohexenyl-cyclohexanone, ethers such as butyl cellosolve, diethyl ether and methyl ethyl ether, esters such as isopropyl acetate, benzyl acetate and methyl phthalate, amides such as dimethylformamide, and mixtures of these.

The surfactant is selected from anionic surfactants, non-ionic surfactants, cationic surfactants and amphoteric surfactants (such as amino acid and betaine).

The herbicide of the present invention may contain other herbicidally active ingredient as required together with any one of the pyrazole derivatives of the general formula (I) and/or the salts thereof. The other herbicidally active ingredient cab be properly selected from known herbicides such as phenoxy-based, diphenyl ether-based, triazine-based, urea-based, carbamate-based, thiol carbamate-based, acid anilide-based, pyrazole-based, phosphoric acid-based, sulfonyl urea-based and oxadiazone-based herbicides.

Further, the herbicide of the present invention may contain an insecticide, a fungicide, a plant growth regulator and a fertilizer as required.

The pyrazole derivative of the present invention, represented by the general formula (I), can be produced by the following method.

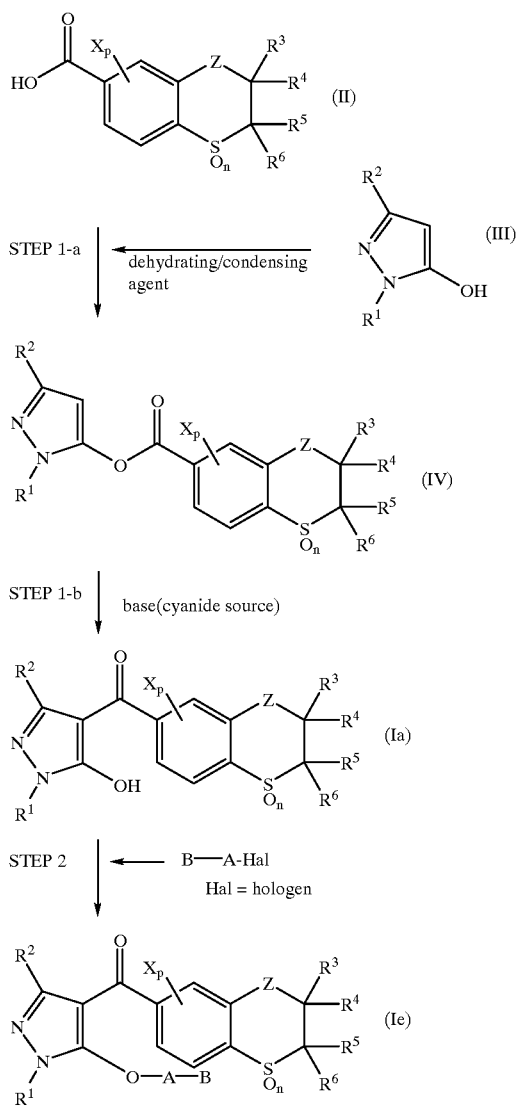

In the above reaction scheme, $R^1$, $R^2$, $R^3$, $R^4$, $R^5$, $R^6$, X, p, n and Z are as defined in the pyrazole derivatives of the general formula (I), and Hal is a halogen.

The pyrazole derivative of the general formula (I) in which Q is a hydrogen atom [pyrazole derivative of the formula (Ia)] is produced by the step 1-a of condensing the carboxylic acid of the general formula (II) and a pyrazole compound of the general formula (III) to form an ester and the step 1-b of rearranging the ester formed by the condensation.

Further, the compound of the general formula (I) in which Q is a group of -A-B [pyrazole derivative of the formula (Ie)] is produced by the step 2 of further introducing the group of -A-B into the hydroxyl group of the pyrazole derivative of the formula (Ia) obtained in the step 1. Each step will be explained in detail hereinafter.

Step 1

(Step 1-a)

The compound of the general formula (II) and the compound of the general formula (III) are allowed to react in an inert solvent in the presence of a dehydrating agent such as DCC (N,N'-dicyclohexylcarbodiimide), CDI (1,1-carbonyldiimidazole) or EDC (1-(3-dimethylaminopropyl)-3-ethylcarbodiimide) to form a pyrazole ester (IV).

In the above reaction, the amount of the compound of the general formula (III) per mole of the compound of the general formula (II) is preferably 1.0 to 3.0 mol. The amount of the dehydrating agent per mole of the compound of the general formula (II) is preferably 1.0 to 1.5 mol. The inert solvent is not specially limited so long as it is insert to the reaction. The solvent is preferably selected from secondary or tertiary alcohols such as t-butyl alcohol, t-amyl alcohol an i-propanol; halogen-containing solvents such as methylene chloride, 1,2-dichloroethane, chloroform and chlorobenzene; and ether solvents such as diethyl ether, tetrahydrofuran, dioxane and 1,2-dimethoxyethane. The reaction temperature may be set in the range of from −20° C. to the boiling point of a solvent, while the reaction temperature at or around room temperature (10 to 30° C.) is preferred.

In another method, the pyrazole ester (IV) can be also produced by reacting the compound of the general formula (II) with a halogenating agent such as thionyl chloride, phosphorus oxychloride or phosphorus tribromide in an inert solvent to convert it into a corresponding acid halide, and reacting the acid halide with the compound of the general formula (III) in an inert solvent in the presence of a base.

In the above reaction, the amount of the halogenating agent per mole of the compound of the general formula (II) is preferably at least 1.0 mol. Thionyl chloride as a halogenating agent may be used as a reaction solvent. The inert solvent is not specially limited so long as it is insert to the reaction. The inert solvent is preferably selected from halogen-containing solvents such as methylene chloride, 1,2-dichloroethane, carbon tetrachloride and chlorobenzene or aromatic hydrocarbons such as toluene and xylene. The reaction temperature may be set in the range of from room temperature to the boiling point of a solvent, while the reaction temperature of from 50 to 100° C. is preferred.

The amount of the compound of the general formula (III) per mole of the obtained acid halide is preferably 1.0 to 3.0 mol. Although not specially limited, the base is selected from organic bases such as triethylamine and pyridine or inorganic bases such as sodium carbonate and potassium carbonate, and the amount of the base per normality of the acid halide is preferably 1.0 to 3.0 N. The inert solvent used for the esterification is not specially limited so long as it is inert to the reaction, and it is preferably selected from halogen-containing solvents such as methylene chloride, 1,2-dichloroethane, chloroform and chlorobenzene or ether solvents such as diethyl ether, tetrahydrofuran, dioxane and 1,2-dimethoxyethane. The reaction temperature may be set in the range of from −20° C. to the boiling point of a solvent, while the reaction temperature of from 20 to 20° C. is preferred.

The pyrazole compound of the general formula (III) used as a reactant in the above reaction can be synthesized, for example, by the method disclosed in JP-A-61-257974.

(Step 1-b)

The pyrazole ester of the general formula (IV) is allowed to react in an inert solvent in the presence of a base, to produce a pyrazole derivative of the general formula (Ia). The rearrangement reaction can be proceeded with under more moderate temperature conditions by allowing a so-called cyanide source to be present in the reaction system.

The cyanide source is a compound which can generate cyanide ion in the reaction system, and for example, it refers to an organic cyanohydrin compound such as acetonecyanohydrin. Further, cyanide ion can be generated in the organic solvent by the use of an inorganic cyano compound such as sodium cyanide or potassium cyanide and a metal-ion-inclusion phase transfer catalyst such as 18-crown-6 or benzo-18-crown-6 in combination.

The base used in the above reaction is not specially limited, while it is preferred to use an organic base such as triethylamine or pyridine or an inorganic base such as sodium carbonate or potassium carbonate in an amount of 1.0 to 3.0 N per normality of the pyrazole ester. The cyanide source is not always necessary, while the amount of the cyanide source per mole of the pyrazole ester is preferably 0.01 to 0.2 mol when it is used. The inert solvent is not specially limited so long as it is inert to the reaction, and dioxane or acetonitrile is preferred. When the cyanide source is co-present, the reaction temperature is preferably at or around room temperature, and when the cyanide source is not present, the reaction temperature is preferably 50 to 130° C.

As particularly preferred conditions, when the cyanide source is used, the reaction is carried out in acetonitrile as a solvent at or around a room temperature (10~25° C.) in the presence of triethylamine as a base, or when no cyanide source is used, the reaction is carried out in dioxane as a solvent at the boiling point of the solvent (about 100° C.) in the presence of potassium carbonate as a base.

(Steps 1-a, b)

When the step 1-a and the step 1-b use a proper reaction reagent and proper conditions, the pyrazole derivative of the general formula (Ia) can be produced in one reaction without isolating the pyrazole ester (IV) which is an intermediate. For example, there is a method in which DCC is used as a dehydrating agent in the step 1-a and the compound of the general formula (II) and the compound of the general formula (III) are allowed to react in an inert solvent in the presence of DCC and a base.

In the above reaction, the amount of the compound of the general formula (III) per mole of the compound of the general formula (II) is preferably 1.0 to 3.0 mol. The amount of DCC per mole of the compound of the general formula (II) is preferably 1.0 to 1.5 mol. The base used together with DCC is not specially limited, and preferably, potassium carbonate or sodium carbonate is used in an amount of 0.5 to 2.0 mol per mole of the compound of the general formula (II). The inert solvent is not specially limited so long as it is inert to the reaction, while it is preferably selected from secondary or tertiary alcohols schematic as t-butyl alcohol, t-amyl alcohol and i-propanol. The reaction temperature can be set in the range of from room temperature to the boiling point of a solvent, while it is preferably 50 to 100° C.

Step 2

The compound (Ia) obtained in the step 1 is reacted with B-A-Hal of the general formula (V) (A, B and Hal are as defined already) in an inert solvent in the presence of a base, to obtain a compound (Ie).

In this step, the compound (Ia)/compound (V) molar ratio is preferably 1/1~1/3. For capturing hydrogen halide formed as a byproduct in the reaction, further, it is preferred to use a base such as sodium carbonate, potassium carbonate, triethylamine or pyridine in a molar amount equivalent to, or greater than, the molar amount of the starting material of the general formula (Ia). The reaction temperature is preferably set in the range of from room temperature to the boiling point of a solvent. The solvent for the reaction is selected from aromatic hydrocarbons such as benzene and toluene, ethers such as diethyl ether, ketones such as methyl ethyl ketone and halogen-containing hydrocarbons such as methylene chloride and chloroform. Further, a two-phase solvent consisting of any one of the solvents and water may be used, and in this case, a desirable result can be obtained by adding a phase transfer catalyst such as crown ether or benzyltriethylammonium chloride.

The aromatic carboxylic acid derivatives of the general formula (II),

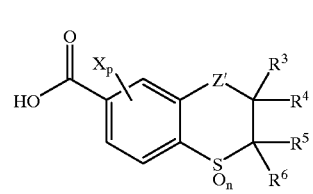
(II)

wherein $R^3$, $R^4$, $R^5$, $R^6$, X, p and n are as defined in the pyrazole derivatives of the general formula (I), and Z' is a group of the following (a), (b') or (c),

(a)

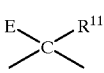
(b')

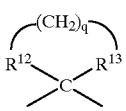
(c)

in which the groups (a) and (c) are as defined in the general formula (I) and in the group of (b'), E is a hydroxy group or the same as $R^{10}$ defined in the general formula (I) and $R^{11}$ is as defined in the general formula (I), used as a starting material in the above process for the production of the pyrazole derivative of the general formula (I) are novel compounds which no literature described, and are useful as intermediates for the production of the pyrazole derivatives of the present invention.

The aromatic carboxylic acid derivatives of the general formula (II) are acidic substances, and can be easily converted to salts by treating them with a base. These salts are also included in the aromatic carboxylic acid derivatives of the present invention. The above base can be selected from known bases without any limitation. For example, the base is selected from organic bases such as amines and anilines, and inorganic bases such as sodium compounds and potassium compounds. Examples of the amines include monoalkylamine, dialkylamine and trialkylamine. Alkyl groups of the alkylamines are generally $C_1$~$C_4$ alkyl groups. Examples of the anilines include aniline, monoalkylaniline and dialkylaniline. Alkyl groups of the alkylanilines are generally $C_1$~$C_4$ alkyl groups. Examples of the sodium compounds include sodium hydroxide and sodium carbonate. Examples of the potassium compounds include potassium hydroxide and potassium carbonate.

The aromatic carboxylic acid derivatives of the general formula (II) can be derived from carboxylic acids or esterification products of corresponding thiochroman-4-one (compound of the general formula (II) where Z' is a group (a) in which $R^9$ is an oxygen), compound (VI) in the following reaction scheme.

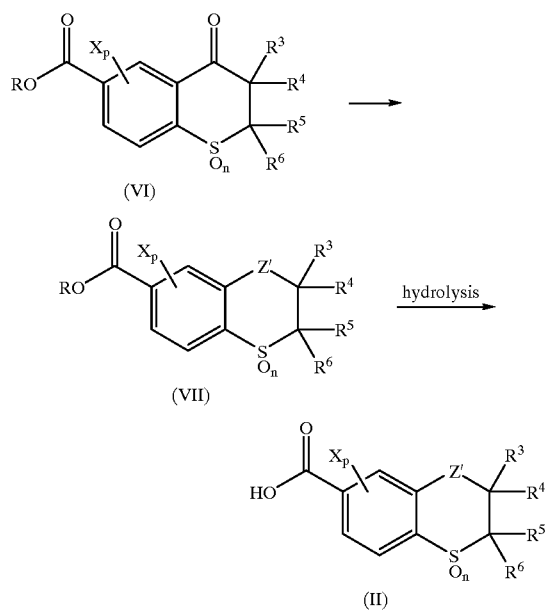

wherein R is a hydrogen atom or a $C_1$~$C_4$ alkyl group, and others are as defined already).

A compound of the general formula (VII) wherein Z' is a group (a) in which $R^9$ is a sulfur atom is obtained, for example, by reacting a sulfiding agent such as diphosphorus pentasulfide or a Lawesson's reagent with the compound (VI) in an inert solvent. The sulfiding agent is used in a molar amount equivalent to, or greater than, the molar amount of the compound (VI). The inert solvent is not specially limited so long as it is inert to the reaction, while an aromatic hydrocarbon such as toluene or xylene is preferred. The reaction temperature can be set in the range of from room temperature to the boiling point of a solvent, while the reaction temperature at or around the boiling point of the solvent is preferred.

A compound of the general formula (VII) wherein Z' is a group (b') in which each of E and $R^{11}$ is a $C_1$~$C_4$ alkoxy group is obtained, for example, by heating the compound (VI) in an excess amount of a $C_1$~$C_4$ alcohol in the presence of a strong acid. The acid is preferably selected from p-toluenesulfonic acid, sulfuric acid or hydrogen chloride. The amount of the acid per mole of the compound (VI) is preferably 0.05 to 2 mol.

A compound of the general formula (VII) in which Z' is a group of (c) in which each of $R^{12}$ and $R^{13}$ is an oxygen atom is obtained, for example, by heating the compound (VI) in an inert solvent in the presence of a corresponding $C_2$~$C_4$ dialcohol and a Lewis acid or a protic acid. Preferred as a Lewis acid is titanium tetrachloride, aluminum chloride or boron trifluoride etherate. Preferred as a protic acid is p-toluenesulfonic acid and methanesulfonic acid. Per mole of the compound (VI), the amount of the $C_2$~$C_4$ dialcohol is preferably 1 to 5 mol, and the amount of the acid is preferably 0.05 to 0.3 mol. The inert solvent is preferably selected from aromatic hydrocarbons such as toluene and xylene or halogen-containing solvents such as methylene chloride, 1,2-dichloroethane, chloroform and chlorobenzene. The reaction temperature is preferably a temperature at or around the boiling point of the solvent used.

The compound of the general formula (VII) can be also synthesized by replacing the acid with trimethylsilyl chloride in an amount of 2 mol per mole of the compound (VI) and carrying out the reaction without any solvent or in methylene chloride at room temperature.

A compound of the general formula (VII) wherein Z' is a group (b') in which each of E and $R^{11}$ is $C_1$~$C_4$ alkylthio is obtained, for example, by reacting the compound (VI) with corresponding $C_1$~$C_4$ alkylthiol and trimethylsilyl chloride. Preferably, the amount of each of the $C_1$~$C_4$ alkylthiol and the trimethylsilyl chloride per mole of the compound (VI) is at least 2 mol, and the reaction is carried out without any solvent or in methylene chloride at room temperature.

A compound of the general formula (VII) wherein Z' is a group (c) in which each of $R^{12}$ and $R^{13}$ is a sulfur atom is obtained, for example, by heating the compound (VI) in an inert solvent in the presence of a corresponding $C_2$~$C_4$ alkylene dithiol and a Lewis acid or a protonic acid. The Lewis acid is preferably selected from titanium tetrachloride, aluminum chloride or boron trifluoride etherate, and boron trifluoride etherate is particularly preferred. The protic acid is preferrably selected from p-toluenesulfonic acid or methanesulfonic acid. Per mole of the compound (VI), preferably, the amount of the $C_2$~$C_4$ alkylene dithiol is 1 to 5 mol, and the amount of the acid is 0.05 to 0.3 mol. The inert solvent is preferably selected from halogen-containing solvents such as methylene chloride, 1,2-dichloroethane, chloroform and chlorobenzene. The reaction temperature is preferably in the range of from room temperature to the boiling point of the solvent used.

When R of the compound (VII) is a $C_1$~$C_4$ alkyl group, the ester (VII) can be converted to the corresponding carboxylic acid derivative (II) by hydrolyzing the ester (VII) in the presence of an acid or a base. Further, a compound of the general formula (II) wherein Z' is a group (a) in which $R^9$ is an oxygen atom is obtained by hydrolyzing a corresponding ester of the compound (VI).

An aromatic carboxylic acid derivative of the general formula (VI) in which $R^3$, $R^4$, $R^5$ and $R^6$ are $R^{3'}$, $R^{4'}$, $R^{5'}$ and $R^{6'}$ (as defined already), as a starting material in the above reaction scheme, can be produced by various methods, and for example, it can be obtained through the following reaction routes (A~C).

Reaction Route A

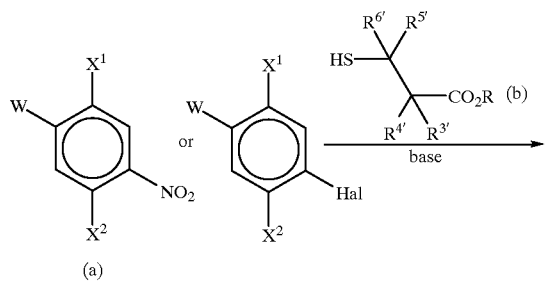

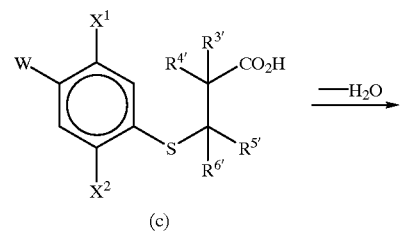

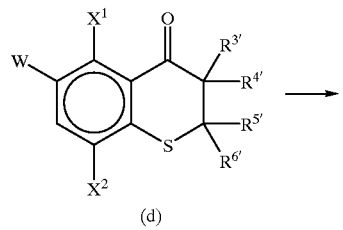

wherein Hal is a halogen, W is an acetyl, carboxyl or alkoxycarbonyl group, and $X^1$ and $X^2$ are substituents selected from substituents X defined in the pyrazole derivatives of the general formula (I).

Reaction Route B

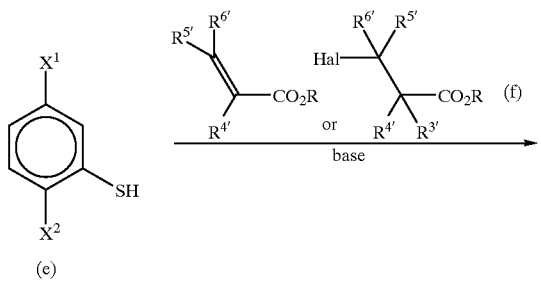

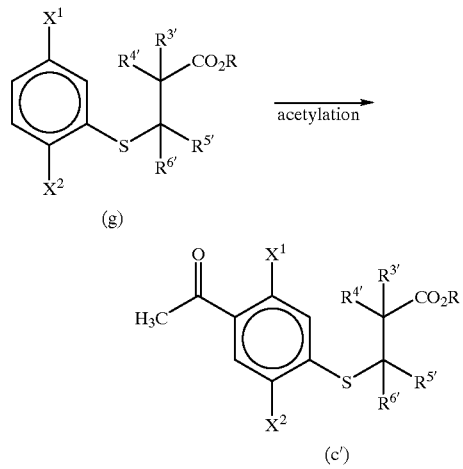

wherein Hal is halogen, R is hydrogen or a $C_1$~$C_4$ alkyl group, and $X^1$ and $X^2$ are as defined above.

Reaction Route C

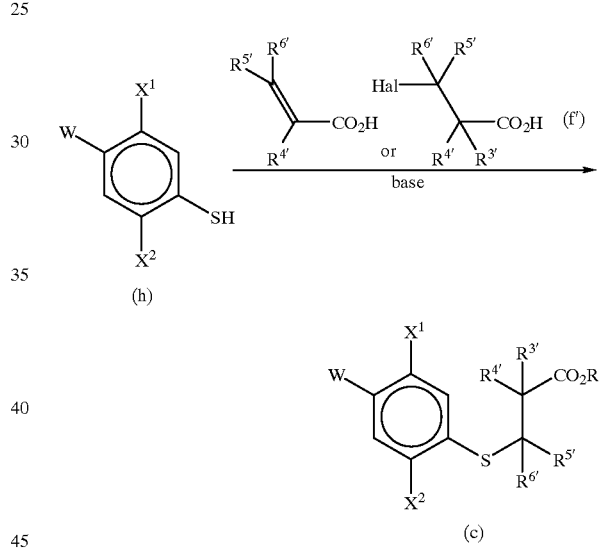

wherein Hal is halogen, W is an acetyl, carbonyl or alkoxycarbonyl group, and $X^1$ and $X^2$ are as defined above.

Each route will be outlined below.

Reaction Route A

Compound (a) and Compound (b) are heated at a temperature in the range of from 50 to 130° C. in an inert solvent [DMF (N,N-dimethylformamide) or acetonitrile] in the presence of a base (potassium carbonate or sodium carbonate), to obtain a sulfide (c). The amount of the base per normality of Compound (a) is preferably 2 to 6 N.

The sulfide (c) is stirred together with a dehydrating agent (polyphosphoric acid, concentrated sulfuric acid, fuming sulfuric acid or phosphorus pentachloride) at a temperature range of from 0 to 130° C., to obtain a thiochroman (d). An excess amount of the dehydrating agent may be used to work it as a solvent as well. Methylene chloride, 1,2-dichloroethane or toluene may be used as a solvent.

In another method, Compound (c) is reacted with a halogenating agent (thionyl chloride, phosphorus oxychloride or phosphorus tribromide) to convert it to a corresponding acid halide, and the acid halide is reacted with a Lewis acid (aluminum chloride, boron trifluoride etherate or a sulfonic acid-based carion exchange resin) in a dehydrohalogenation reaction in an inert solvent, whereby the thiochroman (d) can be obtained.

When substituent W on the 6-position of thiochroman (d) is an acetyl group

The sulfur atom of Compound (d) is oxidized to convert a sulfone, and then the sulfone is subjected to a haloform reaction, whereby the carboxylic acid derivative (IIa) can be obtained. In this case, Compound (IIa) is structurally limited to n=2, i.e., a sulfone.

In the oxidation of the sulfur atom, for example, Compound (d) is heated in an aqueous solution of hydrogen peroxide and acetic acid to obtain the corresponding sulfone. The hydrogen peroxide is used in a molar amount of at least 2 mol per mole of Compound (d).

In another method, Compound (IIa) is also obtained by reacting Compound (d) with m-CPBA (m-chloroperbenzoic acid) in a molar amount of at least 2 mol per mole of Compound (d) in an inert solvent.

The haloform reaction method includes a method (i) in which chlorine or bromine (at least 3 times by molar amount) is added to the sulfone in a basic aqueous solution such as sodium hydroxide (at least 4 times by molar amount) and the resultant mixture is stirred at a temperature of from room temperature to 80° C., and a method (ii) in which the sulfone is stirred in an aqueous solution of hypochlorite (at least 3 times by molar amount) at a temperature of from 10 to 30° C.

In any method, the reaction is smoothly proceeded with by adding a hydrophilic organic solvent such as dioxane to the system.

When substituent W on the 6-position of thiochroman (d) is an alkoxycarbonyl group A carboxylic acid ester of Compound (d) is hydrolyzed by a conventional method, whereby the carboxylic acid derivative (IIa) can be obtained.

A compound of the general formula (IIa) in which a substituent X on the benzene ring is substituted only on the 5-position of the thiochroman can be obtained by synthesizing a thiochroman derivative (d) in which $X^2$ is a chlorine atom, then oxidizing the sulfur atom to convert the thiochroman derivative (d) to a sulfone, and hydrogenating the 8-position of the thiochroman by reductive cleavage. The method of obtaining the sulfone by oxidizing the sulfur atom of the compound (d) is as explained above.

In the hydrogenation by reductive cleavage, for example, the sulfone is subjected to reductive cleavage in an inert solvent (ethanol, ethyl acetate or tetrahydrofuran) in the presence of a catalytic hydrogenation catalyst (palladium carbon, Raney nickel or platinum dioxide) under a hydrogen atmosphere, whereby a thiochroman in which hydrogen is substituted on the 8-position can be obtained. In this case, preferably, the hydrogen pressure is 1 atm to 80 kg/cm$^2$, and the reaction temperature is room temperature to 100° C. Further, the reaction proceeds more smoothly in the co-presence of a base (an organic base such as pyridine or triethylamine, or an inorganic base such as sodium hydroxide or potassium carbonate, or a salt such a s sodium acetate) in an amount of at least 1 N per normality of the substrate.

Reaction Route B

Compound (e) and Compound (f) are allowed to react in an inert solvent (not specially limited so long as it is inert to the reaction) in the presence of a base (an organic base such as pyridine or triethylamine, or an inorganic base such as sodium hydroxide or potassium carbonate) at a temperature in the range of from room temperature to the boiling point of the solvent, to obtain a sulfide (g). When Compound (f) in the above reaction is an acrylic acid derivative, $R^{3'}$ in the product is hydrogen. When Compound (f) is an acrylic acid derivative, the reaction proceeds even without any solvent. The amount of the base per normality of Compound (e) is preferably 0.1 N to 1 N. When Compound (f) is a β-halopropionic acid derivative, the amount of the base per normality of Compound (e) is preferably 1 to 3 N.

When R in Compound (g) is hydrogen, Compound (g) is esterified according to a conventional method, and then, the ester is reacted with an acetylation source such as acetyl chloride and a Lewis acid (aluminum chloride) in an inert solvent (methylene chloride, 1,2-dichloroethane or chlorobenzene), to obtain Compound (c'). The amount of each of the acetylation source and the Lewis acid per mole of the ester is preferably at least 1 mol. The reaction temperature is preferably −10 to 20° C.

The ester (c') obtained in the above reaction is hydrolyzed to a carboxylic acid (c) according to a conventional method, and then, the method explained in Reaction route A can be applied to synthesize the carboxylic acid derivative (IIa).

Reaction Route C

This reaction uses Compound (h) having a group W containing a carbonyl group in place of the starting material (e) in Reaction route B. Compound (h) as a starting material is obtained, for example, by reacting sodium hydrosulfide with Compound (a).

Compound (h) and acid Compound (f') are allowed to react according to the method described in Reaction route B, to form a sulfide (c). When β-halopropionic acid is used as a raw material (f'), the amount of the base per normality of Compound (h) is at least 2 N.

The method described in Reaction route A can be applied to the above-obtained sulfide (c) to product a carboxylic acid derivative (IIa).

Of the compounds of the general formula (VI), a carboxylic acid ester compound of the general formula (VIc),

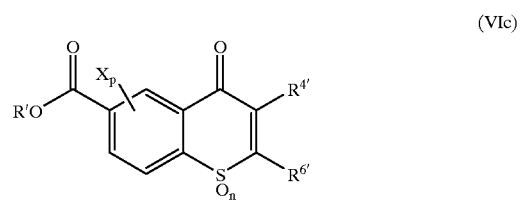

(VIc)

wherein $R^{4'}$, $R^{6'}$, X, n and p are as defined already and R' is a $C_1$~$C_4$ alkyl group,
can be derived, for example, by the following method.

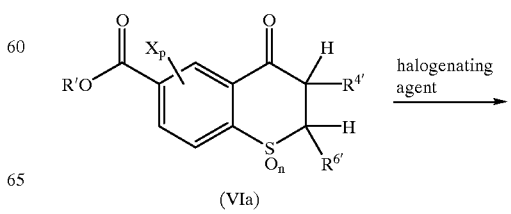

(VIa)

-continued

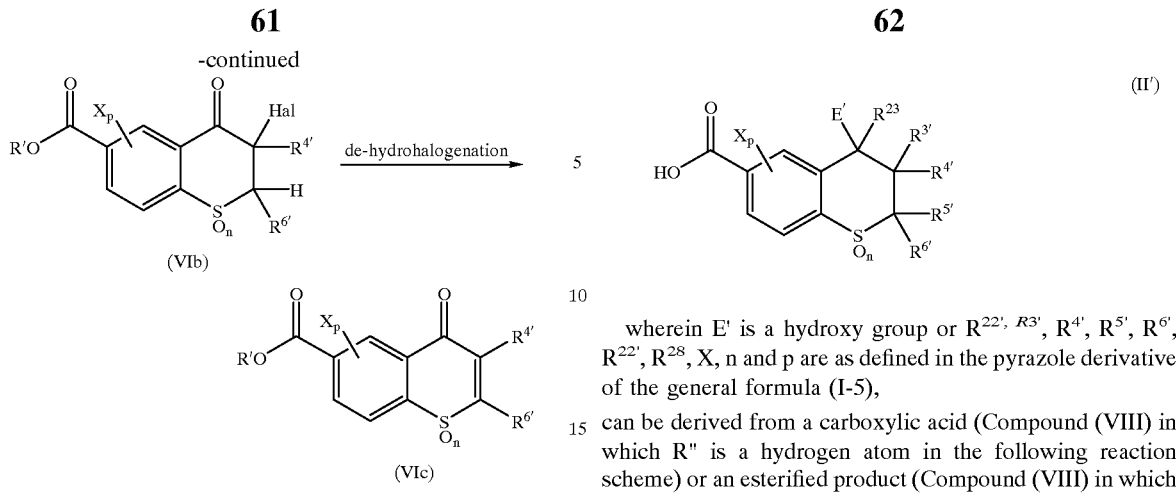

(VIb)

(VIc)

A carboxylic acid ester of the general formula (VIa) is reacted, for example, with a halogenating agent such as bromine, iodine or N-chlorosuccinimide (NCS), whereby a thiochroman-3-monohalogenated compound (VIb) is obtained. This reaction can be carried out in a reaction solvent selected from halogen-containing solvents such as carbon tetrachloride and methylene chloride or alcohol solvents such as methanol or ethanol, and the reaction temperature can be set in the range of from 0° C. to the reflux temperature of the solvent used.

Then, Compound (VIb) is reacted with a base selected from organic bases such as pyridine and trimethylamine or inorganic bases such as potassium carbonate, sodium carbonate, sodium acetate and potassium hydroxide in an amount equivalent to, or greater than, that of Compound (VIb) by equivalent weight, whereby a carboxylic acid ester compound of the general formula (VIc) can be obtained. The solvent used in this reaction is not specially limited so long as it is inert to the reaction, or as a solvent, the above organic base may be used in an excess amount. The reaction temperature can be set in the range of from room temperature to the reflux temperature of the solvent.

Further, in the aromatic carboxylic acid derivatives of the general formula (II), an aromatic carboxylic acid derivative of the general formula (II'), (II')

wherein E' is a hydroxy group or $R^{22'}$, $R^{3'}$, $R^{4'}$, $R^{5'}$, $R^{6'}$, $R^{22'}$, $R^{28}$, X, n and p are as defined in the pyrazole derivative of the general formula (I-5), can be derived from a carboxylic acid (Compound (VIII) in which R" is a hydrogen atom in the following reaction scheme) or an esterified product (Compound (VIII) in which R" is an alkyl group in the following reaction scheme) of a corresponding 4-hydroxythiochroman (when E' in the general formula (II') is a hydroxy group, Compound (VIII) in the following reaction scheme). Further, it can be derived from Compound of the general formula (X) as a raw material. Further, the aromatic carboxylic acid of the general formula (X) can be similarly derived from a carboxylic acid or an esterified product (Compound (VIII) in the following) of 4-hydroxythiochroman.

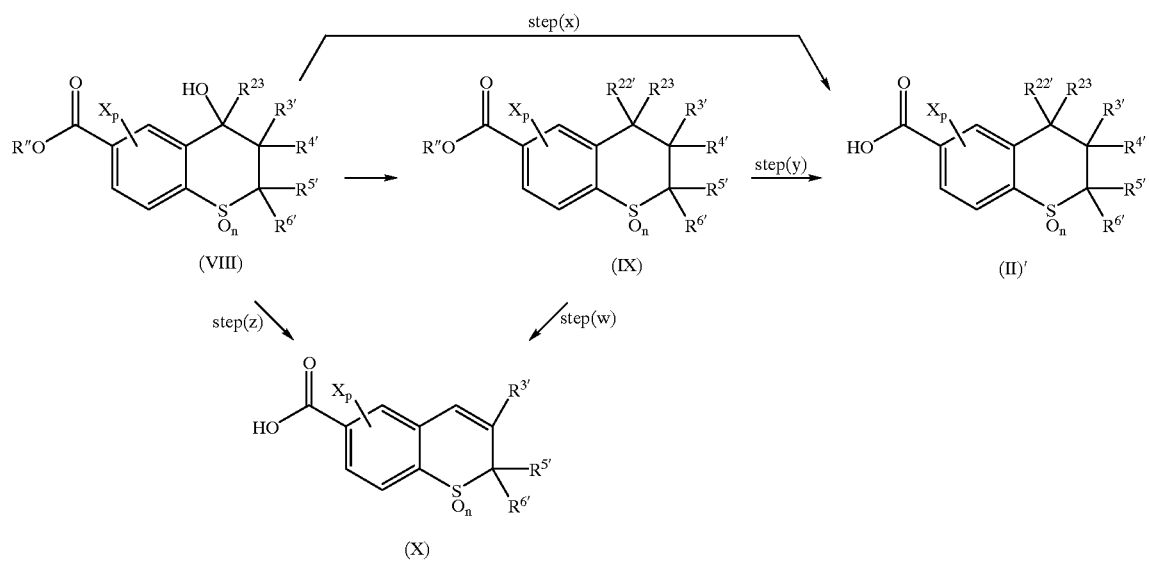

In the above reaction scheme, R" is a hydrogen atom, a $C_1$~$C_4$ alkyl group or a group of

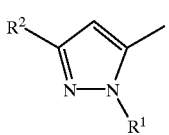

wherein $R^1$ and $R^2$ are as defined already.

In the above reaction scheme, when R" is a pyrazolyl group as above, the pyrazole derivative (Ia) can be obtained by a rearrangement reaction, not through Compound (II'), but according to the method explained already (see Step 1-b described already).

The aromatic carboxylic acid derivative of the general formula (II') in which E' is a halogen atom can be obtained by reacting the 4-hydroxythiochroman derivative (VIII), for example, with an acid chloride of an inorganic acid such as thionyl chloride, phosphorus trichloride or phosphorus tribromide, a hydrohalogenic acid such as hydrobromic acid or a halogenating agent such as triphenylphosphine/carbon tetrachloride in an inert solvent (see the above step (x)). The halogenating agent is used in an amount equivalent to, or greater than, the molar amount of of Compound (VIII). When the halogenating agent is in the form of a liquid, such as thionyl chloride, it may be also used as a solvent. The inert solvent is not specially limited so long as it is inert to the reaction, while a halogen-containing solvent such as methylene chloride, chloroform or dichloroethane is preferred. The reaction temperature can be set in the range of from −20° C. to the boiling point of the solvent used, while it is preferably from room temperature to about 100° C.

The aromatic carboxylic acid derivative of the general formula (II') in which E' is an alkylthio group can be synthesized by reacting Compound (IX) in which $R^{22'}$ is a halogen atom or a so-called "good leaving group" such as a methanesulfonyloxy, p-toluenesulfonyloxy or trifluoromethanesulfonyloxy group with a $C_1$~$C_4$ alkylthiol in the presence of a base (see the above step (y)). The amount of the alkylthiol per mole of Compound (IX) is preferably 1 to 10 mol. The base can be selected from inorganic bases such as potassium carbonate and sodium carbonate or alkoxides such as sodium ethoxide, sodium methoxide and potassium t-butoxide. The solvent can be selected from aprotic polar solvents such as dimethylformamide and dimethylsulfoxide or alcohols such as methanol and ethanol. The reaction temperature can be set in the range of from room temperature to the boiling point of the solvent used, while it is preferably from room temperature to 100° C.

The aromatic carboxylic acid derivative of the general formula (II') in which E' is a $C_1$~$C_4$ mono- or di-alkyl amino group can be synthesized by similarly reacting Compound (IX) in which $R^{22'}$ is a halogen atom or a so-called "good leaving group" such as a methanesulfonyloxy, p-toluenesulfonyloxy or trifluoromethanesulfonyloxy group with a $C_1$~$C_4$ mono- or di-alkyl amino in the presence of a base (see the above step (y)). The amount of the amine per mole of Compound (IX) is preferably 1 to 10 mol. An excess amount of the amine also works as a base, and it is therefore not necessary to newly add a base. When the base is used, it is preferred to use an inorganic base such as sodium carbonate or potassium carbonate in an amount of at least 1 to 10 N per normality of Compound (IX). The solvent is preferably selected from alcohols such as methanol, ethanol and ethylene glycol, aprotic polar solvents such as N,N-dimethylformamide and dimethylsulfoxide or ketones such as acetone and methyl ethyl ketone. The reaction temperature can be set in the range of from room temperature to the boiling point of the solvent used, while it is preferably from room temperature to 100° C.

The aromatic carboxylic acid derivative of the general formula (II') in which E' and $R^{3'}$ form a bonding [Compound (X) in the above scheme] can be synthesized from a 4-hydroxythiochroman derivative (VIII) as a starting material in the presence of an inert solvent and a catalyst selected from mineral acids such as sulfuric acid or organic acids such as p-toluenesulfonic acid (see the above step (z)). The inert solvent is not specially limited so long as it is inert to the reaction. It is preferred to select the inert solvent from aromatic solvents such as benzene, toluene and xylene or halogen-containing solvents such as chloroform, since formed water can be azeotropically removed with the solvent so that the yield improves. The reaction temperature can be set in the range of from room temperature to the boiling point of the solvent used.

The aromatic carboxylic acid derivative of the general formula (II') in which each of $R^{22'}$ and $R^{3'}$ is a halogen atom can be synthesized by adding a halogen such as chlorine, bromine or iodine to the above-obtained aromatic carboxylic acid (X) (see the above step (w)). The solvent is not specially limited so long as it is inert to the reaction, while it is preferably selected from halogen-containing solvents such as dichloromethane, chloroform and dichloroethane. Further, sulfuryl chloride, or the like may be used to generate chlorine in the system, and the chlorine can be directly allowed to react. The reaction temperature can be set in the range of from −20° C. to the boiling point of the solvent used.

The hydroxythiochroman used as a starting material in the above reaction scheme can be produced by various methods. For example, Compound (IIa) is obtained through the above Reaction route A, through a combination of Reaction routes A and B, or through a combination of Reaction routes C and A, and then converted to the hydroxythiochroman (IIb).

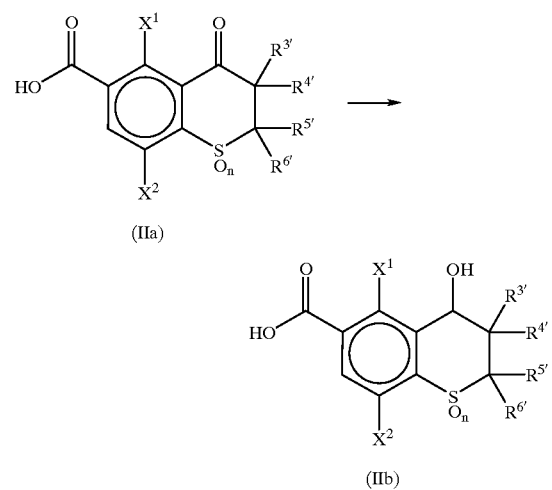

(IIa)

(IIb)

Compound (IIb) can be synthesized by reducing the ketonic carbonyl group of Compound (IIa). The reducing agent can be selected from sodium borohydride or a zinc powder. When sodium borohydride is used, the reaction can be carried out in an alcohol solvent such as methanol, ethanol or propanol in the presence of the reducing agent in an amount of 1 to 5 N per normality of Compound (IIa). The reaction temperature can be set in the range of from room temperature to the boiling point of the solvent used, while it is preferably from room temperature to 80° C. When a zinc powder is used as a reducing agent, it is preferable to add an aqueous solution of sodium hydroxide whose amount is 3 to 10 times by equivalent weight to an alcohol solvent such as methanol, ethanol or propanol and use a zinc powder whose equivalent weight is 1 to 5 times that of the raw material. The reaction temperature can be set in the range of from room temperature to the boiling point of the solvent used, while it is preferably 40 to 80° C.

The present invention will be explained with reference to Preparation Examples and Herbicide Examples hereinafter, while the present invention shall not be limited by these Examples.

SYNTHESIS OF INTERMEDIATES, 6-carboxythiochromans

Preparation Example 1

6-Carboxy-3,3,5,8-tetramethylthiochroman-4-one-1,1-dioxide 1-1) Synthesis of 3-(2,5-dimethylphenylthio)pivalic Acid A 100-ml round-bottomed flask was charged with 1.38 g (10.00 mmol) of 2,5-dimethylthiophenol, 1.40 g (10.26 mmol) of 3-chloropivalic acid and 15 ml of acetone. Then, 2.07 g (15.0 mmol) of potassium carbonate was added, and the mixture was refluxed under heat for 30 minutes. The reaction mixture was allowed to cool to room temperature, and then about 100 ml of water was added. An aqueous layer was washed with n-hexane once, and neutralized and acidified with a 5 wt % hydrochloric acid aqueous solution. A precipitated solid was extracted with ethyl acetate, and an organic layer was washed with diluted hydrochloric acid and with a saturated sodium chloride aqueous solution and dried over anhydrous sodium sulfate. The solvent was distilled off under reduced pressure to give 1.90 g (yield 80%) of 3-(2,5-dimethylphenylthio)pivalate.

$^1$H-NMR ppm (CDCl$_3$, TMS): δ 1.33(6H,s), 2.29(3H,s), 2.36(3H,s), 3.12(2H,s), 6.84–7.18(3H,m)

1-2) Synthesis of methyl 3-(2,5-dimethylphenylthio)pivalate 1.88 Grams (7.90 mmol) of 2-(2,5-dimethylphenylthio)pivalic acid was dissolved in 20 ml of dry methanol in a 100-ml round-bottomed flask. Then, 0.5 ml of concentrated sulfuric acid was added, and the mixture was refluxed under heat for 5 hours. The reaction mixture was allowed to cool to room temperature, and extracted with chloroform. An organic layer was washed with a saturated sodium hydrogencarbonate aqueous solution and with saturated sodium chloride aqueous solution and dried over anhydrous sodium sulfate. The solvent was distilled off under reduced pressure to give 1.92 g (yield 96%) of methyl 3-(2,5-dimethylphenylthio)pivalate.

$^1$H-NMR ppm (CDCl$_3$, TMS): δ 1.30(6H,s), 2.29(3H,s), 2.33(3H,s), 3.11(2H,s), 3.58(3H,s), 6.85–7.17(3H,m)

1-3) Synthesis of 3-(4-acetyl-2,5-dimethylphenylthio)pivalic acid 1.34 Grams (10.04 mmol) of aluminum chloride was added to a solution of 0.86 g (10.96 mmol) in 10 ml of methylene chloride in a 50-ml three-necked round-bottomed flask under 0° C. and the mixture was stirred at the same temperature for 30 minutes. Then, a solution of 1.20 g (1.76 mmol) of methyl 3-(2,5-dimethylphenylthio)pivalate in 6 ml of methylene chloride was added, and the mixture was stirred under 0° C. for 3 hours. The reaction mixture was poured into about 100 ml of ice water and extracted with methylene chloride, and an organic layer was washed with 1 wt % hydrochloric acid, with water and with a saturated sodium chloride aqueous solution. The solvent was distilled off, the resulting oily residue was dissolved in about 10 ml of methanol, and 0.54 g (9.62 mmol) of potassium hydroxide and 3 ml of water were added. The mixture was refluxed under heat for 1 hour. The solvent was distilled off under reduced pressure, and to the residue was added 50 ml of water. The mixture was neutralized and acidified with the aqueous solution containing 5 wt % hydrochloric acid. A precipitated solid was extracted with ethyl acetate, and an organic layer was washed with a saturated sodium chloride aqueous solution and dried over anhydrous sodium sulfate. The solvent was distilled off to give 1.34 g (yield 100%) of 3-(4-acetyl-2,5-dimethylphenylthio)pivalic acid.

$^1$H-NMR ppm (CDCl$_3$, TMS): δ 1.37(6H,s), 2.35(3H,s), 2.51(3H,s), 2.54(2H,s), 3.22(2H,s), 7.11(1H,s), 7.48(1H,s)

1-4) Synthesis of 6-acetyl-3,3,5,8-tetramethylthiochroman-4-one 1.34 Grams (4.79 mmol) of 3-(4-acetyl)-2,5-dimethylphenylthio)pivalic acid was added to about 7 g of polyphosphoric acid (containing 20 wt % diphosphorus pentoxide) in a 50-ml beaker, and the mixture was vigorously mixed and stirred at 60° C. for 1 hour. To the reaction mixture was added about 50 g of ice water, the mixture was vigorously stirred, and an organic substance was extracted with ethyl acetate. An organic layer was washed with water, with a saturated sodium hydrogencarbonate aqueous solution and with a saturated sodium chloride aqueous solution, and dried over anhydrous sodium sulfate. Then, the solvent was distilled off under reduced pressure to give 1.20 g (yield 96%) of 6-acetyl-3,3,5,8-tetramethylthiochroman-4-one.

$^1$H-NMR ppm (CDCl$_3$, TMS): δ 1.32(6H,s), 2.30(3H,s), 2.47(3H,s), 2.53(3H,s), 3.06(2H,s), 7.30(1H,s)

1-5) Synthesis of 6-acetyl-3,3,5,8-tetramethylthiochroman-4-one-1,1,-dioxide

A 100-ml round-bottomed flask was charged with 1.18 g (4.50 mmol) of 6-acetyl-3,3,5,8-tetramethylthiochroman-4-one, 2 ml of acetic acid and 1.12 g (9.88 mmol) of a 30 wt % hydrogen peroxide aqueous solution, and the mixture was allowed to react at 80° C. for 2 and half hours. The reaction mixture was diluted with about 30 ml of water, and a sodium hydrogensulfite aqueous solution was added to decompose excess peroxide. Then, the mixture was extracted with ethyl acetate. An organic layer was washed with a saturated sodium hydrogencarbonate aqueous solution and with a saturated sodium chloride aqueous solution and dried over anhydrous sodium sulfate, and the solvent was distilled off under reduced pressure to give 1.28 g (yield 97%) of 6-acetyl-3,3,5,8-tetramethylthiochroman-4-one-1,1-dioxide.

$^1$H-NMR ppm (CDCl$_3$, TMS): δ 1.45(6H,s), 2.38(3H,s), 2.57(3H,s), 2.74(3H,s), 3.51(2H,s), 7.39(1H,s)

1-6) Synthesis of 6-carboxy-3,3,5,8-tetramethylthiochroman-4-one-1,1-dioxide 17.8 Grams (about 15 mmol) of a 6.4 wt % sodium hypochlorite aqueous solution was placed in a 100-ml three-necked round-bottomed flask, and cooled to 15~20° C., and then a solution of 1.26 g (4.26 mmol) of 6-acetyl-3,3,5,8-tetramethylthiochroman-4-one-1,1-dioxide in 8 ml of dioxane was gradually added. The mixture was stirred at 15~20° C. with external cooling for 30 minutes, and then stirred at room temperature (temperature-increased to about 30° C.) for 3 hours. The reaction mixture was diluted with about 50 ml of water and washed with chloroform twice. A sodium sulfate aqueous solution was added to an aqueous layer to decompose excess hypochlorite, and then the aqueous solution was neutralized and acidified with a 5 wt % hydrochloric acid aqueous solution to give a white solid. The solid was extracted with ethyl acetate, and an organic layer was washed with diluted hydrochloric acid and with a saturated sodium chloride aqueous solution and dried over anhydrous sodium sulfate. The solvent was distilled off under reduced pressure to give 1.06 g (yield 84%) of 6-carboxy-3,3,5,8-tetramethylthiochroman-4-one-1,1-dioxide in the form of a white solid.

$^1$H-NMR ppm (CDCl$_3$, TMS): δ 1.47(6H,s), 2.58(3H,s), 2.76(3H,s), 3.53(2H,s), 7.93(1H,s)

Preparation Example 2

6-Carboxy-3,3,5-trimethylthiochroman-4-one-1,1-dioxide 2-1) Synthesis of 3-(4-acetyl-2-chloro-5-methylphenylthio)pivalic acid A 100-ml three-necked round-bottomed flask was charged with 2.98 g (14.65 mmol) of 2-acetyl-4,5-dichlorotoluene, 1.72 g (12.84 mmol) of 3-mercaptopivalic acid and 15 ml of N,N-dimethylformamide under nitrogen atmosphere. Then, 3.04 g (22.00 mmol) of potassium carbonate was added. The reaction mixture was heated at 100~110° C. for 6 hours under nitrogen atmosphere. The reaction mixture was allowed to cool to room temperature, and about 150 ml of water was added. The mixture was washed with chloroform twice, and an aqueous layer was neutralized and acidified with a 5 wt % hydrochloric acid aqueous solution. A precipitated gummy substance was extracted with ethyl acetate, and an organic layer was washed with a 1 wt % hydrochloric acid aqueous solution, with water and with a saturated sodium chloride aqueous solution and dried over anhydrous sodium sulfate. Then, the solvent was distilled off under reduced pressure to give 3.02 g (yield 78%) of 3-(4-acetyl-2-chloro-methylphenylthio)pivalic acid.

$^1$H-NMR ppm (acetone-$d_6$, TMS): δ 1.37(6H,s), 2.49(3H, s), 2.56(3H,s), 3.36(2H,s), 7.38(1H,s), 7.83(1H,s)

2-2) Synthesis of 6-acetyl-8-chloro-3,3,5-trimethylthiochroman-4-one 3.00 Grams (9.98 mmol) of 3-(4-acetyl-2-chloro-5-methylphenylthio)pivalic acid was added to about 20 g of polyphosphoric acid (containing 20 wt % diphosphorus pentoxide) in a 50-ml beaker, and the mixture was vigorously mixed and stirred at 90° C. for 2.5 hours. About 100 g of ice water was poured into the reaction mixture, and the mixture was vigorously stirred. An organic substance was extracted with ethyl acetate. An organic layer was washed with water, with a saturated sodium hydrogencarbonate aqueous solution and with a saturated sodium chloride aqueous solution, and dried over anhydrous sodium sulfate. The solvent was distilled off under reduced pressure to give 2.21 g (yield 78%) of 6-acetyl-8-chloro-3,3,5-trimethylthiochroman-4-one.

$^1$H-NMR ppm (CDCl$_3$, TMS): δ 1.33(6H,s), 2.46(3H,s), 2.53(3H,s), 3.10(2H,s), 7.51(1H,s)

2-3) Synthesis of 6-acetyl-8-chloro-3,3,5-trimethylthiochroman-4-one-1,1-dioxide 4 Milliliters of acetic acid and 2.12 g (18.71 mmol) of a 30 wt % hydrogen peroxide aqueous solution were added to 2.20 g (7.79 mmol) of 6-acetyl-8-chloro-3,3,5-trimethylthiochroman-4-one in a 100-ml round-bottomed flask, and the mixture was reached at 80° C. for 2.5 hours. The reaction mixture was diluted with about 50 ml of water, and a sodium hydrogensulfite aqueous solution was added to decompose excess hydrogen peroxide. Then, the reaction mixture was extracted with ethyl acetate. An organic layer was washed with a saturated sodium hydrogencarbonate aqueous solution and with a saturated sodium chloride aqueous solution, and dried over anhydrous sodium sulfate, and the solvent was distilled off under reduced pressure to give 2.16 g (yield 88%) of 6-acetyl-8-chloro-3,3,5-trimethylthiochroman-4-one-1,1-dioxide.

$^1$H-NMR ppm (CDCl$_3$, TMS): δ 1.46(6H,s), 2.40(3H,s), 2.58(3H,s), 3.58(2H,s), 7.62(1H,s)

2-4) Synthesis of 6-acetyl-3,3,5-trimethylthiochroman-4-one-1,1-dioxide

A 30-ml SUS autoclave was charged with 1.00 g (3.18 mmol) of 6-acetyl-8-chloro-3,3,5-triemthylthiochroman-4-one-1,1-dioxide, 0.25 g of 5 wt % Pd/activated carbon, 12 ml of tetrahydrofuran and 0.26 g (3.29 mmol) of pyridine, and hydrogen gas was substituted for atmosphere in the autoclave. Then, the autoclave was pressure-increased up to a hydrogen pressure of 8.0 kg/cm$^2$. While the mixture was stirred at room temperature, each time when the pressure decreased to 6.0 kg/cm$^2$, hydrogen gas was additionally charged to maintain the pressure at 6~8 kg/cm$^2$. It took about 10 hours before no pressure decrease was found. Nitrogen gas was substituted for atmosphere in the reaction system, and then the pressure was released. The Pd/activated carbon was removed by filtration, and the tetrahydrofuran was distilled off under reduced pressure. The residue was extracted with ethyl acetate, an organic layer was washed with diluted hydrochloric acid, with a saturated sodium hydrogencarbonate aqueous solution and with a saturated sodium chloride aqueous solution, and dried over anhydrous sodium sulfate, and the solvent was distilled off under reduced pressure to give 0.84 g (yield 94%) of 6-acetyl-3,3,5-trimethylthiochroman-4-one-1,1-dioxide.

$^1$H-NMR ppm (CDCl$_3$, TMS): δ 1.48(6H,s), 2.49(3H,s), 2.58(3H,s), 3.45(2H,s), 7.63–7.72(1H,ABq), 7.83–7.92(1H, ABq)

2-5) Synthesis of 6-carboxy-3,3,5-trimethylthiochroman-4-one-1,1-dioxide 11.6 Grams (about 9.8 mmol) of a 6.3 wt % sodium hypochlorite aqueous solution was placed in a 50-ml three-necked round-bottomed flask, and cooled to 15~20° C., and then a solution of 0.83 g (2.96 mmol) of 6-acetyl-3,3,5-trimethylthiochroman-4-one-1,1-dioxide in 5 ml of dioxane was gradually added. The mixture was stirred at 15~20° C. for 30 minutes, and then stirred at room temperature (temperature-increased to 28° C.) for 3 hours, and the reaction mixture was diluted with about 50 ml of water and washed with chloroform twice. A sodium sulfite aqueous solution was added to an aqueous layer to decompose excess hypochlorite, and then the mixture was neutralized and acidified with a 5 wt % hydrochloric acid aqueous solution to give a white solid. The solid was extracted with ethyl acetate, and an organic layer was washed with a saturated sodium chloride aqueous solution and dried over anhydrous sodium sulfate. Then, the solvent was distilled off under reduced pressure, to give 0.68 g (yield 81%) of 6-carboxy-3,3,5-trimethylthiochroman-4-one-1,1-dioxide in the form of a white solid.

$^1$H-NMR ppm (acetone-$d_6$, TMS): δ 1.48(6H,s), 2.58(3H, s), 3.75(2H,s), 7.80–7.89(1H,ABq), 8.11–8.20(1H, ABq)

Preparation Example 3

6-Carboxy-8-chloro-5-methylthiochroman-4-one 3-1) Synthesis of 3-(2-chloro-4-ethoxycarbonyl-5-methylphenylthio)propionic acid 23.4 Milliliters (1.1 eq., 268 mmol) of 3-mercaptoproionic acid was added to a solution containing 53.7 g (231 mmol) of ethyl 4,5-dichloro-o-toluylate, 37.0 g (1.1. eq., 268 mmol) of potassium carbonate and 215 ml of DMF at room temperature, and the mixture was stirred under heat at 120~125° C. for 2 hours and 20 minutes. The reaction mixture was cooled to about 50° C., and ethyl acetate and water were added. The mixture was washed with ethyl acetate four times, and washed with hexane once, for removing DMF and a neutral component. Concentrated hydrochloric acid was added to an aqueous layer to precipitate a crystal, and the mixture was allowed to stand for a while. Then, the crystal was collected by filtration and washed with water three times. The crystal was dissolved in ethyl acetate, washed with a saturated sodium chloride aqueous solution and then dried over anhydrous sodium sulfate. The solvent was distilled off under reduced pressure to give 50.4 g (yield 60%) of 3-(2-chloro-4-ethoxycarbonyl-5-methylphenylthio)propionic acid.

$^1$H-NMR ppm (CDCl$_3$, TMS): δ 1.39(3H,t), 2.58(3H,s), 2.91(2H,t), 3.26(2H,t), 4.34(2H,q), 7.08(1H,s), 7.92(1H,s)

3-2) Synthesis of 8-chloro-6-ethoxycarbonyl-5-methylthiochroman-4-one 47.7 Grams (157 mmol) of 3-(2-chloro-4-ethoxycarbonyl-5-methylphenylthio)propionic acid was added to 167 g of 20 wt % P$_2$O$_5$-containing polyphosphoric acid heated at 80~85° C., and then the mixture was stirred under heat for 1 hour and 20 minutes. After allowed to cool to room temperature, the reaction mixture was gradually added to a mixture of 191 g (1.80 mol) of sodium carbonate and ice, and the mixture was stirred at room temperature until the sodium carbonate was almost dissolved. The mixture was extracted with ethyl acetate twice, and the extract was washed with a sodium carbonate aqueous solution twice, with water twice and with a saturated sodium chloride aqueous solution once, and dried over anhydrous sodium sulfate. The solvent was distilled off under reduced pressure to give 41.3 g (yield 85%) of 8-chloro-6-ethoxycarbonyl-5-methylthiochroman-4-one.

$^1$H-NMR ppm (CDCl$_3$, TMS): δ 1.37(3H,t), 2.58(3H,s), 2.9–3.1(2H,m), 3.3–3.5(2H,m), 4.34(2H,q), 7.81(1H,s)

3-3) Synthesis of 6-carboxy-8-chloro-5-methylthiochroman-4-one 2.0 Grams (7.0 mmol) of 8-chloro-6-ethoxycarbonyl-5-methylthiochroman-4-one was dissolved in 10 ml of acetic acid, and 10 ml of a 4N hydrochloric acid aqueous solution was added. The mixture was refluxed under heat for 5 hours. After allowed to cool to room temperature, the reaction mixture was diluted with about 100 ml of water, and a precipitated solid was extracted with ethyl acetate. A carboxylic acid component was extracted from an organic layer with a saturated sodium hydrogencarbonate aqueous solution, and an aqueous layer was neutralized and acidified with a 5 wt % hydrochloric acid aqueous solution. A precipitated solid was extracted with ethyl acetate, and an organic layer was washed with a saturated sodium chloride aqueous solution and dried over anhydrous sodium sulfate. The solvent was distilled off to give 1.6 g (yield 90%) of 6-carboxy-8-chloro-5-methylthiochroman-4-one in the form of a white solid.

m.p.: 190.0~191.8° C. $^1$H-NMR ppm (acetone-d$_6$, TMS): δ 2.63(3H,s), 3.01–3.11(2H,m), 3.31–3.42(2H,m), 7.90(1H, s)

Preparation Example 4

6-Carboxy-8-chloro-4,4-ethylenedioxy-5-methylthiochroman-1,1-dioxide 4-1) Synthesis of 8-chloro-6-ethoxycarbonyl-5-methylthiochroman-4-one-1,1-dioxide 3 Milliliters of acetic acid and 1.75 g (15.47 mmol) of a 30 wt % hydrogen peroxide aqueous solution were added to 2.00 g (7.03 mmol) of 8-chloro-6-ethoxycarbonyl-5-methylthiochroman-4-one in a 50-ml round-bottomed flask, and the mixture was allowed to react at 70° C. for 2 hours. The reaction mixture was diluted with about 50 ml of water, and a sodium hydrogensulfite was added to decompose excess hydrogen peroxide. Then, the mixture was extracted with ethyl acetate. An organic layer was washed with a saturated sodium hydrogencarbonate aqueous solution and with a saturated sodium chloride aqueous solution, and dried over anhydrous sodium sulfate. Then, the solvent was distilled off under reduced pressure to give 1.20 g (yield 54%) of 8-chloro-6-ethoxycarbonyl-5-methylthiochroman-4-one-1,1-dioxide.

$^1$H-NMR ppm (CDCl$_3$, TMS): δ 1.33(3H,t), 2.53(3H,s), 3.20–3.38(2H,m), 3.59–3.78(2H,m), 4.34(2H,q), 7.84(1H,s)

4-2) Synthesis of 8-chloro-6-ethoxycarbonyl-4,4-ethylenedioxy-5-methylthiochroman-1,1-dioxide 1.0 Gram (3.2 mmol) of 8-chloro-6-ethoxycarbonyl-5-methylthiochroman-4-one-1,1-dioxide was dissolved in 6 l of toluene, and 0.20 g (1.2 eq., 3.6 mmol) of ethylene glycol and 50 mg of p-toluenesulfonic acid monohydrate were added. The mixture was refluxed for 14 hours. After the completion of the reaction, 5 ml of water was added, and the mixture was extracted with methylene chloride three times. An organic layer was washed with a saturated sodium chloride aqueous solution and dried over anhydrous sodium sulfate, and the solvent was distilled off to give 1.19 g (yield approximately 100%) of 8-chloro-6-ethoxycarbonyl-4,4-ethylenedioxy-5-methylthiochroman-1,1-dioxde.

$^1$H-NMR ppm (CDCl$_3$, TMS): δ 1.38(3H,t), 2.45(3H,s), 2.45–2.60(2H,m), 3.46–3.60(2H,m), 4.20–4.26(4H,m), 4.38 (2H,q), 7.74(1H,s)

4-3) Synthesis of 6-carboxy-8-chloro-4,4-ethylenedioxy-5-methylthiochroman-1,1-dioxide A mixture containing 1.19 g (3.2 mmol) of 8-chloro-6-ethoxycarbonyl-4,4-ethylenedioxy-5-methylthiochroman-1, 1-dioxide, 0.33 g (5.0 mmol) of potassium hydroxide, 8 ml of methanol and 2 ml of water was stirred under heat at 80° C. for 2 hours. After the completion of the reaction, 20 ml of water was added, and an aqueous layer was washed with methylene chloride. The aqueous layer was neutralized with 2 wt % hydrochloric acid and extracted with ethyl acetate. An organic layer was washed with a saturated sodium chloride aqueous solution and dried over anhydrous sodium sulfate, and the solvent was distilled off to give 0.92 g (yield 84%) of 6-carboxy-8-chloro-4,4-ethylenedioxy-5-methylthiochroman-1,1-dioxide in the form of a white solid.

m.p.: 247.7~258.4 (decomposed) $^1$H-NMR ppm (acetone-d$_6$, TMS): δ 2.52(3H,s), 2.52–2.70(2H,m), 3.49–3.64(2H, m), 4.38–4.48(4H,m), 7.88(1H,s)

Preparation Example 5

6-Carboxy-8-chloro-4,4-ethylenedithio-5-methylthiochroman-1,1-dioxide 5-1) Synthesis of 8-chloro-6-ethoxycarbonyl-4,4-ethylenedithio-5-methylthiochroman-1,1-dioxide 1.0 Gram (3.2 mmol) of 8-chloro-6-ethoxycarbonyl-5-methylthiochroman-4-one-1,1-dioxide was dissolved in 9 ml of methylene chloride, and 0.53 ml (2.0 eq., 6.3 mmol) of ethanedithiol and 0.12 ml (0.3 eq., 0.97 mmol) of boron trifluoride diethyl etherate were added. The mixture was refluxed for 2 days. After the completion of the reaction, 5 ml of water was added, and the mixture was extracted with methylene chloride three times. An organic layer was washed with a saturated sodium hydrogencarbonate aqueous solution and with a saturated sodium chloride aqueous solution, and dried over anhydrous sodium sulfate. The solvent was distilled off, and the resultant crude product was recrystallized from ethyl acetate-n-hexane to give 0.57 g (yield 46%) of 8-chloro-6-ethoxycarbonyl-4,4-ethylenedithio-5-methylthiochroman-1,1-dioxide.

$^1$H-NMR ppm (CDCl$_3$, TMS): δ 1.39(3H,s), 2.85(3H,s), 2.96–3.09(2H,m), 3.55–3.75(6H,m), 4.39(2H,q), 7.65(1H,s)

5-2) Synthesis of 6-carboxy-8-chloro-4,4-ethylenedithio-5-methylthiochroman-1,1-dioxide A mixture containing 0.57 g (1.5 mmol) of 8-chloro-6-ethoxycarbonyl-4,4-ethylenedithio-5-methylthiochroman-4-one-1,1-dioxide, 0.15 g, (2.3 mmol) of potassium hydroxide, 4 ml of methanol and 1 ml of water was stirred under heat at 80° C. for 2 hours. After the completion of the reaction, 10 ml of water was added, and an aqueous layer was washed with methylene chloride. The aqueous layer was neutralized with 2 wt % hydrochloric acid and extracted with ethyl acetate. An organic layer was washed with a saturated sodium chloride aqueous solution and dried over anhydrous sodium sulfate, and the solvent was distilled off to give 0.50 g (yield 94%) of 6-carboxy-8-chloro-4,4-ethylenedithio-5-methylthiochroman-4-one-1,1-dioxide in the form of a yellowish solid.

$^1$H-NMR ppm (acetone-$d_6$): δ 2.93(3H,s), 2.95–3.14(2H, m), 3.59–3.76(6H,m), 7.79(1H,s)

[SYNTHESIS OF PYRAZOLE DERIVATIVE, 6-(pyrazole-4-yl)carbonylthiochromans]

Preparation Example 6

6-(1-Ethyl-5-hydroxypyrazol-4-yl)carbonyl-3,3,5,8-tetramethylthiochroman-4-one-1,1-dioxide A 50-ml round-bottomed flask was charged with 0.51 g (1.72 mmol) of 6-carboxy-3,3,5,8-tetramethylthiochroman-4-one-1,1-dioxide, 0.21 g (1.88 mmol) of 1-ethyl-5-hydroxypyrazole and 5 ml of t-amyl alcohol, and while the mixture was stirred at room temperature, a solution of 0.42 g (2.04 mmol) of N,N'-dicyclohexylcarbodiimide in 2 ml of t-amyl alcohol was added. The mixture was further stirred at room temperature for 1 hour, and 0.18 g (1.30 mmol) of potassium carbonate was added to the reaction mixture. The mixture was heated at 80~90° C. for 8 hours. The solvent was distilled off under reduced pressure, and ethyl acetate and a 2 wt % sodium carbonate aqueous solution were added to the residue. An insoluble solid was removed by filtration. The mixture was separated into two phases, and an aqueous layer was neutralized and acidified with a 5 wt % hydrochloric acid aqueous solution, and a precipitated solid was extracted with ethyl acetate. An organic layer was washed with diluted hydrochloric acid and with a saturated sodium chloride aqueous solution, and dried over anhydrous sodium sulfate, and then the solvent was distilled off under reduced pressure to give 0.55 g (yield 82%) of 6-(1-ethyl-5-hydroxypyrazol-4-yl)carbonyl-3,3,5,8-tetramethylthiochroman-4-one-1,1-dioxide in the form of a brown solid. This product was recrystallized from mixed solvents of ethyl acetate and n-hexane to give 0.36 g (yield 54%) of a white solid.

m.p.: 159.5~163.0° C. $^1$H-NMR ppm (acetone-$d_6$, TMS): δ 1.30(3H,t), 1.38(6H,s), 2.31(3H,s), 2.70(3H,s), 3.75(2H, s), 4.04(2H,q), 7.38(1H,s), 7.54(1H,s) IRcm$^{-1}$(KBr): 3000 (C—H), 1620(C=O), 1300,1130(SO$_2$)

Preparation Example 7

6-(1-Ethyl-5-hydroxypyrazol-4-yl)carbonyl-3,3,5-trimethylthiochroman-4-one-1,1-dioxide 0.53 Gram (yield 82%) of 6-(1-ethyl-5-hydroxypyrazol-4-yl)carbonyl-3,3,5-trimethylthiochroman-4-one-1,1-dioxide was obtained in the same manner as in preparation Example 6 except that the 6-carboxy-3,3,5,8-tetramethylthiochroman-4-one-1,1-dioxide was replaced with 6-carboxy-3,3,5-trimethylthiochroman-4-one-1,1-dioxide.

$^1$H-NMR ppm (CDCl$_3$, TMS): δ 1.46(3H,t), 1.50(6H,s), 2.49(3H,s), 3.50(2H,s), 4.08(2H,q), 7.30(1H,s), 7.64–7.73 (1H,ABq), 7.88–7.97(1H,ABq) IRcm$^{-1}$(KBr): 2940,2980 (C—H), 1630(C=O), 1320,1130(SO$_2$)

Preparation Example 8

8-Chloro-6-(1-ethyl-5-hydroxypyrazol-4-yl) carbonyl-5-methylthiochroman-4-one 8-1) Synthesis of 8-chloro-6-(1-ethylpyrazol-5-yl) oxycarbonyl-5-methylthiochroman-4-one A mixture containing 2.0 g (7.8 mmol) of 6-carboxy-8-chloro-5-methylthiochroman-4-one and 2.8 g (3.0 eq., 24 mmol) of thionyl chloride was stirred under heat at 40° C. for 2 hours. After the completion of the reaction, excess thionyl chloride was removed under reduced pressure. Then, the resultant acid chloride was dissolved in 10 ml of methylene chloride, and 0.96 g (1.1 eq., 8.6 mmol) of 1-ethyl-5-hydroxypyrazole and 0.95 ml (9.41 mmol) of triethylamine were added. The mixture was stirred at room temperature for 3 hours. The reaction mixture was diluted with methylene chloride, washed with diluted hydrochloric acid and with a saturated sodium chloride aqueous solution and dried over anhydrous sodium sulfate, and the solvent was distilled off to give 2.29 g (yield 84%) of 8-chloro-6-(1-ethylpyrazol-5-yl)oxycarbonyl-5-methylthiochroman-4-one.

$^1$H-NMR ppm (CDCl$_3$, TMS): δ 1.44(3H,t), 2.74(3H,s), 2.98–3.12(2H,m), 3.23–3.33(2H,m), 4.09(2H,q), 6.21(1H, d), 7.48(1H,d), 8.01(1H,s)

8-2) Synthesis of 8-chloro-6-(1-ethyl-5-hydroxypyrazol-4-yl)carbonyl-5-methylthiochroman-4one 1.87 Grams (5.5 mmol) of 8-chloro-6-(1-ethylpyrazol-5-yl)oxycarbonyl-5-methylthiochroman-4-one was dissolved in 10 ml of acetonitrile, and 1.5 ml (2.0 eq., 11 mmol) of triethylamine and 5 drops of acetonecyanhydrin were added. The mixture was stirred at room temperature for about 20 hours. After the completion of the reaction, the reaction mixture was extracted with a saturated sodium hydrogencarbonate aqueous solution, and an aqueous layer was washed with methylene chloride. The aqueous layer was neutralized with 2 wt % hydrochloric acid and extracted with ethyl acetate. An organic layer was washed with a saturated sodium chloride aqueous solution and dried over anhydrous sodium sulfate, and the solvent was distilled off to give 0.89 g (yield 85%) of 8-chloro-6-(1-ethyl-5-hydroxypyrazol-4-yl)carbonylthiochroman-4-one in the form of a solid.

$^1$H-NMR ppm (CDCl$_3$, TMS): δ 1.45(3H,t), 2.54(3H,s), 3.01–3.10(2H,m), 3.21–3.31(2H,m), 4.08(2H,q), 7.37(1H, s), 7.48(1H,s) IRcm$^{-1}$(KBr): 2980,3050(C—H), 1660 (C=O)

Preparation Example 9

8-Chloro-6-(1-ethyl-5-hydroxypyrazol-4-yl) carbonyl-4,4-ethylenedioxy-5-methylthiochroman-1, 1-dioxide 9-1) Synthesis of 8-chloro-6-(1-ethylpyrazol-5-yl) oxycarbonyl-4,4-ethylenedioxy-5-methylthiochroman-1, 1-dioxide 0.92 Gram (2.8 mmol) of 6-carboxy-8-chloro-4,4-ethylenedioxy-5-methylthiochroman-1,1-dioxide was dissolved in 10 ml of methylene chloride, and 0.34 g (1.1 eq., 3.0 mmol) of 1-ethyl-5-hydroxypyrazole and 0.63 g (1.1 eq., 3.1 mmol) of N,N'-dicyclohexylcarbodiimide were added. The mixture was stirred at room temperature for 5 hours. Then, an insoluble substance was removed by filtration, and the filtrate was washed with a saturated sodium chloride aqueous solution and dried over anhydrous sodium sulfate. The solvent was distilled off to give 0.96 g (yield 81%) of 8-chloro-6-(1-ethylpyrazol-5-yl)oxycarbonyl-4,4-ethylenedioxy-5-methylthiochroman-1,1-dioxide.

$^1$H-NMR ppm (CDCl$_3$, TMS): δ 1.44(3H,t), 2.56(3H,s), 2.59–2.67(2H,m), 3.50–3.65(2H,m), 4.20–4.37(4H,m), 4.08 (2H,q), 6.27(1H,d), 7.49(1H,d), 7.98(1H,s)

9-2) Synthesis of 8-chloro-6-(1-ethyl-5-hydroxypyrazol-4-yl)carbonyl-4,4-ethylenedioxy-5-methylthiochroman-1,1-dioxide 0.96 Gram (2.2 mmol) of 8-chloro-6-(1-ethylpyrazol-5-yl)oxycarbonyl-4,4-ethylenedioxy-5-methylthiochroman-1,1-dioxide was dissolved in 5 ml of acetonitrile, and 0.63 ml (2.0 eq., 4.5 mmol) of triethylamine and 3 drops of acetonecyanhydrin were added. The mixture was stirred at room temperature for about 20 hours. After the completion of the reaction, the reaction mixture was extracted with a saturated sodium hydrogencarbonate aqueous solution, and an aqueous layer was washed with methylene chloride. The aqueous layer was neutralized with 2 wt % hydrochloric acid and extracted with ethyl acetate. An organic layer was washed with a saturated sodium chloride aqueous solution and then dried over anhydrous sodium sulfate, and the solvent was distilled off to give 0.82 g (yield 85%) of 8-chloro-6-(1-ethyl-5-hydroxypyrazol-4-yl)carbonyl-4,4-ethylenedioxy-5-methylthiochroman-1,1-dioxide in the form of a white solid.

m.p.: 209.0~214.6° C. (decomposed) $^1$H-NMR ppm (CDCl$_3$, TMS): δ 1.46(3H,t), 2.65(3H,s), 2.51–2.67(2H,m), 3.45–3.70(2H,m), 4.08(2H,q), 4.11–4.27(4H,m), 7.31(1H,s), 7.51(1H,s) IRcm$^{-1}$(KBr): 2950(C—H), 1630(C=O), 1300,1130(SO$_2$)

Preparation Example 10

8-Chloro-6-(1-ethyl-5-hydroxypyrazol-4-yl) carbonyl)-4,4-ethylenedithio-5methylthiochroman-1,1-dioxide 10-1) Synthesis of 8-chloro-6-(1-ethylpyrazol-5-yl) oxycarbonyl-4,4-ethylenedithio-5-methylthiochroman-1,1-dioxide 0.50 Gram (1.4 mmol) of 6-carboxy-8-chloro-4,4-ethylenedithio-5-methylthiochroman-1,1-dioxide was dissolved in 5 ml of methylene chloride, and 0.18 g (1.2 eq., 1.6 mmol) of 1-ethyl-5-hydroxypyrazole and 0.33 g (1.2 eq., 1.6 mmol) of N,N'-dicyclohexylcarbodiimide were added. The mixture was stirred at room temperature for 2 hours. Then, as insoluble substance was removed by filtration, and the filtrate was washed with a saturated sodium chloride aqueous solution and dried over anhydrous sodium sulfate. The solvent was distilled off to give 0.50 g (yield 80%) of 8-chloro-6-(1-ethylpyrazol-5-yl)oxycarbonyl-4,4-ethylenedithio-5-methylthiochroman-1,1-dioxide.

$^1$H-NMR ppm (CDCl$_3$, TMS): δ 1.44(3H,t), 2.96(3H,s), 2.96–3.12(2H,m), 3.60–3.80(6H,m), 4.06(2H,q), 6.27(1H, d), 7.48(1H,d), 7.98(1H,s) IRcm$^{-1}$(KBr): 2950(C—H), 1775 (C=O), 1320,1150(SO$_2$)

10-2) Synthesis of 8-chloro-6-(1-ethyl-5-hydroxypyrazol-4-yl)carbonyl-4,4-ethylenedithio-5-methylthiochroman-1,1-dioxide 0.50 Gram (1.0 mmol) of 8-chloro-6-(1-ethylpyrazol-5-yl)oxycarbonyl-4,4-ethylenedithio-5-methylthiochroman-1,1-dioxide was dissolved in 5 ml of acetonitrile, and 0.30 ml (2.0 eq., 2.0 mmol) of triethylamine and 2 drops of acetonecyanhydrin were added. The mixture was stirred at room temperature for about 20 hours. After the completion of the reaction, the reaction mixture was extracted with a saturated sodium hydrogencarbonate aqueous solution, and an aqueous layer was washed with methylene chloride. The aqueous layer was neutralized with 2 wt % hydrochloric acid and extracted with ethyl acetate. An organic layer was washed with a saturated sodium chloride aqueous solution and then dried over anhydrous sodium sulfate, and the solvent was distilled off to give 0.19 g (yield 38%) of 8-chloro-6-(1-ethyl-5-hydroxypyrazol-4-yl)carbonyl-4,4-ethylenedithio-5-methylthiochroman-1,1-dioxide in the form of a solid.

$^1$H-NMR ppm (acetone-d$_6$, TMS): δ 1.46(3H,t), 2.89(3H, s), 2.9–3.2(2H,m), 3.5–3.8(6H,m), 4.13(2H,q), 7.28(1H,s), 7.45(1H,s)

Table 20 shows the thiochroman carboxylic acids obtained in Preparation Examples 1 to 5 and the pyrazole derivatives obtained in Preparation Examples 6 to 10 in a manner in which these carboxylic acids correspond to the pyrazole derivatives.

TABLE 20

| Thiochroman carboxylic acid | | Pyrazole derivative | |
|---|---|---|---|
| Prepn Ex. No. | structural formula | Prepn Ex. No. structural formula | Comp'd No. |
| 1 | [structure: HO$_2$C-substituted thiochroman with CH$_3$ groups and SO$_2$] | 6 [structure: pyrazole-substituted thiochroman derivative with C$_2$H$_5$, OH, CH$_3$, SO$_2$ groups] | 1 |

TABLE 20-continued

| Thiochroman carboxylic acid | | Pyrazole derivative | | |
|---|---|---|---|---|
| Prepn Ex. No. | structural formula | Prepn Ex. No. | structural formula | Comp'd No. |
| 2 | [structure] | 7 | [structure] | 2 |
| 3 | [structure] | 8 | [structure] | 3 |
| 4 | [structure] | 9 | [structure] | 4 |
| 5 | [structure] | 10 | [structure] | 5 |

[SYNTHESIS OF INTERMEDIATES, 6-carboxythiochromans]

Preparation Example 11

6-Carboxy-4,4-ethylenedioxy-5-methylthiochroman-1,1-dioxide

28 Grams (77 mmol) of 8-chloro-6-ethoxycarbonyl-4,4-ethylenedioxy-5-methylthiochroman-1,1-dioxide was dissolved in 100 ml of ethanol, and 13.6 g (208 mmol) of a zinc powder was added. Further, a solution of 27 g (400 mmol) of sodium hydroxide in 50 ml of water and 50 ml of ethanol was added, and then the mixture was stirred under heat at 60° C. for 6 hours. After the completion of the reaction, an insoluble solid was removed by filtration, and an aqueous layer was washed with methylene chloride. The aqueous layer was acidified with a 5 wt % hydrochloric acid aqueous solution and extracted with ethyl acetate, and an organic layer was washed with a saturated sodium chloride aqueous solution and dried over anhydrous sodium sulfate. The solvent was distilled off under reduced pressure to give 16.2 g (yield 69%) of the titled compound.

$^1$H-NMR ppm (acetone-$d_6$, TMS): δ 2.55(3H,s), 2.60–2.76(2H,m), 3.44–3.58(2H,m), 4.32–4.34(4H,m), 7.84 (1H,d), 7.89(1H,d)

Preparation Example 12

6-Carboxy-5-methylthiochroman-4-one-1,1-dioxide 16.0 Grams (54 mmol) of 6-carboxy-4,4-ethylenedioxy-5-methylthiochroman-1,1-dioxide was dissolved in 90 ml of acetone and 30 ml of water, and 10 ml of a 12N hydrochloric acid aqueous solution was added. The mixture was stirred at room temperature for 2 days. After the completion of the reaction, the reaction mixture was concentrated, and extracted with ethyl acetate. An organic layer was washed with a saturated sodium chloride aqueous solution and dried over anhydrous sodium sulfate, and the solvent was distilled off under reduced pressure to give 13.7 g (yield: quantitative) of the titled compound.

$^1$H-NMR ppm (CDCl$_3$, TMS): δ 2.66(3H,s), 3.36(2H,t), 3.88(2H,t), 7.90(1H,d), 8.12(1H,d)

Preparation Example 13

6-Carboxy-3,3,5,8-tetramethylthiochroman-4-one

A mixture containing 10.8 g (41 mmol) of 6-acetyl-3,3,5,8-tetramethylthiochroman-4-one, 12.6 g (50 mmol) of iodine and 9.8 g (124 mmol) of pyridine was heated at 110~110° C. for 6 hours. After the completion of the reaction, excess pyridine was distilled off under reduced pressure, and to the residue were added 50 ml of ethylene glycol, 20 ml of water and 11 g (167 mmol) of potassium hydroxide. The mixture was refluxed under heat for 2 hours. After the reaction mixture was allowed to cool, 200 ml of a 1 wt % sodium hydroxide aqueous solution was added, and an aqueous layer was washed with chloroform twice and then acidified with a 5 wt % hydrochloric acid aqueous solution. A precipitated grey solid was collected by filtration under reduced pressure, washed with water and then dried under reduced pressure to give 10.3 g (yield 95%) of the title compound.

$^1$H-NMR ppm (acetone-d$_6$, TMS): δ 1.32(6H,s), 2.30(3H, s), 2.53(3H,s), 3.19(2H,s), 7.70(1H,s)

Preparation Example 14

6-Carboxy-5,8-dimethylthiochroman-4-one 14-2) Synthesis of 3-(4-ethoxycarbonyl-2,5-dimethylphenylthio)propionic acid 47 Grams (607 mmol) of a 70 wt % sodium hydrosulfide and 200 ml of toluene were added to 400 ml of N,N-dimethylformamide, and while the mixture was refluxed under heat for 2 hours, water was distilled off from the reaction system. When the temperature of the reaction mixture was decreased to about 100° C. while the reaction mixture was allowed to cool, 54 g (210 mmol) of ethyl-4-bromo-2,5-dimethylbenzoate was added, and the mixture was allowed to react at the same temperature for 6 hours. The reaction mixture was cooled to room temperature, 42 ml (607 mmol) of acrylic acid was dropwise added, then 84 ml (607 mmol) of triethylamine was added, and then the mixture was stirred at room temperature for about 1 day. The above procedures were all conducted under nitrogen atmosphere. The reaction mixture was diluted with water, and washed with ethyl acetate four times and with n-hexane once, and an aqueous layer was acidified with a 12N hydrochloric acid aqueous solution. A precipitated solid was collected by filtration under reduced pressure, washed with water, dissolved in ethyl acetate, washed with a saturated sodium chloride aqueous solution and dried over anhydrous sodium sulfate. The solvent was distilled off under reduced pressure to give 34.3 g (yield 58%) of the titled compound.

$^1$H-NMR ppm (CDCl$_3$, TMS): δ 1.35(3H,t), 2.29(3H,s), 2.55(3H,s), 2.72(2H,t), 3.30(2H,t), 4.30(2H,q), 7.25(1H,s), 7.71(1H,s)

14-2) Synthesis of 6-ethoxycarbonyl-5,8-dimethylthiochroman-4-one 21.5 Grams (64 mmol) of 3-(4-ethoxycarbonyl-2,5-dimethylphenylthio)propionic acid was added to 100 g of a 20 wt % P$_2$O$_5$-containing polyphosphoric acid at room temperature, and then the mixture was stirred under heat at 40° C. for 2 hours. After allowed to cool, the reaction mixture was gradually added to ice water and extracted with ethyl acetate, and an organic layer was washed with a 1 wt % sodium carbonate aqueous solution twice, with water twice and with a saturated sodium chloride aqueous solution once, and dried over anhydrous sodium sulfate. The solvent was distilled off under reduced pressure to give 14.6 g (yield 86%) of the titled compound.

$^1$H-NMR ppm (CDCl$_3$, TMS): δ 1.39(3H,t), 2.30(3H,s), 2.64(3H,s), 2.9–3.4(4H,m), 4.35(2H,q), 7.56(1H,s)

14-3) Synthesis of 6-carboxy-5,8-dimethylthiochroman-4-one

The titled compound was obtained in the same manner as in Preparation Example 3-3 except that the 8-chloro-6-ethoxycarbonyl-5-methylthiochroman-4-one was replaced with 6-ethoxycarbonyl-5,8-dimethylthiochroman-4-one. The yield of the end product was 92%.

$^1$H-NMR ppm (acetone-d$_6$, TMS): δ 2.29(3H,s), 2.60(3H, s), 2.9–3.1(2H,m), 3.2–3.4(2H,m), 7.69(1H,s)

Preparation Example 15

6-Carboxythiochroman-4-one

The titled compound was obtained in the same manner as in Preparation Example 14 except that the ethyl 4-bromo-2,5-dimethylbenzoate as a starting material in Preparation Example 14-1 was replaced with ethyl 4-bromobenzoate.

Preparation Example 16

6-Carboxy-8-fluoro-5-methylthiochroman-4-one

The titled compound was obtained in the same manner as in Preparation Example 3 except that the ethyl 4,5-dichloro-o-toluylate as a starting material in Preparation Example 3-1 was replaced with ethyl 4,5-difluoro-o-toluylate.

Preparation Example 17

6-Carboxy-5-chloro-4,4-ethylenedithio-8-methylthiochroman-1,1-dioxide 17-1) Synthesis of 5-chloro-6-ethoxycarbonyl-8-methylthiochroman-4-one The titled compound was obtained in the same manner as in Preparation Examples 14-1 and 14-2 except that the ethyl 4-bromo-2,5-dimethylbenzoate as a starting material in Preparation Example 14-1 was replaced with ethyl 4-bromo-6-chloro-m-toluylate, $^1$H-NMR ppm (CDCl$_3$, TMS): δ 1.39(3H,t), 2.28(3H,s), 2.9–3.4(4H,m), 4.37(2H,q), 7.47(1H,s)

17-2) Synthesis of 5-chloro-6-ethoxycarbonyl-8-methylthiochroman-4-one-1,1-dioxide The titled compound was obtained in the same manner as in Preparation Example 4-1 except that the 8-chloro-6-ethoxycarbonyl-5-methylthiochroman-4-one as a starting material in Preparation Example 4-1 was replaced with 5-chloro-6-ethoxycarbonyl-8-methylthiochroman-4-one.

$^1$H-NMR ppm (CDCl$_3$, TMS): δ 1.41(3H,t), 2.77(3H,s), 3.2–3.4(2H,m), 3.6–3.8(2H,m), 4.44(2H,q), 7.65(1H,s)

17-3) Synthesis of 6-carboxy-5-chloro-4,4-ethylenedithio-8-methylthiochroman-4-one-1,1-dioxide The titled compound was obtained in the same manner as in Preparation Example 5-1 and 5-2 except that the 8-chloro-6-ethoxycarbonyl-5-methylthiochroman-4-one-1,1-dioxide as a starting material in Preparation Example 5-1 was replaced with 5-chloro-6-ethoxycarbonyl-8-methylthiochroman-4-one-1,1-dioxide $^1$H-NMR ppm (acetone-d$_6$, TMS): δ 2.63(3H,s), 2.88–3.07(2H,m), 3.48–3.88(6H,m), 7.45(1H,s)

Preparation Example 18

6-Carboxy-5-chloro-3,3,8-trimethylthiochroman-4-one-1,1-dioxide

The titled compound was obtained in the same manner as in Preparation Examples 1-1 to 1-6 except that the 2,5-dimethylthiophenol as a starting material in Preparation Example 1-1 was replaced with 5-chloro-o-thiocresol.

$^1$H-NMR ppm (acetone-d$_6$, TMS): δ 1.48(6H,s), 2.71(3H, s), 3.84(2H,s), 7.86(1H,s)

Preparation Example 19

6-Carboxy-5-trifluoromethyl-3,3,8-trimethylthiochroman-4-one-1,1-dioxide 19-1) Synthesis of 6-ethoxycarbonyl-5-trifluoromethyl-3,3,8-trimethylthiochroman-4-one The titled compound was obtained in the same manner as in Preparation Example 2-2 except that the 3-(4-acetyl-2-chloro-5-methylphenylthio)pivalic acid as a starting material in Preparation Example 2-2 was replaced with 3-(4-ethoxycarbonyl-5-trifluoromethyl-2-methylphenylthio) pivalic acid and that the reaction temperature and time were changed to 80° C. and 1.5 hours. The yield was 79%.

$^1$H-NMR ppm (CDCl$_3$, TMS): δ 1.38(3H,t), 1.38(6H,s), 2.35(3H,s), 3.09(2H,s), 4.36(2H,q), 7.43(1H,s)

19-2) Synthesis of 6-ethoxycarbonyl-5-trifluoromethyl-3,3,8-trimethylthiochroman-4-one-1,1-dioxide The titled compound was obtained in the same manner as in Preparation Example 14-1 except that the 8-chloro-6-ethoxycarbonyl-5-methylthiochroman-4-one as a starting material in Preparation Example 4-1 was replaced with 6-ethoxycarbonyl-5-trifluoromethyl-3,3,8-trimethylthiochroman-4-one. The yield of the end product was 86%.

$^1$H-NMR p, (CDCl$_3$, TMS): δ 1.39(3H,t), 1.51(6H,s), 2.81(3H,s), 3.58(2H,s), 4.41(2H,q), 7.55(1H,s)

19-3) Synthesis of 6-carboxy-5-trifluoromethyl-3,3,8-trimethylthiochroman-4-one-1,1-dioxide 2.4 Grams (6.3 mmol) of 6-ethoxycarbonyl-5-trifluoromethyl-3,3,8-trimethylthiochroman-4-one-1,1-dioxide was dissolved in 25 ml of ethanol, and than a solution of 0.62 g (9.5 mmol) of potassium hydroxide in 3 ml of water was added. The mixture was stirred at room temperature for 2 hours, then diluted with water and washed with chloroform, and an aqueous layer was acidified with a 5 wt % hydrochloric acid aqueous solution. An organic precipitate was extracted with ethyl acetate, and an organic layer was washed with a saturated sodium chloride aqueous solution and dried over anhydrous sodium sulfate. The solvent was distilled off under reduced pressure to give 1.9 g (yield 86%) of the titled compound.

$^1$H-NMR ppm (CDCl$_3$, TMS): δ 1.51(6H,s), 2.82(3H,s), 3.61(2H,s), 7.75(1H,s)

Preparation Example 20

6-Carboxy-5-methoxy-3,3-dimethylthiochroman-4-one-1,1-dioxide 20-1) Synthesis of 6-carboxy-8-chloro-5-methoxy-3,3-dimethylthiochroman-4-one 19.9 Grams (62 mmol) of 3-(4-carboxy-2-chloro-5-methoxyphenylthio)pivalic acid was dissolved in 400 ml of dichloromethane, and while the reaction temperature was maintained below 5° C. with ice bath cooling, 16.9 ml (corresponding to 81 mmol of SO$_3$) of 20 wt % fuming sulfuric acid was gradually added. The reaction mixture was stirred at the same temperature for 30 minutes, then the ice bath was removed and stirred for 1 hour. Ice water was added to the reaction mixture to wash an organic layer, and then the organic layer was washed with a saturated sodium chloride aqueous solution and then dried over anhydrous sodium sulfate. The solvent was distilled off under reduced pressure to give 15.6 g (yield 83%) of the titled compound.

$^1$H-NMR ppm (CDCl$_3$, TMS): δ 1.36(6H,s), 3.14(2H,s), 3.96(3H,s), 8.16(1H,s)

20-2) Synthesis of 8-chloro-6-ethoxycarbonyl-5-methoxy-3,3-dimethylthiochroman-4-one 15.6 Grams (26 mmol) of 6-carboxy-8-chloro-5-methoxy-3,3-dimethylthiochroman-4-one and 7.9 g (57 mmol) of potassium carbonate were added to 80 ml of acetone, and then 8.8 g (57 mmol) of diethyl sulfate acid was added. The mixture was refluxed under heat for 5 hours. After the reaction, the solvent was distilled off under reduced pressure, and ethyl acetate and water were added to the residue to separate it into two phases. An organic layer was washed with a saturated sodium hydrogencarbonate aqueous solution and then with a saturated sodium chloride aqueous solution, and dried over anhydrous sodium sulfate. The solvent was distilled off under reduced pressure to give 15 g of a residue. The crude product was purified by silica gel column chromatography (eluent: n-hexane/ethyl acetate, 3:1 v/v) to give 11.0 g (yield 68%) of the titled compound.

$^1$H-NMR ppm (CDCl$_3$, TMS): δ 1.33(6H,s), 1.39(3H,t), 3.10(2H,s), 3.90(3H,s), 4.37(2H,q), 7.87(1H,s)

20-3) Synthesis of 8-chloro-6-ethoxycarbonyl-5-methoxy-3,3-dimethylthiochroman-4-one-1,1-dioxide The titled compound was obtained in the same manner as in Preparation Example 4-1 except that the 8-chloro-6-ethoxycarbonyl-5-methylthiochroman-4-one as a starting material in Preparation Example 4-1 was replaced with 8-chloro-6-ethoxycarbonyl-5-methoxy-3,3-dimethylthiochroman-4-one. The yield was 78%.

$^1$H-NMR ppm (CDCl$_3$, TMS): δ 1.42(3H,t), 1.46(6H,s), 3.58(2H,s), 3.94(3H,s), 4.43(2H,q), 8.02(1H,s)

20-4) Synthesis of 6-ethoxycarbonyl-5-methoxy-3,3-dimethylthiochroman-4-one-1,1-dioxide The titled compound was obtained in the same manner as in Preparation Example 2-4 except that the 6-acetyl-8-chloro-3,3,5-trimethylthiochroman-4-one-1,1-dioxide as a starting material in Preparation Example 2-4 was replaced with 8-chloro-6-ethoxycarbonyl-5-methoxy-3,3-dimethylthiochroman-4-one-1,1-dioxide and that the reaction temperature was changed to 50° C. The yield was 98%. It took 16 hours before a decrease in the hydrogen pressure terminated.

$^1$H-NMR ppm (CDCl$_3$, TMS): δ 1.42(3H,t), 1.49(6H,s), 3.48(2H,s), 3.98(3H,s), 4.44(2H,q), 7.73(1H,d), 8.07(1H,d)

20-5) Synthesis of 6-carboxy-5-methoxy-3,3-dimethylthiochroman-4-one-1,1-dioxide The titled compound was obtained in the same manner as in Preparation Example 19-3 except that the 6-ethoxycarbonyl-5-trifluoromethyl-3,3,8-trimethylthiochroman-4-one-1,1-dioxide as a starting material in Preparation Example 19-3 was replaced with 6-ethoxycarbonyl-5-methoxy-3,3-dimethylthiochroman-4-one-1,1-dioxide. The yield was 89%.

$^1$H-NMR ppm (CDCl$_3$, TMS): δ 1.52(6H,s), 3.52(2H,s), 4.05(3H,s), 7.83(1H,d), 8.36(1H,d)

Preparation Example 21

6-Carboxy-5,8-dimethylthiochrom-2-en-4-one 21-1) Synthesis of 3-bromo-6-ethoxycarbonyl-5,8-dimethylthiochroman-4-one 1.9 Grams (7.2 mmol) of 6-ethoxycarbonyl-5,8-dimethylthiochroman-4-one was dissolved in 28 ml of ethanol. Then, 1.2 g (7.5 mmol) of bromine was dropwise added with an ice bath cooling, and the mixture was stirred at the same temperature for 1 hour, then the ice bath was removed and further stirred for 1 hour. Water was added to the reaction mixture, and the reaction mixture was extracted with chloroform three times. An organic layer was washed with a saturated sodium chloride aqueous solution three times, and dried over anhydrous sodium sulfate. The solvent was distilled off under reduced pressure to give 2.4 g (yield 97%) of the titled compound.

$^1$H-NMR ppm (CDCl$_3$, TMS): δ 1.39(3H,t), 2.32(3H,s), 2.61(3H,s), 3.32–3.78(2H,m), 4.36(2H,q), 4.84–4.99(1H, m), 7.61(1H,s)

21-2) Synthesis of 6-ethoxycarbonyl-5,8-dimethylthiochrom-2-en-4-one 6.5 Milliliters of pyridine was added to 2.4 g (7.0 mmol) of 3-bromo-6-ethoxycarbonyl-5,8-dimethylthiochroman-4-one, and the mixture was allowed to react at 50° C. for 8 hours. After the reaction, the pyridine was distilled off under reduced pressure, and the residue was dissolved in ethyl acetate. An organic layer was washed with a 10 wt % hydrochloric acid aqueous solution and then with a saturated sodium chloride aqueous solution and dried over anhydrous sodium sulfate. The solvent was distilled off under reduced pressure to give 1.8 g of a residue. The crude product was purified by silica gel column chromatography (eluent: n-hexane/ethyl acetate, 3:1 v/v) to give 1.5 g (yield 82%) of titled compound.

$^1$H-NMR ppm (CDCl$_3$, TMS): δ 1.41(3H,t), 2.48(3H,s), 2.89(3H,s), 4.41(2H,q), 6.93(1H,d), 7.64(1H,s), 7.66(1H,d)

21-3) Synthesis of 6-carboxy-5,8dimethylthiochrom-2-en-4-one

The captioned end product was obtained in the same manner as in Preparation Example 3-3 except that the 8-chloro-6-ethoxycarbonyl-5-methylthiochroman-4-one as a starting material in Preparation Example 3-3 was replaced with 6-ethoxycarbonyl-5,8-dimethylthiochroman-2-en-4-one and that the reflux time was changed to 18 hours. The yield was 96%.

$^1$H-NMR ppm (DMSO-d$_6$, TMS): δ 2.46(3H,s), 2.77(3H, s), 6.96(1H,d), 7.75(1H,d), 8.22(1H,d)

[SYNTHESIS OF PYRAZOLE DERIVATIVES, 6-(pyrazole-4-yl)carbonylthiochromans]

Preparation Example 22–28

The pyrazole derivatives shown in Table 21 were obtained in the same manner as in Example 6 except that the 6-carboxy-3,3,5,8-tetramethylthiochroman-4-one-1,1-dioxide as a starting material in Preparation Example 6 was replaced with thiochroman carboxylic acid compounds shown in Table 21. The yields were as shown in Table 21.

TABLE 21

| prodn Ex. No. | starting carboxylic acid | yield (%) | pyrazole derivative | Comp'd No. |
|---|---|---|---|---|
| 22 | [structure] | 68 | [structure] | 6 |
| 23 | [structure] | 58 | [structure] | 7 |
| 24 | [structure] | 67 | [structure] | 8 |
| 25 | [structure] | 74 | [structure] | 9 |

TABLE 21-continued

| prodn Ex. No. | starting carboxylic acid | yield (%) | pyrazole derivative | Comp'd No. |
|---|---|---|---|---|
| 26 | 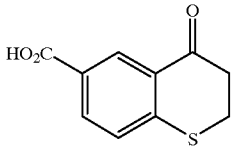 | 39 | 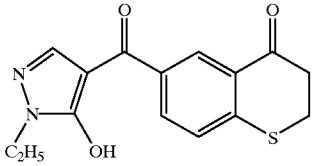 | 10 |
| 27 | 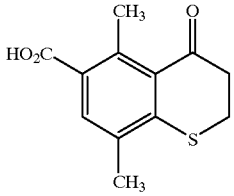 | 69 | 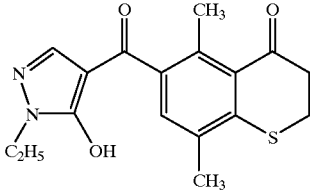 | 11 |
| 28 | 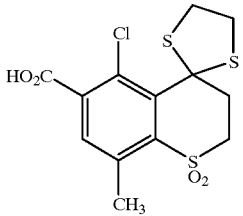 | 32 | 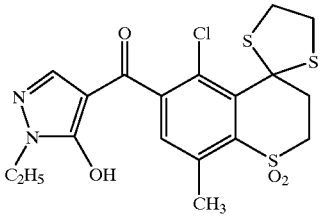 | 12 |

Table 24 shows the physical property data of the synthesized pyrazole compounds.

Preparation Examples 29 and 30

Intermediates and pyrazole derivatives shown in Table 22 were obtained in the same manner as in Preparation Examples 9-1 and 9-2 except that the 6-carboxy-8-chloro-4,4-ethylenedioxy-5-methylthiochroman-1,1-dioxide as a starting material in Preparation Example 9-1 was replaced with thiochroman carboxylic acid compounds shown in Table 22. The yields of the intermediates and the pyrazole derivatives were as shown in Table 22.

Preparation Examples 31 and 32

Intermediates and pyrazole derivatives shown in Table 22 were obtained in the same manner as in Preparation Examples 8-1 and 8-2 except that the 6-carboxy-8-chloro-5-methylthiochroman-4-one as a starting material in Preparation Example 8-1 was replaced with thiochroman carboxylic acid compounds shown in Table 22. The yields of the intermediates and the pyrazole derivatives were as shown in Table 22.

TABLE 22

| prodn Ex. No | starting carboxylic acid | yield 1 (%) | intermediate |
|---|---|---|---|
| 29 | | 95 | |

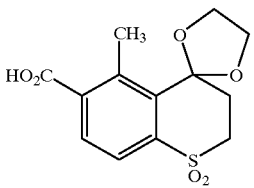

TABLE 22-continued

| prodn Ex. No | yield 2 (%) | pyrazole derivative | Comp'd No. |
|---|---|---|---|
| 29 | 94 | | 13 |
| 30 | 85 | | 14 |
| 31 | 91 | | 15 |

TABLE 22-continued

| 32 | 81 | | 16 |

[Structure: pyrazole (N-N, C₂H₅ on N, OH) connected via C=O to a benzene ring bearing CH₃ (top) and CH₃ (bottom), fused to a thiopyranone ring with S and C=O]

Table 24 shows the physical property data of the synthesized pyrazole compounds.

Preparation Example 33

6-(1-Ethyl-5-hydroxypyrazol-4-yl)carbonylthiochroman-4-one-1,1-dioxide 1.0 Gram (3.31 mmol) of 6-(1-ethyl-5-hydroxypyrazol-4-yl)carbonylthiochroman-4-one and 0.83 g (7.28 mmol) of a 30 wt % hydrogen peroxide aqueous solution were added to 3 ml of glacial acetic acid, and then stirred under heat of 60° C. for 2.5 hours. While the reaction mixture was cooled in an ice bath after allowed to cool, a 1 wt % sodium hydrogensulfite aqueous solution was added to decompose excess hydrogen peroxide, and then the reaction mixture was diluted with water. A precipitated solid was extracted with ethyl acetate. An organic layer was washed with water and then with a saturated sodium chloride aqueous solution once, and dried over anhydrous sodium sulfate. The solvent was distilled off under reduced pressure to give 1.11 g (yield: quantitative) of the titled compound. Table 24 shows the physical property data of the titled compound.

Preparation Example 34

6-(1-Ethyl-5-hydroxypyrazol-4-yl)carbonyl-5,8-dimethylthoichroman-4-one-1,1-dioxide The titled compound was obtained in the same manner as in Preparation Example 33 except that the 6-(1-ethyl-5-hydroxypyrazol-4-yl)carbonylthiochroman-4-one as a starting material in Preparation Example 33 was replaced with 6-(1-ethyl-5-hydroxypyrazol-4-yl)carbonyl-5,8-dimethylthiochroman-4-one. The yield was 90%. Table 24 shows the physical property data of the titled compound.

Preparation Example 35

6-(1-Ethyl-5-hydroxypyrazol-4-yl)carbonyl-8-fluoro-5-methylthiochroman-4-one-1,1-dioxide The titled compound was obtained in the same manner as in Preparation Example 33 except that the 6-(1-ethyl-5-hydroxypyrazol-4-yl)carbonylthiochroman-4-one as a starting material in Preparation Example 33 was replaced with 6-(1-ethyl-5-hydroxypyrazol-4-yl)carbonyl-8-fluoro-5-methylthiochroman-4-one. The yield was 83%. Table 24 shows the physical property data of the titled compound.

Preparation Example 36

6-(1-Ethyl-5-hydroxypyrazol-4-yl)carbonyl-5,8-dimethylthiochrom-2-en-4-one-1,1-dioxide 0.39 Gram (1.2 mmol) of 6-(1-ethyl-5-hydroxypyrazol-4-yl)carbonyl-5,8-dimethylthiochrom-2-en-4-one was dissolved in 4 ml of chloroform, and 0.62 g (2.6 mmol) of a 32 wt % peracetic acid/acetic acid solution was added. The mixture was allowed to react at room temperature for 5 hours, and then allowed to react at 50° C. for 2 hours and further stirred at room temperature for 17 hours. After the reaction, the reaction mixture was diluted with water, and a 1 wt % sodium sulfite aqueous solution was added to decompose excess peracetic acid. An organic substance was extracted with ethyl acetate, washed with a saturated sodium chloride aqueous solution and then dried over anhydrous sodium sulfate. The solvent was distilled off under reduced pressure to give 0.33 g (yield 77%) of the titled compound. Table 24 shows the physical property data of the titled compound.

Preparation Example 37

6-(1-Ethyl-5-hydroxypyrazol-4-yl)carbonyl-3,35,8-tetramethylthiochroman-4-one-1-oxide 10 Milliliters of glacial acetic acid was added to 3.45 g (13.1 mmol) of the 6-carboxy-3,3,5,8-tetramethylthiochroman-4-one synthesized in Preparation Example 13, and 1.63 g (14.4 mmol) of a 30 wt % hydrogen peroxide aqueous solution was added. The mixture was stirred at room temperature for 2 hours, and then allowed to react at 60° C. for 1 hour. After allowed to cool, the reaction mixture was diluted with water, and a 1 wt % sodium hydrogensulfite aqueous solution was added to decompose excess peroxide. An organic substance was extracted with ethyl acetate, washed with water twice and with a saturated sodium chloride aqueous solution once, and dried over anhydrous sodium sulfate. The solvent was distilled off under reduced pressure to give 3.88 g of a mixture containing 6-carboxy-3,3,5,8-tetramethylthiochroman-4-one-1-oxide and 6-carboxy-3,5,5,8-tetramethylthiochroman-4-one-1,1-dioxide. This intermediate was used to a subsequent reaction without separation or purification.

3.88 Grams of the above carboxylic acid mixture and 1.75 g (15.6 mmol) of 1-ethyl-5-hydroxypyrazole were added to 18 ml of t-amyl alcohol, and then 3.24 g (15.6 mmol) of N,N'-dicyclohexylcarbodiimide was added. The mixture was stirred at room temperature for 1 hour, and then 1.26 g (9.1 mmol) of potassium carbonate was added. The reaction mixture was heated at 80° C. for 8 hours, and then the solvent was distilled off under reduced pressure. To the residue were added a 2 wt % sodium carbonate aqueous solution and ethyl acetate, and an insoluble solid was removed by filtration under reduced pressure. Then, the filtrate was separated into two phases. An aqueous layer was acidified with a 5 wt % hydrochloric acid aqueous solution, and a precipitated viscous solid was extracted with ethyl acetate. An organic layer was washed with a diluted hydrochloric acid and then with a saturated sodium chloride aqueous solution and dried over anhydrous sodium sulfate.

The solvent was distilled off, and the resultant oil residue (5.3 g) was purified by silica gel column chromatography (eluent; ethyl acetate containing 2% v/v acetic acid) to give 2.74 g (yield 56%) of the titled compound. At the same time, 1.23 g (yield 24%) of 6-(1-ethyl-5-hydroxypyrazol-4-yl)carbonyl-3,3,58-tetramethylthiochroman-4-one-1,1-dioxide (Compound No. 1) was also obtained. Table 24 shows the physical property data of the titled compound.

Table 23 shows the structural formulae of the pyrazole compounds synthesized in Preparation Examples 33 to 37.

TABLE 23

| prodn Ex. No | starting material | pyrazole derivative | Comp'd No. |
|---|---|---|---|
| 33 | 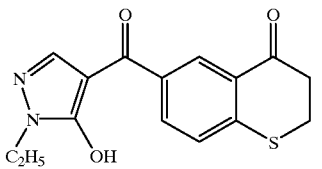 | 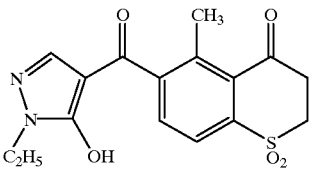 | 17 |
| 34 | 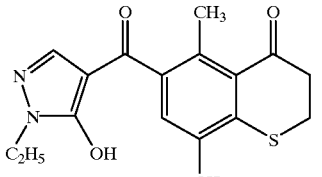 | 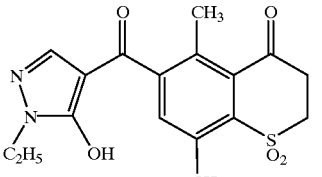 | 18 |
| 35 | 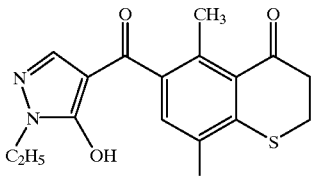 | 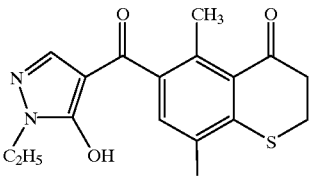 | 19 |
| 36 | 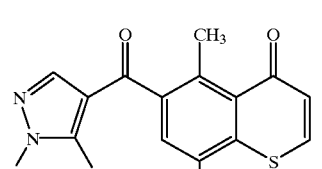 | 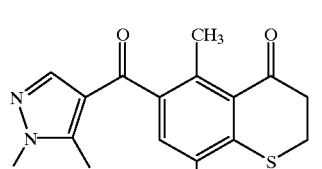 | 20 |
| 37 | 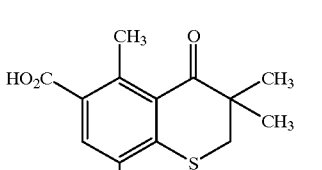 | 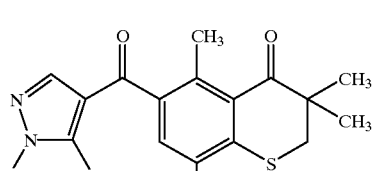 | 21 |

TABLE 24

| Comp'd. No. | ¹H-NMR (ppm) (internal standard:TMS) | IR (cm$^{-1}$) |
|---|---|---|
| 6* | 1.45(3H, t), 1.48(6H, s), 2.72(3H, s), 3.53(2H, s), 4.06(2H, q), 7.31(1H, s), 7.42(1H, s) (CDCl$_3$) | 3000, 1730, 1650, 1320, 1150 |

TABLE 24-continued

| Comp'd. No. | ¹H-NMR (ppm) (internal standard:TMS) | IR (cm$^{-1}$) |
|---|---|---|
| 7 | 1.47(3H, t), 1.53(6H, s), 2.83(3H, s), 3.61(2H, s), 4.09(2H, q), 5.15(1H, bs), 7.35(1H, s), 7.51(1H, s) (CDCl$_3$) | 3000, 1720, 1660, 1330, 1150 |
| 8** | 1.46(3H, t), 1.52(6H, s), 3.52(2H, s), 3.85(3H, s), 4.08(2H, q), 7.45(1H, s) | — |
| 9 | 1.45(3H, t), 1.50(6H, s), 3.61(2H, s), 3.80(3H, s), 4.08(2H, q), 7.47(1H, s), 7.80(2H, s) (CDCl$_3$) | 3000, 1700, 1660, 1330, |

TABLE 24-continued

| Comp'd. No. | ¹H-NMR (ppm) (internal standard:TMS) | IR (cm⁻¹) |
|---|---|---|
|  | 7.76(1H, s) (CDCl₃) | 1140 |
| 10 | 1.30(3H, t), 2.9–3.1(2H, m), 3.3–3.5 2H, m), 3.95(2H, q), 7.51(1H, d), 7.63 (1H, s), 7.88(1H, dd), 8.35(1H, d) (DMSO-d₆) | — |
| 11 | 1.45(3H, t), 2.31(3H, s), 2.54(3H, s), 2.9–3.4(4H, m), 4.07(2H, q), 6.50(1H, bs), 7.27(1H, s), 7.35(1H, s) (CDCl₃) | 3000, 1690, 1640 |
| 12 | 1.3–1.7(3H,m), 2.77(3H, s), 2.9–3.2 (2H, m), 3.4–3.9(6H, m), 3.9–4.3(2H, m), 7.31(1H, s), 7.44(1H, s) (CDCl₃) | 3000, 1740, 1310, 1140 |
| 13 | 1.39(3H, t), 2.40(3H, s), 2.6—2.9(2H, m), 3.4–3.7(2H, m), 4.05(2H, q), 4.31 (4H, bs), 7.35(1H, s), 7.65(1H, d), 7.85(1H, d) (acetone-d₆) | 2990, 1740, 1720, 1320, 1130 |
| 14 | 1.40(3H, t), 2.50(3H, s), 3.3–3.5(2H, m), 3.8–4.0(2H, m), 4.06(2H, q), 7.37 1H, s), 7.88(1H, d), 7.92(1H, d) (acetone-d₆) | 2950, 1700, 1640, 1310, 1140 |
| 15 | 1.45(3H, t), 2.55(3H, s), 2.9–3.4(4H, m), 4.07(2H, q), 6.7(1H, bs), 7.20(1H, d), 7.35(1H, s) (CDCl₃) | — |
| 16 | 1.46(3H, t), 2.50(3H, s), 2.82(3H, s), 4.08(2H, q), 6.96(1H, d), 7.32(1H, s), 7.40(1H, s), 7.71(1H, d) (CDCl₃) | 3000, 1620 |
| 17 | 1.28(3H, t), 3.2–3.4(2H, m), 3.8–4.0 (2H, m), 4.05(2H, q), 7.65(1H, s), 8.0–8.5(3H, m) (DMSO-d₆) | — |
| 18 | 1.46(3H, t), 2.51(3H, s), 2.79(3H, s), 3.2–3.5(2H, m), 3.6–3.9(2H, m), 4.07 (2H, q), 5.10(1H, bs), 7.31(1H, s), 7.45(1H, s) (CDCl₃) | 3000, 1710, 1640, 1320, 1130 |
| 19 | 1.25(3H, t), 2.30(3H, 5), 3.1–3.4(2H, m), 3.8–4.0(2H, m), 4.05(2H, q), 7.42 (1H, s), 7.73(1H, d) (DMSO-d₆) | — |
| 20 | 1.46(3H, t), 2.61(3H, s), 2.86(3H, s), 4.08(2H, q), 6.70(1H, d), 7.15(1H, s), 7.25(1H, d), 7.52(1H, s) (CDCl₃) | 3020, 1690, 1640, 1310, 1130 |
| 21 | 1.24(3H, s), 1.46(3H, t), 1.65(3H, s), 1.42(3H, s), 1.64(3H, s), 2.85(1H, d), 3.60(1H, d), 7.32(1H, s), 7.39(1H, s) (CDCl₃) | 2990, 1710, 1680, 1040 |

*mp 171.3~173.9° C.
**mp 198.5~201.9° C.

Preparation Example 38

6-(1-Ethyl-5-n-propanesulfonyloxypyrazol-4-yl) carbonyl-3,3,5,8-tetramethylthiochroman-4-one-1,1-dioxide 2.3 Grams (5.9 mmol) of 6-(1-ethyl-5-hydroxypyrazol-4-yl)carbonyl-3,3,5,8-tetramethylthiochroman-4-one-1,1-dioxide was dissolved in 15 ml of dichloromethane. Separately, 1.22 g (8.8 mmol) of potassium carbonate was dissolved in 20 ml of water, and these two solutions were mixed. Then, a solution of 1.26 g (8.8 mmol) of n-propanesulfonyl chloride in 5 ml of dichloromethane was added. Further, a small amount (about 50 mg) of benzyltrimethylammonium chloride was added, and the mixture was stirred at room temperature for about 15 hours. The reaction mixture was diluted with dichloromethane and water and separated into two phases, and an organic layer was washed with diluted hydrochloric acid, then with water and with a saturated sodium chloride aqueous solution and dried over anhydrous sodium sulfate. The solvent was distilled off under reduced pressure, and 3.02 g of the resultant oil was purified by silica gel column chromatography (eluent: n-hexane/ethyl acetate, 2:1 v/v) to give 2.6 g (yield 89%) of the titled compound. Table 25 shows the structural formula of the titled compound, and Table 27 shows the physical property data thereof.

Preparation Examples 39–46

The pyrazole derivatives shown in Table 25 were obtained in the same manner as in Preparation Example 38 except tat the 6-(1-ethyl-5-hydroxypyrazol-4-yl)carbonyl-3,3,5,8-tetramethylthiochroman-4-one-1,1-dioxide as a starting material in Preparation Example 38 was replaced with hydroxypyrazole derivatives shown in Table 25. Table 25 shows the yields of the pyrazole derivatives.

TABLE 25

| prodn Ex. No | starting material | yield (%) | pyrazole derivative | Comp'd No. |
|---|---|---|---|---|
| 38 | [structure: 1-ethyl-5-hydroxypyrazol-4-yl carbonyl 3,3,5,8-tetramethylthiochroman-4-one 1,1-dioxide] | 89 | [structure: 1-ethyl-5-(n-propanesulfonyloxy)pyrazol-4-yl carbonyl 3,3,5,8-tetramethylthiochroman-4-one 1,1-dioxide] | 22 |

TABLE 25-continued

| prodn Ex. No | starting material | yield (%) | pyrazole derivative | Comp'd No. |
|---|---|---|---|---|
| 39 | | 83 | | 23 |
| 40 | | 85 | | 24 |
| 41 | | 86 | | 25 |
| 42 | | 53 | | 26 |
| 43 | | 94 | | 27 |

TABLE 25-continued

| prodn Ex. No | starting material | yield (%) | pyrazole derivative | Comp'd No. |
|---|---|---|---|---|
| 44 | (structure) | 31 | (structure) | 28 |
| 45 | (structure) | 41 | (structure) | 29 |
| 46 | (structure) | 73 | (structure) | 30 |

Table 27 shows the physical property data of the synthesized pyrazole compounds.

Preparation Example 47

5-Chloro-6-(1-ethyl-5-(4-methylphenylsulfonyloxy) pyrazol-4-yl)carbonyl-3,3,8-trimethylthiochroman-4-one-1,1-dioxide 0.60 Gram (1.46 mmol) of 5-chloro-6-(1-ethyl-5-hydroxypyrazol-4-yl)carbonyl-3,3,8-trimethylthiochroman-4-one-1,1-dioxide was dissolved in 7 ml of dicholoromethane. Separately, 0.25 g (1.81 mmol) of potassium carbonate was dissolved in 7 ml of water, and these two solutions were mixed. Then, 0.34 g(1.78 mmol) of p-toluenesulfonyl chloride was added. Further, a small amount (about 20 mg) of benzyltriethylammonium chloride was added, and the mixture was stirred at room temperature for about 15 hours. The reaction mixture was diluted with dichloromethane and water and separated into two phases, and an organic layer was washed with diluted hydrochloric acid, then with water and with a saturated sodium chloride aqueous solution and dried over anhydrous sodium sulfate. The solvent was distilled off under reduced pressure, and 0.77 g of the resultant oil was purified by silica gel column chromatography (developer solution: n-hexane/ethyl acetate, 2:1 v/v) to give 0.67 g (yield 82% of the titled compound. Table 26 shows the structural formula of the titled compound, and Table 27 shows the physical property data thereof.

Preparation Examples 48–50

The pyrazole derivatives shown in Table 26 were obtained in the same manner as in Preparation Example 47 except that the 5-chloro-6-(1-ethyl-5-hydroxypyrazol-4-yl)carbonyl-3,3,8-trimethylthiochroman-4-one-1,1-dioxide as a starting material in Preparation Example 47 was replaced with hydroxypyrazole derivatives shown in Table 26. Table 26 shows the yields of the pyrazole derivatives.

Preparation Example 51

6-(1-Ethyl-5-cyclohexanecarbonyloxypyrazol-4-yl) carbonyl-5-trifluoromethyl-3,3,8-trimethylthiochroman-4-one,1,1-dioxide 0.30 Gram (0.68 mmol) of 6-(1-ethyl-5-hydroxypyrazol-4-yl)carbonyl-5-trifluoromethyl-3,3,8-trimethylthiochroman-4-one-1,1-dioxide and 0.12 g (0.82 mmol) of cyclohexanecarbonyl chloride were added to 5 ml of 1,2-dichloroethane, and then 0.07 g (0.89 mmol) of pyridine was added. The mixture was stirred at room temperature for about 15 hours, and then reaction mixture was diluted with chloroform. An organic layer was washed with diluted hydrochloric acid, then with water and with a saturated sodium chloride aqueous solution and dried over anhydrous sodium sulfate. The solvent was distilled off under reduced pressure, and 0.30 g of the resultant oil was purified by silica gel column chromatography (eluent: n-hexane/ethyl acetate, 2:1 v/v) to give 0.19 g(yield 51%) of the titled compound. Table 26 shows the structural formula of the titled compound, and Table 27 shows the physical property data thereof.

TABLE 26

| prodn Ex. No | starting material | yield (%) | pyrazole derivative | Comp'd No. |
|---|---|---|---|---|
| 47 | | 82 | | 31 |
| 48 | | 70 | | 32 |
| 49 | | 57 | | 33 |
| 50 | | 60 | | 34 |

TABLE 26-continued

| prodn Ex. No | starting material | yield (%) | pyrazole derivative | Comp'd No. |
|---|---|---|---|---|
| 51 | (structure) | 51 | (structure) | 35 |

TABLE 27

| Comp'd. No. | ¹H-NMR (ppm) (internal standard:TMS) | IR (cm⁻¹) |
|---|---|---|
| 22* | 1.18(3H, t), 1.46(6H, s), 1.52(3H, t), 1.9–2.3(2H, m), 2.34(3H, s), 2.74(3H, s), 3.54(2H, s), 3.6–3.8(2H, m), 4.14 (2H, q), 7.35(1H, s), 7.45(1H, s) (CDCl₃) | 3000, 1720, 1670, 1340, 1140 |
| 23 | 1.18(3H, t), 1.50(6H, s), 1.53(3H, t), 1.9–2.3(2H, m), 2.44(3H, s), 3.50(2H, s), 3.6–3.8(2H, m), 4.23(2H, q), 7.45 (1H, s), 7.63(1H, d), 7.92(1H, d) (CDCl₃) | 2980, 1700, 1660, 1320, 1120 |
| 24 | 1.17(3H, t), 1.22(3H, s), 1.52(3H, t), 1.65(3H, s), 1.9–2.3(2H, m), 2.36(3H, s), 2.64(3H, s), 2.83(1H, d), 3.60(1H, d), 3.6–3.8(2H, m), 4.23(2H, q), 7.33 (1H, s), 7.47(1H, s) (CDCl₃) | 3000, 1710, 1660, 1040 |
| 25 | 1.18(3H, t), 1.48(6H, s), 1.52(3H, t), 1.9–2.4(2H, m), 2.75(3H, s), 3.56(2H, s), 3.6–3.9(2H, m), 4.23(2H, q), 7.41 (1H, s), 7.50(1H, s) (CDCl₃) | 3000, 1730, 1680, 1340, 1140 |
| 26 | 1.18(3H, t), 1.52(6H, s), 1.52(3H, t), 1.9–2.4(2H, m), 3.52(2H, s), 3.7–3.9 (2H, m), 3.80(3H, s), 4.22(2H, q), 7.52 (1H, s), 7.74(1H, d), 7.76(1H, d) (CDCl₃) | 3000, 1710, 1670, 1330, 1140 |
| 27 | 1.19(3H, t), 1.49(6H, s), 1.51(3H, t), 1.9–2.3(2H, m), 3.61(2H, s), 3.7–4.0 (2H, m), 3.76(3H, s), 4.22(2H, q), 7.55 (1H, s), 7.66(1H, s) (CDCl₃) | 3000, 1720, 1670, 1330, 1140 |
| 28 | 1.19(3H, t), 1.51(3H, t), 1.9–2.3(2H, m), 2.80(3H, s), 2.9–3.2(2H, m), 3.4–3.9(8H, m), 4.21(2H, q), 7.21(1H, s), 7.41(1H, s) (CDCl₃) | 3000, 1680, 1300, 1140 |
| 29 | 1.18(3H, t), 1.51(3H, s), 1.8–2.3(2H, m), 2.36(3H, s), 2.5–2.8(2H, m), 3.4–3.9(4H, m), 3.9–4.4(4H, m), 7.44(1H, s), 7.49(1H, d), 7.89(1H, d) (CDCl₃) | 3000, 1710, 1680, 1330, 1140 |
| 30 | 1.11(3H, t), 1.44(3H, t), 1.8–2.2(2H, m), 2.47(3H, s), 3.30(3H, t), 3.5–3.8 (4H, m), 4.11(2H, q), 7.31(1H, s), 7.59 (1H, d), 7.92(1H, d) (CDCl₃) | 2970, 1720, 1680, 1340, 1140 |
| 31 | 1.47(6H, s), 1.47(3H, t), 2.48(3H, s), 2.71(3H, s), 3.54(2H, s), 4.09(2H, q), 7.29(1H, s), 7.40(2H, d), 7.62(1H, s) 7.86(2H, d) (CDCl₃) | 3000, 1730, 1680, 1330 1160 |
| 32 | 1.42(3H, t), 1.51(6H, s), 2.48(3H, s), 3.50(2H, s), 3.76(3H, s), 4.00(2H, q), 7.39(2H, d), 7.64(1H, s), 7.68(1H, d) 7.71(1H, d), 7.81(2H, d) (CDCl₃) | 3000, 1710, 1670, 1320 1140 |
| 33 | 1.50(3H, t), 2.34(3H, s), 2.47(3H, s), 2.6–2.8(2H, m), 3.4–3.7(2H, m), 3.9–4.4(6H, m), 7.33(1H, d), 7.41(2H, d), 7.47(1H, s), 7.79(1H, d), 7.89(2H, d) (CDCl₃) | 3000, 1750, 1670, 1310, 1140 |
| 34 | 1.47(3H, t), 2.48(3H, s), 2.49(3H, s), 3.3–3.5(2H, m), 3.6–3.8(2H, m), 4.11 (2H, q), 7.41(2H, d), 7.51(1H, s), 7.55 (1H, d), 7.86(2H, d), 7.92(1H, d) (CDCl₃) | 2950, 1700, 1670, 1330, 1130 |
| 35 | 1.44(3H, t), 1.51(6H, s), 1.1–2.2(11H) m), 2.79(3H, s), 3.58(2H, s), 4.00(2H, q), 7.41(1H, s), 7.57(1H, s) (CDCl₃) | 2920, 1776, 1710, 1310, 1150 |

*mp 130.0~133.0° C.

Preparation Example 52

4-Hydroxy-5-methyl-6-carboxythiochroman-1,1-dioxide 52-1) Synthesis of 4-hydroxy-5-methyl-6-ethoxycarbonyl-8-chlorothiochroman-1,1-dioxide 25.8 Grams (90 mmol) of 4-hydroxy-5-methyl-6-ethoxycarbonyl-8-chlorothiochroman was dissolved in 70 ml of acetic acid, and 46 ml (0.45 mol, 5 eq.) of a 30 wt % hydrogen peroxide aqueous solution was added. The mixture was stirred at 80° C. for 4 hours. The reaction mixture was allowed to cool, and a precipitated solid was collected by filtration, washed with 200 ml of water and dried under reduced pressure to give 21.9 g (yield 95%) of 4-hydroxy-5-methyl-6-ethoxycarbonyl-8-chlorothiochroman-1,1-dioxide.

¹H-NMR ppm (CDCl₃, TMS): δ

1.40(3H,t), 2.59(3H,s), 2.5–4.2(4H,m), 4.40(2H,q), 5.09(1H,bs), 7.67(1H,s)

52-2) Synthesis of 4-hydroxy-5-methyl-6-carboxythiochroman-1,1-dioxide

10 Grams (31 mmol) of 4-hydroxy-5-methyl-6-ethoxycarbonyl-8-chlorothiochroman-1,1-dioxide was dissolved in 30 ml of ethanol, and 50 ml of a 16 wt % potassium hydroxide aqueous solution and 6.1 g (93 mg atom, 3 eq.) of a zinc powder were added. The mixture was stirred under heat at 50° C. for 3 hours. After the completion of the reaction, the zinc powder was separated by filtration. While the reaction mixture was cooled, 2N hydrochloric acid aqueous solution was added to adjust a pH of 1. Then, the reaction mixture was extracted with ethyl acetate twice. An organic layer was washed with a saturated sodium chloride aqueous solution and dried over anhydrous sodium sulfate, and the solvent was distilled off to give 11.5 g (yield 100%) of 4-hydroxy-5-methyl-6-carboxythiochroman-1,1-dioxide.

m.p.: 172~173° C.

hu 1H-NMR ppm (acetone-d$_6$, TMS): δ
2.5–2.8(2H,m), 2.69(3H,s)3.1–4.1(2H,m), 5.22(1H,t), 7.75(1H,d), 7.94(1H,d)

Preparation Example 53

4-Ethylthio-5-methyl-6-carboxythiochroman-1,1-dioxide 53-1) Synthesis of 4-chloro-5-methyl-6-(1-ethylpyrazol-5-yl)oxycarbonylthiochroman-1,1-dioxide 2.2 Milliliters (30 mmol, 4 eq.) of thionyl chloride was added to 1.9 g (7.5 mmol) of 4-hydroxy-5-methyl-6-carboxythiochroman-1,1-dioxide, and the mixture was stirred under heat at 80° C. for 3 hours. After the completion of the reaction, the reaction mixture was concentrated under reduced pressure, and unreacted thionyl chloride was removed to give an acid chloride. 1.1 Grams (9.8 mmol, 1.3 eq.) of 1-ethyl-5-hydroxypyrazole and 1.4 ml of triethylamine were dissolved in 5 ml of tetrahydrofuran (THF), and the mixture was cooled in an ice bath. The above acid chloride was dissolved in 3 ml of THF, and the resultant solution was gradually dropwise added to the mixture. The mixture was allowed to react at room temperature for 1 day, and then extracted with ethyl acetate twice. An organic layer was washed with a saturated sodium chloride aqueous solution and dried over anhydrous sodium sulfate, and the solvent was distilled off. The remaining oil was purified by column chromatography (silica gel/hexane+ethyl acetate= 1:1) to give 1.5 g (yield 55%) of 4-chloro-5-methyl-6-(1-ethylpyrazol-5-yl)oxycarbonylthiochroman-1,1-dioxide.

m.p.: 144~146° C.

$^1$H-NMR ppm (CDCl$_3$, TMS): δ

1.44(3H,t), 2.77(3H,s), 2.8–3.6(4H,m), 4.09(2H,q), 5.54 (1H,t), 6.27(1H,d), 7.48(1H,d), 7.94(1H,d), 8.15(1H,d)

53-2) Synthesis of 4-ethylthio-5-methyl-6-ethylthiocarbonylthiochroman-1,1-dioxide 0.62 g (1.7 mmol) of 4-chloro-5-methyl-6-(1-ethylpyrazol-5-yl)oxycarbonylthiochroman-1,1-dioxide was dissolved in 3 ml of N,N-dimethylformamide, and 0.3 ml (6.3 mmol, 3.7 eq.) of ethanethiol and 0.35 g (2.5 mmol, 1.5 eq.) of potassium carbonate were added. The mixture was stirred at room temperature for 1 day. After the completion of the reaction, 10 ml of water was added, and the mixture was extracted with ethyl acetate twice. An organic layer was washed with a saturated sodium chloride aqueous solution and dried over anhydrous sodium sulfate, and the solvent was distilled off to give 0.6 g (yield 89%) of 4-ethylthio-5-methyl-6-ethylthiocarbonylthiochroman-1,1-dioxide.

$^1$H-NMR ppm (CDCl$_3$, TMS): δ

1.1–1.5(6H,m), 2.57(3H,s), 2.4–3.5(7H,m), 4.0–4.5(2H, m), 7.57(1H,d), 7.79(1H,d)

53-3) Synthesis of 4-ethylthio-5-methyl-6-carboxythiochroman-1,1-dioxide 0.6 Gram (1.5 mmol) of 4-ethylthio-5-methyl-6-ethylthiocarbonylthiochroman-1,1-dioxide, 0.12 g (2.1 mmol) of potassium hydroxide, 3 ml of ethanol and 1 ml of water were stirred under heat at 60° C. for 3 hours. After the completion of the reaction, the solvent was distilled off, 5 ml of water was added, and then 2N hydrochloric acid was added to adjust a pH of 1. Then, the mixture was extracted with ethyl acetate twice. An organic layer was washed with a saturated sodium chloride aqueous solution and dried over anhydrous sodium sulfate, and the solvent was distilled off to give 0.51 g (yield 100%) of 4-ethylthio-5-methyl-6-carboxythiochroman-1,1-dioxide.

$^1$H-NMR ppm (acetone-d$_6$, TMS): δ

1.30(3H,t), 2.74(3H,s), 2.5–3.0(4H,m), 3.3–3.6(1H,m), 4.0–4.4(1H,m), 4.58(1H,t), 8.76(1H,d), 8.90(1H,d)

Preparation Example 54

4-Ethylthio-5-methyl-6-carboxy-8-chlorothiochroman 54-1) Synthesis of 4-hydroxy-5-methyl-6-ethoxycarbonyl-8-chlorothiochroman 13.0 Grams (45.7 mmol) of 5-methyl-6-ethoxycarbonyl-8-chlorothiochroman-4-one was dissolved in 50 ml of ethanol, and 1.73 g (45.7 mmol, 1 eq.) of sodium borohydride was added with an ice bath cooling. The reaction mixture was stirred for 1 hour. After the completion of the reaction, 20 ml of water was added, and the solvent was distilled off. Then, the reaction mixture was extracted with ethyl acetate twice. An organic layer was washed with a saturated sodium chloride aqueous solution and dried over anhydrous sodium sulfate, and the solvent was distilled off to give 14.0 g (yield 100%) of 4-hydroxy-5-methyl-6-ethoxycarbonyl-8-chlorothiochroman.

$^1$H-NMR ppm (CDCl$_3$, TMS): δ

1.37(3H,t), 1.75(1H,m), 2.2–2.5(2H,m), 2.61(3H,s), 2.85 (1H,m), 3.12(1H,m), 4.32(2H,q), 5.06(1H,bs), 7.71 (1H,s)

54-2) Synthesis of 4,8-dichloro-5-methyl-6-ethoxycarbonylthiochroman 1.0 Gram (3.5 mmol) of 4-hydroxy-5-methyl-6-ethoxycarbonyl-8-chlorothiochroman was dissolved in 5 ml of methylene chloride, and 0.72 ml (5.2 mmol) of triethylamine and 0.4 ml (5.2 mmol) of methanesulfonyl chloride were added with an ice bath cooling. The mixture was stirred at room temperature for 1 hour. After the completion of the reaction, an organic layer was washed with 2N hydrochloric acid and with a saturated sodium hydrogencarbonate aqueous solution and dried over anhydrous sodium sulfate, and the solvent was distilled off to give 1.24 g (yield 100%) of 4,8-dichloro-5-methyl-6-ethoxycarbonylthiochroman.

$^1$H-NMR ppm (CDCl$_3$, TMS); δ

1.36(3H,t), 2.23(1H,m), 2.61(3H,s), 2.7–3.2(2H,m), 3.61 (1H,ddd), 4.33(2H,q), 5.47(1H,t), 7.75(1H,s)

54-3) Synthesis of 4-ethylthio-5-methyl-6-ethoxycarbonyl-8-chlorothiochroman 0.8 Gram (2.6 mmol) of 4,8-dichloro-5-methyl-6-ethoxycarbonylthiochroman was dissolved in 5 ml of N,N-dimethylformamide, and 0.15 ml (3.1 mmol) of ethanethiol and 0.43 g (3.1 mmol) of potassium carbonate were added. The mixture was stirred at room temperature for 2 days. After the completion of the reaction, 20 ml of water was added, and the reaction mixture was extracted with ethyl acetate twice. An organic layer was washed with water and with a saturated sodium chloride aqueous solution and dried over anhydrous sodium sulfate, and the solvent was distilled off to give 1.2 g (yield 100%) of 4-ethylthio-5-methyl-6-ethoxycarbonyl-8-chlorothiochroman.

$^1$H-NMR ppm (CDCl$_3$, TMS): δ

1.28(3H,t), 1.37(3H,t), 1.9–2.7(4H,m), 2.67(3H,s), 2.91 (1H,m), 3.75(1H,ddd), 4.2–4.4(3H,m), 7.69(1H,s)

54-4) Synthesis of 4-ethylthio-5-methyl-6-carboxy-8-chlorothiochroman 0.75 Gram (2.3 mmol) of 4-ethylthio-5-methyl-6-ethoxycarbonyl-8-chlorothiochroman, 0.47 g (7.1 mmol) of potassium hydroxide, 5 ml of ethanol and 2 ml of water were mixed, and the mixture was stirred under heat at 60° C. for 2 hours. After the completion of the reaction, the solvent was distilled off, 5 ml of water was added, and then 2N hydrochloric acid was added to adjust a pH of 1. Then, the mixture was extracted with ethyl acetate twice. An organic layer was washed with a saturated sodium chloride aqueous solution and dried over anhydrous sodium sulfate, and the solvent was distilled off to give 1.0 g (yield 100%) of 4-ethylthio-5-methyl-6-carboxy-8-chlorothiochroman.

$^1$H-NMR ppm (acetone-$d_6$, TMS): δ

1.30(3H,t), 1.9–3.1(5H,m), 2.73(3H,s), 3.79(1H,ddd), 4.24(1H,bs), 7.88(1H,s)

Preparation Example 55

3,3,5-Trimethyl-4-hydroxy-6-carboxythiochroman-1,1-dioxide 55-1) Synthesis of 3-mercapto-2,2-dimethylpropionic acid 8.0 Grams (58 mmol) of chloropivalic acid and 4.8 g (63 mmol) of thiourea were dissolved in 40 ml of ethylene glycol, and the mixture was heated at 110° C. for 4 hours. The reaction mixture was allowed to cool to room temperature, 10 g (0.25 mol/40 ml) of sodium hydroxide aqueous solution was added, and the mixture was heated under nitrogen stream at 100° C. for 30 minutes. The reaction mixture was allowed to cool to room temperature, and further cooled in an ice bath, and 5 wt % hydrochloric acid was added to adjust a pH of 1. Then, the reaction mixture was extracted with 150 ml of ethyl acetate twice. An organic layer was washed with 100 ml of 1 wt % hydrochloric acid and with 100 ml of water and dried over sodium sulfate. The solvent was distilled off, and the residue was dried under reduced pressure to give 7.2 g (yield 93%) of a yellowish oil.

$^1$H-NMR ppm (CDCl$_3$, TMS): δ

1.30(6H,s), 1.48(1H,t, J=9 Hz), 2.71(2H,d, J=9 Hz), 8.50 (1H,bs)

55-2) Synthesis of ethyl 2-methyl-4-(2-carboxy-2-methylpropylthio)-5-chlorobenzoate 7.2 Grams (54 mmol) of 3-mercapto-2,2-dimethylpropionic acid and 14 g (60 mmol) of ethyl 2-methyl-4,5-dichlorobenzoate were dissolved in 60 ml of DMF, and 12.5 g (91 mmol) of potassium carbonate was added. The mixture was heated under nitrogen stream at 100° C. for 5 hours. The reaction mixture was allowed to cool to room temperature, diluted with 200 ml of water, and washed with 100 ml of chloroform twice. An organic layer was extracted with 100 ml of a 2 wt % sodium hydroxide aqueous solution. The obtained aqueous layers were combined, and cooled in an ice bath, and 5 wt % hydrochloric acid was added to adjust a pH of 1. The mixture was extracted with 100 ml of ethyl acetate 3 times, and a combined organic layer was washed with 100 ml of 1 wt % hydrochloric acid and with 100 ml of water, and dried over sodium sulfate. The solvent was distilled off, and the residue was dried under reduced pressure to give 12.4 g (yield 69%) of a brownish solid.

$^1$H-NMR ppm (CDCl$_3$, TMS): δ

1.30–1.5(12H,m), 2.57(3H,s), 3.22(2H,s), 4.32(2H,q), 7.13(1H,s), 7.91(1H,s) 55-3) Synthesis of 3,3,5-trimethyl-6-ethoxycarbonyl-8-chlorothiochroman-4-one 12.4 Grams (38 mmol) of ethyl 2-methyl-4-(2-carboxy-2-methylpropylthio)-5-chlorobenzoate and 90 g of polyphosphoric acid were mixed, and the mixture was heated at 80° C. for 4 hours with occasional agitating. To the reaction mixture was added 50 g of ice, and the mixture was vigorously stirred. Further, 200 ml of water was added, and the mixture was extracted with 100 ml of ethyl acetate three times. An organic layer was washed with 150 ml of a saturated sodium hydrogencarbonate and dried over sodium sulfate, and the solvent was distilled off to give about 9 g of a brown oil. The oil was purified by column chromatography (silica gel/ethyl acetate+hexane=1:1) to give 6.3 g (yield 53%) of a brown oil.

$^1$H-NMR ppm (CDCl$_3$, TMS): δ

1.33(6H,s), 1.39(3H,t, J=7 Hz), 2.56(3H,s), 3.09(2H,s), 4.36(2H,q, J=7 Hz), 7.79(1H,s)

55-4) Synthesis of 3,3,5-trimethyl-6-ethoxycarbonyl-8-chlorothiochroman-4-one-1,1-dioxide 6.3 Grams (20 mmol) of 3,3,5-trimethyl-6-ethoxycarbonyl-8-chlorothiochroman-4-one was dissolved in 9 ml of acetic acid, and 6.8 g (60 mmol) of a 30 wt % hydrogen peroxide aqueous solution was added. The mixture was heated at 80° C. for 4 hours. The reaction mixture was allowed to cool, and the resultant solid was collected by filtration, washed with 200 ml of water and dried under reduced pressure to give 4.8 g (yield 70%) of a yellowish solid.

m.p.: 163~165° C.

$^1$H-NMR ppm (CDCl$_3$, TMS): δ

1.41(3H,t, J=7 Hz), 1.46(6H,s), 2.52(3H,s), 3.57(2H,s), 4.42(2H,q, J=7 Hz), 7.93(1H,s)

55-5) Synthesis of 3,3,5-trimethyl-4-hydroxy-6-carboxythiochroman-1,1-dioxide 4.6 Grams (13 mmol) of 3,3,5-trimethyl-6-ethoxycarbonyl-8-chlorothiochroman-4-one-1,1-dioxide was dissolved in 35 ml of ethanol, and 3.3 g (83 mmol/20 ml) of a sodium hydroxide aqueous solution was added. The mixture was refluxed for 30 minutes. The reaction mixture was allowed to cool to 60° C., 2.6 g (40 mg atom) of a zinc powder was added, and the mixture was heated at 60° C. for 3.5 hours. The reaction mixture was allowed to cool to room temperature, an insoluble substance was filtered off, and the filtrate was cooled in an ice bath. To the filtrate was added 5 wt % hydrochloric acid to adjust a pH of 1, and the mixture was extracted with 100 ml of ethyl acetate twice. An organic layer was washed with 50 ml of water and dried over sodium sulfate, and the solvent was distilled off. The residue was dried under reduced pressure to give 4.3 g (yield 100%) of a hygroscopic yellowish amorphous solid.

$^1$H-NMR ppm (acetone-$d_6$, TMS): δ

1.12(3H,s), 1.34(3H,s), 2.70(3H,s), 3.11(1H,d, J=14 Hz), 3.82(1H,d, J=14 Hz), 4.77(1H,s), 7.75(1H,d,J=10 Hz), 7.95(1H,d, J=10 Hz)

Preparation Example 56

3,3,5-Trimethyl-4-ethylthio-6-carboxythiochroman-1,1-dioxide 56-1) Synthesis of 3,3,5-trimethyl-4-hydroxy-6-ethoxycarbonylthiochroman-1,1-dioxide 7.4 Grams (26 mmol) of 3,3,5-trimethyl-4-hydroxy-6-carboxythiochroman-1,1-dioxide was dissolved in 70 ml of ethanol, and 1 ml of sulfuric acid was added. The mixture was refluxed for 18 hours. The reaction mixture was concentrated, and the residue was dissolved in 300 ml of ethyl acetate and washed with 50 ml of water, with 200 ml of a 2 wt % sodium hydroxide aqueous solution and with 50 ml of water in this order. An organic layer was dried over sodium sulfate, and the solvent was distilled off. The resultant brown oil was purified by column chromatography (silica gel/ethyl acetate+hexane=1:1) to give 4.1 g (yield 51%) of a brownish oil.

$^1$H-NMR ppm (CDCl$_3$, TMS): δ

1.11(3H,s), 3.07(1H,d, J=14 Hz), 3.80(1H,d, J=14 Hz), 4.40(2H,q, J=7 Hz), 4.64(1H,s), 7.80(2H,s)

56-2) Synthesis of 3,3,5-trimethyl-4-methanesulfonyloxy-6-ethoxycarbonylthiochroman-1,1-dioxide 4.1 Grams (13 mmol)of 3,3,5-trimethyl-4-hydroxy-6-ethoxycarbonylthiochroman-1,1-dioxide was dissolved in 15 ml of pyridine, and the mixture was cooled in an ice bath. 1.8 Grams (16 mmol, 1.2 eq.) of methanesulfonyl chloride was gradually added thereto. After the addition, the ice bath was removed, and the mixture was allowed to stand overnight. The reaction mixture was diluted with 200 ml of ethyl acetate, and washed with 200 ml of water, with 150 ml of a 1 wt % hydrochloric acid aqueous solution twice, with 150 ml of a saturated sodium hydrogencarbonate aqueous solution and with 50 ml of water in this order. An organic layer was dried over sodium sulfate, the solvent was distilled off, and the residue was dried under reduced pressure to give 4.9 g (yield 97%) of a brownish oil. The brownish oil solidified after allowed to stand overnight.

$^1$H-NMR ppm (CDCl$_3$, TMS): δ

1.13(3H,s), 1.41(3H,t, J=7 Hz), 1.45(3H,s), 2.73(3H,s), 2.85(3H,s), 3.23(1H,d, J=14 Hz), 3.79(IH,d, J=14 Hz), 4.41(2H,q, J=7 Hz), 5.85(1H,s), 7.96(2H,s)

56-3) Synthesis of 3,3,5-trimethyl-4-ethylthio-6-carboxythiochroman-1,1-dioxide

A methanolic solution of 0.8 g (4 mmol, 3 eq.) containing about 28 wt % sodium methoxide was diluted with 5 ml of anhydrous methanol, and 0.5 ml (6.8 mmol, 1.5 eq.) of ethanethiol was added. The mixture was stirred at room temperature for 5 minutes, and then 0.5 g (1.3 mmol) of 3,3,5-trimethyl-4-methanesulfonyloxy-6-ethoxycarbonylthiochroman-1,1-dioxide was added. The mixture was refluxed for 8 hours, and allowed to stand at room temperature for 5 days. The reaction mixture was diluted with 100 ml of ethyl acetate and washed with 50 ml of water twice, and an aqueous layer was separated and cooled in an ice bath. The aqueous layer was acidified with 5 wt % hydrochloric acid and extracted with 100 ml of ethyl acetate, and an organic layer was dried over sodium sulfate. The solvent was distilled off, and the residue was dried under reduced pressure to give 0.32 g (yield 75%) of a yellowish solid.

$^1$H-NMR ppm (CDCl$_3$, TMS); δ

1.16(3H,t, J=8 Hz), 1.26(3H,s), 1.39(3H,s), 2.4–2.5(2H, m), 2.74(3H,s), 3.16(1H,d, J=14 Hz), 3.95(1H,s), 4.11 (IH,d, J=14 Hz), 7.83(1H,d, J=9 Hz), 8.00(1H,d, J=9 Hz)

Preparation Example 57

3,4-Dehydro-5-methyl-6-carboxythiochroman-1,1-dioxide 3.0 Grams (11.8 mmol) of 4-hydroxy-5-methyl-6-carboxythiochroman-1,1-dioxide was dissolved in 10 ml of toluene, and 0.1 ml of concentrated sulfuric acid was added. The mixture was stirred under heat at 70° C. for 5 hours. After the completion of the reaction, a saturated sodium hydrogencarbonate aqueous solution was added with cooling, until the mixture showed a pH of 10. Impurities were removed by extraction with ethyl acetate, and 5 wt % hydrochloric acid was added to an aqueous layer in an ice bath to adjust a pH of 1. The mixture was extracted with ethyl acetate twice. An organic layer was washed with a saturated sodium chloride aqueous solution and dried over anhydrous sodium sulfate, and the solvent was distilled off to give 2.5 g (yield 89%) of 3,4-dehydro-5-methyl-6-carboxythiiochroman-1,1-dioxide.

m.p. 183~186° C.

$^1$H-NMR ppm (acetone-d$_6$, TMS): δ

2.62(3H,s), 4.10(2H,m), 6.45(1H,ddd), 7.20(1H,d), 7.83 (1H,d), 7.95(1H,d)

Preparation Example 58

3,4-Dichloro-5-methyl-6-carboxythiochroman-1,1-dioxide 1.6 Grams (6.7 mmol) of 3,5-dehydro-5-methylthiochroman-6-carboxy-1,1-dioxide was added to 2.1 ml (27 mmol, 4 eq.) of sulfuryl chloride, and the mixture was stirred under heat at 50° C. for 2 hours. After the completion of the reaction, 20 ml of water was added, and the mixture was extracted with ethyl acetate twice. An organic layer was washed with a saturated sodium chloride aqueous soltuion and then dried over anhydrous sodium sulfate, and the solvent was distilled off to give 1.9 g (yield 100%) of 3,4-dichloro-5-methyl-6-carboxythiochroman-1,1-dioxide.

m.p.: 236~244° C.

$^1$H-NMR ppm (acetone-d$_6$, TMS): δ

2.73(3H,s), 4.0–4.4(2H,m), 5.32(1H,m), 5.92(1H,d), 7.86 (1H,d), 8.08(1H,d)

Preparation Example 59

4-Acetamide-5-methyl-6-carboxythiochroman-1,1-dioxide

3Milliliters of concentrated sulfuric acid was cooled in an ice bath, 2 ml (38 mmol) of acetonitrile was gradually added, and then 1.4 g (5.5 mmol) of 4-hydroxy-5-methyl-6-carboxythiochroman-1,1-dioxide was added portionwise. The ice bath was removed, and the reaction mixture was stirred at 40° C. for 4.5 hours. The viscous reaction mixture was allowed to cool to room temperature, 5 g of ice was added and then 30 ml of water was added. The mixture was extracted with 50 ml of ethyl acetate twice. An organic layer was washed with 50 ml of water and dried over sodium sulfate, and the solvent was distilled off. The residue was dried under reduced pressure to give 1.4 g (yield 86%) of a white solid.

$^1$H-NMR ppm (acetone-d$_6$, TMS): δ

1.96(3H,s), 2.48(3H,s), 2.3–2.7(2H,m), 3.2–3.9(2H,m), 5.42(1H,m), 7.77(1H,d, J=8 Hz), 7.94(1H,d, J=8 Hz)

Preparation Example 60

4-Chloro-5-methyl-6-(1-ethyl-5-hydroxypyrazol-4-yl)carbonylthiochroman-1,1-dioxide 0.9 Gram (2.4 mmol) of 4-chloro-5-methyl-6-(1-ethylpyrazol-5-yl)oxycarbonylthiochroman-1,1-dioxide was dissolved in 10 ml of acetonitrile, and 0.33 g (2.4 mmol) of potassium carbonate and 0.1 ml of acetonecyanhydrin were added. The mixture was stirred at room temperature for 1 day. After the completion of the reaction, the solvent was distilled off. The remaining oil was dissolved in ethyl acetate, and product was extracted with a 5 wt % sodium hydrogencarbonate aqueous solution. 2N Hydrochloric acid was added to the resultant aqueous solution in an ice bath to adjust a pH of 1, and the mixture was extracted with ethyl acetate. An organic layer was washed with a saturated sodium chloride aqueous solution and dried over anhydrous sodium sulfate, and the solvent was distilled off to give 0.8 g (yield 89%) of 4-chloro-5-methyl-6-(1-ethyl-5-hydroxypyrazol-4-yl)carbonylthiochroman-1,1-dioxide.

m.p.: 175~176° C.

$^1$H-NMR ppm (acetone-d$_6$, TMS): δ

1.37(3H,t), 2.50(3H,s), 2.5–4.0(4H,m), 4.05(2H,q), 5.79 (1H,bs), 7.38(1H,s), 7.66(1H,d), 7.89(1H,d)

IRcm$^{-1}$(KBr): 3250, 3000, 1640, 1540, 1310, 1300, 1120

Preparation Example 61

4-Chloro-5-methyl-6-(1-ethyl-5-n-propanesulfonyloxy-pyrazol-4-yl)carbonylthiochroman-1,1-dioxide 0.26 Gram (0.7 mmol) of 4-chloro-5-methyl-6-(1-ethyl-5-hydroxypyrazol-4-yl)carbonylthiochroman-1,1-dioxide was dissolved in 3 ml of methylene chloride, and then a solution of 0.2 g (1.4 mmol) of potassium carbonate in 2 ml of water was added. Further, 0.16 ml (1.4 mmol) of n-propanesulfonyl chloride and 20 mg (0.08 mmol) of benzyltriethylammonium chloride were added, and the mixture was allowed to react at room temperature for 1 day. After the completion of the reaction, a methylene chloride layer was separated and dried over anhydrous sodium sulfate, and the solvent was distilled off under reduced pressure to give 0.2 g (yield 60%) of 4-chloro-5-methyl-6-(1-ethyl-5-n-propanesulfonyloxypyrazol-4-yl)carbonylthiochroman-1,1-dioxide.

$^1$H-NMR ppm (CDCl$_3$, TMS): δ

1.18(3H,t), 1.52(3H,t), 2.12(2H,m), 2.48(3H,s), 2.6–4.2 (6H,m), 4.22(2H,q), 5.47(1H,t), 7.44(1H,s), 7.51(1H, d), 7.92(1H,d)

IRcm$^{-1}$(KBr): 2950, 1650, 1540, 1380, 1280, 1160, 1120

Preparation Example 62

4-Ethylthio-5-methyl-6-(1-ethyl-5-hydroxypyrazol-4-yl)carbonylthiochroman-1,1-dioxide 0.51 Gram (1.7 mmol) of 4-ethylthio-5-methyl-6-carboxythiochroman-1,1-dioxide was dissolved in 5 ml of t-amyl alcohol, and 0.22 g (2.0 mmol, 1.2 eq.) of 1-ethyl-5-hydroxypyrazole and 0.42 g (2.0 mmol, 1.2 eq.) of N,N'-dicyclohexylcarbodiimide were added. The mixture was stirred at room temperature for 3 hours, and then 0.18 g (1.3 mmol) of potassium carbonate was added. The mixture was heated at 80° C. for 8 hours. After the completion of the reaction, the solvent was distilled off. The remaining oil was dissolved in ethyl acetate and product was extracted with a 5 wt % sodium hydrogencarbonate aqueous solution. 2N Hydrochloric acid was added to the resultant aqueous solution to adjust a pH of 1, and the mixture was extracted with ethyl acetate. An organic layer was washed with a saturated sodium chloride aqueous solution and dried over anhydrous sodium sulfate, and the solvent was distilled off to give 0.5 g (75%) of 4-ethylthio-5-methyl-6-(1-ethyl-5-hydroxypyrazol-4-yl)carbonylthiochroman-1,1-dioxide.

m.p.: 150~152° C.

$^1$H-NMR ppm (acetone-d$_6$, TMS): δ

1.33(3H,t), 1.39(3H,t), 2.68(3H,s), 2.6–3.0(4H,m), 3.42 (1H,m), 4.04(2H,q), 4.0–4.4(1H,m), 4.59(1H,t), 5.94 (1H,bs), 7.33(1H,s), 7.57(1H,d), 7.80(1H,d)

IRcm$^{-1}$(KBr): 3400, 1640, 1330, 1300, 1120

Preparation Example 63

4-Ethylthio-5-methyl-6-(1-ethyl-5-n-propanesulfonyloxypyrazol-4-yl)carbonylthiochroman-1,1-dioxide 0.27 Gram (0.7 mmol) of 4-ethylthio-5-methyl-6-(1-ethyl-5-hydroxypyrazol-4-yl)carbonylthiochroman-1,1-dioxide was dissolved in 3 ml of methylene chloride, and then a solution of 0.2 g (1.4 mmol) of potassium carbonate in 2 ml of water was added. Further, 0.16 ml (1.4 mmol) of n-propanesulfonyl chloride and 20 mg (0.08 mmol) of benzyltriethylammonium chloride were added, and the mixture was allowed to react at room temperature for 1 day. After the completion of the reaction, a methylene chloride layer was separated and dried over anhydrous sodium sulfate, and the solvent was distilled off under reduced pressure to give 0.21 g (yield 60%) of 4-ethylthio-5-methyl-6-(1-ethyl-5-n-propanesulfonyloxypyrazol-4-yl)carbonylthiochroman-1,1-dioxide.

m.p.: 140~145° C.

$^1$H-NMR ppm (CDCl$_3$, TMS): δ1.17(3H,t), 1.33(3H,t), 1.51(3H,t), 1.8–2.3(2H,m), 2.51(3H,s), 2.5–3.8(7H,m), 4.0–4.5(4H,m), 7.44(1H,d), 7.45(1H,s), 7.86(1H,d)

IRcm$^{-1}$(KBr): 3000, 1660, 1340, 1390, 1300, 1170

Preparation Example 64

4-Ethylthio-5-methyl-6-(1-ethyl-5-n-propanesulfonyloxypyrazol-4-yl)carbonyl-8-chlorothiochroman 64-1) Synthesis of 4-ethylthio-5-methyl-6-(1-ethylpyrazol-5-yl)oxycarbonyl-8-chlorothiochroman 1.0 Gram (3.3 mmol) of 4-ethylthio-5-methyl-6-carboxy-8-chlorothiochroman was dissolved in 5 ml of t-amyl alcohol, and 0.45 g (4.0 mmol, 1.2 eq.) of 1-ethyl-5-hydroxypyrazole and 0.83 g (4.0 mmol, 1.2 eq.) of N,N'-dicyclohexylcarbodiimide were added. The mixture was stirred at room temperature for 2.5 hours. After the completion of the reaction, ethyl acetate and hexane were added, and liberated N,N'-dicyclohexylurea was filtered off. The filtrate was concentrated and purified by column chromatography (silica gel/hexane+ethyl acetate=5:1) to give 1.4 g (yield 100%) of 4-ethylthio-5-methyl-6-(1-ethylpyrazol-5-yl)oxycarbonyl-8-chlorothiochroman.

$^1$H-NMR ppm (CDCl$_3$, TMS): δ1.36(3H,t), 1.44(3H,t), 1.9–3.1(5H,m), 2.75(3H,m), 3.78(1H,ddd), 4.07(2H,q), 4.35(1H,bs), 6.16(1H,d), 7.46(1H,d), 7.92(1H,s)

64-2) Synthesis of 4-ethylthio-5-methyl-6-(1-ethyl-5-n-propanesulfonyloxypyrazol-4-yl)carbonyl-8-chlorothiochroman 1.4 Grams (3.5 mmol) of 4-ethylthio-5-methyl-6-(1-ethypyrazol-5-yl)oxycarbonyl-8-chlorothiocrhoman was dissolved in 5 ml of acetonitrile, and 1.0 ml (7.0 mmol, 1.2 eq.) of triethylamine and 0.1 ml of acetonecyanhydrin were added. The mixture was stirred at room temperature for 2 days. After the completion of the reaction, the solvent was distilled off. The remaining oil was dissolved in ethyl acetate and extracted with a 5 wt % sodium hydrogencarbonate aqueous solution. 2N Hydrochloric acid was added to the resultant aqueous solution in an ice bath to adjust a pH of 1, and the mixture was extracted with ethyl acetate. An organic layer was washed with a saturated sodium chloride aqueous solution and dried over anhydrous sodium sulfate, and the solvent was distilled off. The remaining oil was dissolved in 5 ml of methylene chloride, and then a solution of 0.97 g (7.0 mmol) of potassium carbonate in 3 ml of water was added. Further, 0.8 ml (7.0 mmol) of n-propanesulfonyl chloride and 20 mg (0.08 mmol) of benzyltriethylammonium chloride were added, and the mixture was allowed to react at room temperature for 1 day. After the completion of the reaction, an methylene chloride layer was separated and dried over anhydrous sodium sulfate, and the solvent was distilled off under reduced pressure to give 1.1 g (yield 63%) of 4-ethylthio-5-methyl-6-(1-ethyl-5-n-propanesulfonyloxypyrazol-4-yl)carbonyl-8-chlorothiochroman.

$^1$H-NMR ppm (CDCl$_3$, TMS): δ

1.15(3H,t), 1.30(3H,t), 1.51(3H,t), 1.8–3.2(7H,m), 2.45 (3H,s), 3.4–4.0(3H,m), 4.0–4.5(3H,m), 7.26(1H,s), 7.57(1H,s)

IRcm$^{-1}$(KBr): 3000, 1660, 1550, 1440, 1380, 1180

Preparation Example 65

3,3,5-Trimethyl-4-chloro-6-[(1-ethyl-5-hydroxypyrazol-4-yl)carbonyl]thiochroman-1,1-dioxide 65-1) Synthesis of 3,3,5-trimethyl-4-chloro-6-(1-ethylpyrazol-5-yloxycarbonyl)-thiochroman-1,1-doxide 1.5 Grams (5.3 mmol) of 3,3,5-trimethyl-4-hydroxy-6-carboxythiochroman-1,1-dioxide was dissolved in 8 ml of thionyl chloride, and the mixture was refluxed for 4 hours. The reaction mixture was diluted with 50 ml of carbon tetrachloride, and the solvent was distilled off. The residue was dried under reduced pressure with an aspirator, to give an acid chloride in the form of a black semi-solid. 0.75 Gram (6.7 mmol) of 1-ethyl-5-hydroxypyrazole and 0.67 g (6.8 mmol) of triethylamine were dissolved in 20 ml of THF and cooled in an ice bath. A solution of the above-prepared acid chloride in 15 ml of THF was dropwise added thereto over 10 minutes. The reaction mixture was stirred at room temperature for 4 hours, and then allowed to stand overnight. The reaction mixture was diluted with 150 ml of ethyl acetate, and an insoluble solid was filtered off. The filtrate was washed with 100 ml of water twice, and an organic layer was dried over sodium sulfate. The solvent was distilled off, and about 1.9 g of the resultant brown oil was purified by column chromatography (silica gel/ethyl acetate+hexane= 1:1) to give 0.82 g (yield 39%) of a yellowish amorphous solid.

$^1$H-NMR ppm (CDCl$_3$, TMS): δ

1.33–1.53(9H,m), 2.77(3H,s), 3.20(1H,d, J=14 Hz), 3.9–4.2(3H,m), 5.04(1H,s), 6.26(1H,s), 7.48(1H,s), 7.93(1H,d, J=8 Hz), 65-2) Synthesis of 3,3,5-trimethyl-4-chloro-6-[(1-ethyl-5-hydroxypyrazol-4-yl)carbonyl]thiochroman-1,1-dioxide 0.8 Gram (2.0 mmol) of 3,3,5-trimethyl-4-chloro-6-(1-ethylpyrazol-5-yloxycarbonyl)-thiochroman-1,1-dioxide and 0.24 g (2.4 mmol) of triethylamine were dissolved in 10 ml of acetonitrile, and five drops of acetonecyanhydrin were added. The mixture was stirred at room temperature for 8 hours, and allowed to stand overnight. The reaction mixture was concentrated with an evaporator, and the residue was dissolved in water and cooled in an ice bath. 5 wt % Hydrochloric acid was added to adjust a pH of 2, and the mixture was extracted with 80 ml of ethyl acetate twice. An organic layer was washed with 50 ml of 1 wt % hydrochloric acid and with 50 ml of water and dried over sodium sulfate, and the solvent was distilled off to give a mixture of a white solid with a yellowish oil. The mixture was washed with a small amount of ethyl acetate+hexane (=1:1) to give 0.36 g (yield 45%) of a white solid.

m.p.: 156~160° C.

$^1$H-NMR ppm (CDCl$_3$, TMS): δ

1.34(3H,s), 1.44(1H,s), 1.45(3H,d, J=7 Hz), 2.54(3H,s), 3.19(1H,d, J=13 Hz), 4.00(1H,d, J=13 Hz), 4.10(2H,q, J=7 Hz), 5.00(1H,s), 7.34(1H,s), 7.61(1H,d, J=8 Hz), 7.93(1H,d, J=8 Hz)

IRcm$^{-1}$(KBr): 3400, 3000, 1750, 1640, 1310,

FDMS:found m/z=396(M$^+$,100), 794(1) (calcd for C$_{18}$H$_{21}$N$_2$O$_4$SCl=396)

Preparation Example 66

3,3,5-Trimethyl-4-ethylthio-6-[(1-ethyl-5-hydroxypyrazol-4-yl)carbonyl]thiochroman-1,1-dioxide 66-1) Synthesis of 3,3,5-trimethyl-4-ethylthio-6-(1-ethylpyrazol-4-yloxycarbonyl)thiochroman-1,1-dioxide 0.32 Gram (0.98 mmol) of 3,3,5-trimethyl-4-ethylthio-6-carboxythiochroman-1,1-dioxide was suspended tin 3 ml of 1,2-dichlorethane, and 0.2 ml (2.7 mmol, 3 eq.) of thionyl chloride was added. The mixture was stirred at 70° C. for 3 hours. The solvent was distilled off from the reaction mixture, and the residue was dissolved in 50 ml of carbon tetrachloride. The solvent was further distilled off, and unreacted thionyl chloride was completely removed to give an acid chloride in the form of a yellowish oil.

0.14 Gram (1.3 mmol, 1.3 eq.) of 1-ethyl-5-hydroxypyrazole and 0.13 g (1.3 mmol, 1.3 eq.) of triethylamine were dissolved in 3 ml of THF and cooled in an ice bath. A solution of the above-prepared acid chloride in 1 ml of THF was dropwise added thereto. The reaction mixture was stirred at room temperature for 3 hours, and then allowed to stand at room temperature overnight. The reaction mixture was diluted with 100 ml of ethyl acetate and washed with 50 ml of water, with 50 ml of a sodium hydrogencarbonate aqueous solution and with 50 ml of water in this order, and an organic layer was dried over sodium sulfate. The solvent was distilled off, and the resultant brownish oil was purified by column chromatography (silica gel/acetic acid+hexane=1:1) to give 0.15 g (yield 36%) of a white paste. The paste become a white solid when allowed to stand at room temperature overnight.

$^1$H-NMR ppm (CDCl$_3$, TMS): δ

1.1–1.5(12H,m), 2.4–2.7(2H,m), 2.76(3H,s), 3.16(1H,d, J=14 Hz), 3.9–4.2(4H,m), 6.27(1H,d, J=2 Hz), 7.50 (1H,d, J=2 Hz), 7.90(1H,d J=9 Hz), 8.06(1H,d, J=9 Hz)

66-2) Synthesis of 3,3,5-trimethyl-4-ethylthio-6-[(1-ethyl-5-hydroxypyrazol-4-yl)carbonyl]thiochroman-1,1-dioxide 0.15 Gram (0.36 mmol) of 3,3,5-trimethyl-4-ethylthio-6-(1-ethylpyrazol-4-yloxycarbonyl)thiochroman-1,1-dioxide and 0.04 g (0.4 mmol, 1.1 eq.) of triethylamine were dissolved in 2 ml of acetonitrile, and 3 drops of acetonecyanhydrin was added. The mixture was stirred at room temperature for 30 minutes and allowed to stand overnight. The solvent was distilled off from the reaction mixture, and the residue was dissolved in 20 ml of water and cooled in an ice bath. The mixture was adjusted to a pH of 2 by adding 5 wt % Hydrochloric acid, and a formed solid was collected by filtration, washed with water and dried under reduced pressure to give 0.10 g (yield 66%) of a white solid.

m.p.: 73~77° C.

$^1$H-NMR ppm (CDCl$_3$, TMS): δ

1.1–1.5(12H,m), 2.4–2.6(m), 2.52(s) (total 5H), 3.14(1H, d, J=14 Hz), 3.9–4.2(4H,m), 7.32(1H,s), 7.52(1H,d, J=8 Hz), 7.88(1H,d, J=8 Hz)

IRcm$^{-1}$(KBr): 3000, 1730, 1630, 1300

Preparation Example 67

3,4-Dichloro-5-methyl-6-(1-ethyl-5-n-propanesulfonyloxypyrazol-4-yl) carbonylthiochroman-1,1-dioxide 67-1) Synthesis of 3,4-dichloro-5-methyl-6-(1-ethylpyrazol-5-yl)oxycarbonylthiochroman-1,1-dioxide 1.5 Grams (4.9 mmol) of 3,4-dichloro-5-methyl-6-carboxythiochroman-1,1-dioxide was dissolved in 5 ml of t-amyl alcohol, and 1.1 g (5.3mmol, 1.2 eq.) of 1-ethyl-5-hydroxypyrazole and 1.1 g (5.3 mmol, 1.2 eq.) of N,N'-dicyclohexylcarbodiimide were added. The mixture was stirred at room temperature for 2.5 hours. After the completion of the reaction, the reaction mixture was extracted with ethyl acetate and hexane, and liberated N,N'-dicyclohexylurea was filtered off. An organic layer was concentrated under reduced pressure and purified by column chromatography (silica gel/ethyl acetate) to give 1.9 g (yield 95%) of 3,4-dichloro-5-methyl-6-(1-ethylpyrazol-5-yl)oxycarbonylthiochroman-1,1-dioxide.

$^1$H-NMR ppm (CDCl$_3$, TMS): δ

1.43(3H,t), 2.77(3H,s), 3.7–4.3(4H,m), 5.04(1H,ddd), 5.60(1H,d), 6.28(1H,d), 7.47(1H,d), 7.92(1H,s), 8.18(1H,d)

67-2) Synthesis of 3,4-dichloro-5-methyl-6-(1-ethyl-5-hydroxypyrazol-4-yl)carbonylthiochroman-1,1-dioxide 1.9 Grams (4.7 mmol) of 3,4-dichloro-5-methyl-6-(1-ethylpyrazol-5-yl)oxycarbonylthiochroman-1,1-dioxide was dissolved in 5 ml of acetonitrile, and 0.65 g (4.7 mmol, 1 eq.) of potassium carbonate and 0.1 ml of acetonecyanhydrin were added. The mixture was stirred at room temperature for 1 day. After the completion of the reaction, the solvent was distilled off. The remaining oil was dissolved in ethyl acetate, and the product was extracted with a 5 wt % sodium hydrogencarbonate aqueous solution. The aqueous layer was adjusted to a pH of 1 in an ice bath by adding 2N hydrochloric acid, and extracted with ethyl acetate. An organic layer was washed with a saturated sodium chloride aqueous solution and then dried over anhydrous sodium sulfate, and the solvent was distilled off to give 1.1 g (yield 57%) of 3,4-dichloro-5-methyl-6-(1-ethyl-5-hydroxypyrazol-4-yl) carbonylthiochroman-1,1-dioxide.

$^1$H-NMR ppm (acetone-d$_6$, TMS): δ

1.39(3H,t), 2.54(3H,s), 3.8–4.3(4H,m), 5.30(1H,m), 5.90(1H,d), 7.32(1H,s), 7.72(1H,d), 7.89(1H,d)

IRcm$^{-1}$(KBr): 3250, 2950, 1620, 1520, 1300, 1120, 780

67-3) Synthesis of 3,4-dichloro-5-methyl-6-(1-ethyl-5-n-propanesulfonyloxypyrazol-4-yl)carbonylthiochroman-1,1-dioxide 1.1 Grams (2.7 mmol) of 3,4-dichloro-5-methyl-6-(1-ethyl-5-hydroxypyrazol-4-yl)carbonylthiochroman-1,1-dioxide was dissolved in 5 ml of methylene chloride, and then a solution of 0.65 g (4.7 mmol) of potassium carbonate in 3 ml of water was added. Further, 0.5 ml of (4.7 mmol) of n-propanesulfonyl chloride and 20 mg (0.08 mmol) of benzyltriethylammonium chloride were added, and the mixture was allowed to react at room temperature for 1 day. After the completion of the reaction, a methylene chloride layer was separated, and dried over anhydrous sodium sulfate, and then the solvent was distilled off under reduced pressure to give 1.2 g (yield 50%) of 3,4-dichloro-5-methyl-6-(1-ethyl-5-n-propanesulfonyloxypyrazol-4-yl) carbonylthiochroman-1,1-dioxide.

$^1$H-NMR ppm (CDCl$_3$, TMS): δ

1.18(3H,t), 1.52(3H,t), 1.9–2.3(2H,m), 2.48(3H,s), 3.6–3.9(2H,m), 4.1–4.4(4H,m), 5.08(1H,ddd), 5.52(1H,d), 7.43(1H,s), 7.57(1H,d), 7.90(1H,d)

IRcm$^{-1}$(KBr): 2950, 1680, 1550, 1380, 1300, 1170, 1130, 820

Preparation Example 68

4-N-Methylamino-5-methyl-6-(1-ethyl-5-hydroxypyrazol-4-yl)carbonylthiochroman-1,1-dioxide, methylamine salt 0.8 Gram (2.2 mmol) of 4-chloro-5-methyl-6-(1-ethyl-5-hydroxypyrazol-4-yl)carbonylthiochroman-1,1-dioxide was dissolved in 1.2 ml of methanol, and 1.2 ml (11 mmol, 5 eq.) of methanol solution of a 40 wt % methylamine was added with stirring at room temperature. The mixture was stirred at a reaction temperature of 50° C. for 4 hours. After the completion of the reaction, the reaction mixture was distilled under reduced pressure to give 1.0 g (yield 100%) of 4-N-methylamino-5-methyl-6-(1-ethyl-5-hydroxypyrazol-4-yl)carbonylthiochroman-1,1-dioxide, methylamine salt.

$^1$H-NMR ppm (acetone-d$_6$, TMS): δ

1.20(3H,t), 2.36(3H,t), 2.48(3H,s), 2.0–3.0(3H,m), 6.81(1H,s), 7.32(1H,d), 7.68(1H,d)

IRcm$^{-1}$(KBr): 3600~2300, 1620, 1290, 1130

Preparation Example 69

4-N-Methylamino-5-methyl-6-(1-ethyl-5-n-propanesulfonyloxypyrazol-4-yl) carbonylthiochroman-1,1-dioxide 0.66 Gram (1.7 mmol) of 4-N-methylamino-5-methyl-6-(1-ethyl-5-hydroxypyrazol-4-yl)carbonylthiochroman-1,1-dioxidemethylamine salt was dissolved in 3 ml of methylene chloride, and then 0.75 g (5.4 mmol) of potassium carbonate and 2 ml of water were added. Further, 0.6 ml (5.4 mmol) of n-propanesulfonyl chloride and 20 mg (0.08 mmol) of benzyltriethylammonium chloride were added, and the mixture was allowed to react at room temperature for 1 day. After the completion of the reaction, a methylene chloride layer was recovered and dried over anhydrous sodium sulfate, and the solvent was distilled off to give 0.36 g (yield 43%) of 4-N-methylamino-5-methyl-6-(1-ethyl-5-n-propanesulfonyloxypyrazol-4-yl)carbonylthiochroman-1,1-dioxide.

$^1$H-NMR ppm (CDCl$_3$, TMS): δ

1.17(3H,t), 1.50(3H,t), 2.05(2H,m), 2.3–2.6(2H,m), 2.40(3H,s), 2.50(3H,s), 3.20(1H,m), 3.64(2H,m), 3.8–4.0(2H,m), 4.20(2H,q), 7.44(1H,d), 7.46(1H,s), 7.85(1H,d)

IRcm$^{-1}$(KBr): 3350, 2950, 1720, 1640, 1530, 1360, 1250, 1160

Preparation Example 70

4-(N-Methyl-N-methoxycarbonylamino)-5-methyl-6-(1-ethyl-5-n-propanesulfonyloxypyrazol-4-yl) carbonylthiochroman-1,1-dioxide 0.21 Gram (0.45 mmol) of 4-N-methylamino-5-methyl-6-(1-ethyl-5-n-propanesulfonyloxypyrazol-4-yl)

carbonylthiochroman-1,1-dioxide was dissolved in 2 ml of methylene chloride, and 0.07 ml (0.9 mmol, 2 eq.) of pyridine was added. Then, while the mixture was cooled with ice, 0.07 ml (0.09 mmol, 1 eq.) of methyl chloroformate was added with stirring. The mixture was stirred at room temperature for 3 hours, and a methylene chloride layer was separated and washed with 2N hydrochloric acid and with a saturated sodium chloride aqueous solution. Then, the methylene chloride layer was dried over anhydrous sodium sulfate, and the solvent was distilled off to give 0.13 g (yield 55%) of 4-(N-methyl-N-methoxycarbonylamino)-5-methyl-6-(1-ethyl-5-n-propanesulfonyloxypyrazol-4-yl) carbonylthiochroman-1,1-dioxide.

m.p.: 156~159° C.

$^1$H-NMR ppm (CDCl$_3$, TMS): δ

1.19(3H,t), 1.51(3H,t), 2.15(2H,m), 2.18(3H,s), 2.60(3H, s), 2.5–2.7(2H,m), 3.40(2H,m), 3.75(2H,m),3.76(3H, s), 4.21(2H,q), 5.76(1H,t), 7.35(1H,s), 7.50(1H,d), 7.98 (1H,d)

IRcm$^{-1}$(KBr): 2950, 1660, 1280, 1180, 1160, 1120

Preparation Example 71

4-(N-Methylcarbamoyl)oxy-5-methyl-6-(1-ethyl-5-n-propanesulfonyloxypyrazol-4-yl) carbonylthiochroman-1,1-dioxide 71-1) Synthesis of 4-hydroxy-5-methyl-6-(1-ethyl-5-hydroxypyrazol-4-yl)carbonylthiochroman-1,1-dioxide 2.0 Grams (7.8 mmol) of 4-hydroxy-6-carboxy-5-methylthiochroman-1,1-dioxide was dissolved in 10 ml of t-amyl alcohol, and 1.0 g (8.6 mmol, 1.1 eq.) of 1-ethyl-5-hydroxypyrazole and 1.8 g (8.6 mmol, 1.1 eq.) of N,N'-dicyclohexylcarbodiimide were added. The mixture was stirred at room temperature for 3 hours. Then, 0.8 g (5.9 mmol) of potassium carbonate was added. The mixture was heated at 80° C. for 6 hours. After the completion of the reaction, the solvent was distilled off. The remaining oil was dissolved in ethyl acetate, and end product was extracted with a 5 wt % sodium hydrogencarbonate aqueous solution. The resultant aqueous solution was adjusted to a pH of 1 in an ice bath by adding 2N hydrochloric acid, and extracted with ethyl acetate. An organic layer was washed with a saturated sodium chloride aqueous solution and dried over anhydrous sodium sulfate, and the solvent was distilled off to give 2.0 g (yield 73%) of 4-hydroxy-5-methyl-6-(1-ethyl-5-hydroxypyrazol-4-yl)carbonylthiochroman-1,1-dioxide.

$^1$H-NMR ppm (acetone-d$_6$, TMS): δ

1.39(3H,t), 2.50(3H,s), 2.5–2.8(2H,m), 3.30(1H,m), 3.7–4.0(1H,m), 4.05(2H,q), 5.20(2H,t), 7.34(1H,s), 7.59(1H,d), 7.81(1H,d)

71-2) Synthesis of 4-(N-methylcarbamoyl)oxy-5-methyl-6-(1-ethyl-5-n-propanesulfonyloxypyrazol-4-yl) carbonylthiochroman-1,1-dioxide 0.63 Gram (1.8 mmol) of 4-hydroxy-5-methyl-6-(1-ethyl-5-hydroxypyrazol-4-yl)carbonylthiochroman-1,1-dioxide was dissolved in 5 ml of THF, and 0.75 g (5.4 mmol, 3 eq.) of sodium carbonate, 0.32 ml (5.4 mmol, 3 eq) of methyl isocyanate and 20 mg of 18-crown-6 were added. The mixture was stirred under heat at 40° C. for 1 hour. After the completion of the reaction, the reaction mixture was adjusted to a pH of 1 by adding 2N hydrochloric acid and extracted with ethyl acetate twice. An organic layer was washed with a saturated sodium chloride aqueous solution and dried over anhydrous sodium sulfate, and the solvent was distilled off.

The remaining oil was dissolved in 5 ml of methylene chloride, and a solution of 0.5 g (3.6 mmol) of potassium carbonate in 2 ml of water was added. Further, 0.4 ml (3.6mmol) of n-propanesulfonyl chloride and 20 mg (0.08 mmol) of benzyltriethylammonium chloride were added, and the mixture was allowed to react at room temperature for 1 day. After the completion of the reaction, a methylene chloride layer was separated and dried over anhydrous sodium sulfate, and the solvent was distilled off under reduced pressure to give 0.57 g (yield 60%) of 4-(N-methylcarbamoyl)oxy-5-methyl-6-(1-ethyl-5-n-propanesulfonyloxypyrazol-4-yl)carbonylthiochroman-1,1-dioxide.

$^1$H-NMR ppm (CDCl$_3$, TMS): δ

1.17(3H,t), 1.50(3H,t), 1.9–2.3(2H,m), 2.29(3H,s), 2.5–3.5(7H,m), 3.71(2H,m), 4.21(2H,q), 4.85(1H,m), 6.10(1H,bs), 7.40(1H,s), 7.52(1H,d), 7.90(1H,d)

IRcm$^{-1}$(KBr): 2970, 1720, 1650, 1370, 1300, 1240, 1160, 1120

Tables 28 and 29 show the thiochroman carboxylic acids obtained in Preparation Examples 52 to 59 and the pyrazole derivatives obtained in Preparation Examples 60 to 71 in a manner in which the carboxylic acids correspond to the pyrazole derivatives.

TABLE 28

| thiochroman carboxylic acid | | pyrazole derivative | | |
|---|---|---|---|---|
| Ex. No. | structure | Ex. No. | structure | Comp'd No. |
| 52 | (structure) | 60 | (structure) | 36 |

TABLE 28-continued

| thiochroman carboxylic acid | | pyrazole derivative | | |
|---|---|---|---|---|
| Ex. No. | structure | Ex. No. | structure | Comp'd No. |
| | | 61 | (4-Cl, 5-CH₃ thiochroman-SO₂, 6-yl C(O)- pyrazole with N-Et, 5-O-SO₂ⁿPr) | 37 |
| 53 | 4-SEt, 5-CH₃ thiochroman-SO₂, 6-COOH | 62 | 4-SEt, 5-CH₃ thiochroman-SO₂, 6-yl C(O)- pyrazole N-Et, 5-OH | 38 |
| | | 63 | 4-SEt, 5-CH₃ thiochroman-SO₂, 6-yl C(O)- pyrazole N-Et, 5-O-SO₂ⁿPr | 39 |
| 54 | 4-SEt, 5-CH₃, 8-Cl thiochroman-S, 6-COOH | 64 | 4-SEt, 5-CH₃, 8-Cl thiochroman-S, 6-yl C(O)- pyrazole N-Et, 5-O-SO₂ⁿPr | 40 |
| 55 | 4-OH, 3,3-diCH₃, 5-CH₃ thiochroman-SO₂, 6-COOH | 65 | 4-Cl, 3,3-diCH₃, 5-CH₃ thiochroman-SO₂, 6-yl C(O)- pyrazole N-Et, 5-OH | 41 |
| 56 | 4-SEt, 3,3-diCH₃, 5-CH₃ thiochroman-SO₂, 6-COOH | 66 | 4-SEt, 3,3-diCH₃, 5-CH₃ thiochroman-SO₂, 6-yl C(O)- pyrazole N-Et, 5-OH | 42 |
| 57 | 5-CH₃ thiochromene-SO₂, 6-COOH | 67 | 3,4-diCl, 5-CH₃ thiochroman-SO₂, 6-yl C(O)- pyrazole N-Et, 5-O-SO₂ⁿPr | 43 |

TABLE 28-continued

| | thiochroman carboxylic acid | | pyrazole derivative | |
|---|---|---|---|---|
| Ex. No. | structure | Ex. No. | structure | Comp'd No. |
| 58 | 5-methyl-3,4-dichloro-thiochroman-1,1-dioxide-6-carboxylic acid | | | |

TABLE 29

| | thiochroman carboxylic acid | | pyrazole derivative | |
|---|---|---|---|---|
| Ex. No. | structure | Ex. No. | structure | Comp'd No. |
| 59 | 4-(NHCOCH$_3$)-5-methyl-thiochroman-1,1-dioxide-6-carboxylic acid | 68 | 1-Et, 5-O⁻ CH$_3$NH$_3$⁺ pyrazole-4-carbonyl linked to 5-methyl-4-NHCH$_3$-thiochroman-1,1-dioxide | 44 |
| | | 69 | 1-Et, 5-OSO$_2$$^n$Pr pyrazole-4-carbonyl linked to 5-methyl-4-NHCH$_3$-thiochroman-1,1-dioxide | 45 |
| | | 70 | 1-Et, 5-OSO$_2$$^n$Pr pyrazole-4-carbonyl linked to 5-methyl-4-N(CH$_3$)CO$_2$CH$_3$-thiochroman-1,1-dioxide | 46 |
| | | 71 | 1-Et, 5-OSO$_2$$^n$Pr pyrazole-4-carbonyl linked to 5-methyl-4-OCONHCH$_3$-thiochroman-1,1-dioxide | 47 |

Preparation Example 72

4-Methoxymethyl-5,8-dimethyl-6-carboxythiochroman-1,1-dioxide 72-1) Synthesis of 6-bromo-4-(trimethylsiloxy)-4-cyano-5,8-dimethylthiochroman To a mixture of 2.50 g (9.22 mmol) of 6-bromo-5,8-dimethylthiochroman-4-one with 0.15 g (0.46 mmol) of zinc iodide was added 4.60 ml (36.9 mmol) of trimethylsilyl cyanide under nitrogen atmosphere. The mixture was stirred at room temperature for 2 days. The reaction mixture was diluted with chloroform and washed with a sodium hydrogencarbonate aqueous solution. An organic layer was dried over anhydrous sodium sulfate and filtered, and the solvent was distilled off to give 3.53 g of the titled compound as a crude product.

$^1$H-NMR ppm (CDCl$_3$, TMS): δ0.26(3H,s), 2.20(3H,s), 2.72(3H,s), 2.7–2.9(2H,m), 3.0–3.2(2H,m), 7.36(1H,s)

72-2)Synthesis of 5,8-dimethyl-4-carboxythiochroman

A mixture containing 3.00 g (8.10 mol) of 6-bromo-4-(trimethylsiloxy)-4-cyano-5,8-dimethylthiochroman, 7.31 g (32.4 mmol) of tin(II) chloride dihydrate, 20 ml of acetic acid and 20 ml of concentrated hydrochloric acid was allowed to react at reflux under heat for 57 hours under nitrogen atmosphere. The reaction mixture was cooled to room temperature and diluted with chloroform, and an aqueous layer was separated. An organic layer was extracted with a 2N sodium hydroxide aqueous solution and the extract was washed with chloroform. An aqueous layer was acidified to a pH of 3 with 5% hydrochloric acid, and extracted with chloroform. The extract was dried over anhydrous sodium sulfate and filtered, and the solvent was distilled off under reduced pressure to give 1.43 g (yield 79%) of the titled compound as a crude product.

$^1$H-NMR ppm (CDCl$_3$, TMS): δ2.24(6H,s), 1.9–2.3(1H, m), 2.6–3.4(3H,m), 4.06(1H,t J=3Hz), 6.83(1H,d, J=7 Hz),6.99(1H,d, J=7 Hz)

72-3-) Synthesis of 4-hydroxymethyl-5,8-dimethylthiochroman

A mixture containing 1.43 g (6.43 mmol) of 5,8-dimethyl-4-carboxythiochroman and 5 ml of diethyl ether was dropwise added to a solution of 0.24 g (6.43 mmol) of lithium aluminum hydride in 5 ml of diethyl ether, and the mixture was allowed to react at reflux under heat for 6 hours. Further, 0.24 g (6.43 mmol) of lithium aluminum hydride was added, and the mixture was allowed to react at reflux under heat for 2 hours. The reaction mixture was cooled to room temperature, water was gradually added, and the mixture was extracted with ethyl acetate. An organic layer was washed with a saturated sodium chloride aqueous solution, then dried over anhydrous sodium sulfate and filtered, and the solvent was distilled off to give 1.32 g (yield 99%) of the titled compound as a crude product.

$^1$H-NMR ppm (CDCl$_3$, TMS): δ1.5–2.1(2H,m), 2.21(3H, s), 2.31(3H,s), 2.4–3.5(5H,m), 3.69(1H,s), 7.79(1H,d, J=8 Hz), 7.92(1H,d, J=8 Hz)

72-4) Synthesis of 4-methoxymethyl-5,8-dimethylthiochroman

To a mixture of 1.32 g (6.33 mmol) of 4-hydroxymethyl-5,8-dimethylthiochroman with 13 ml of methanol was added 0.1 ml of concentrated sulfuric acid, and the mixture was reacted at reflux under heat for 10 hours. The reaction mixture was cooled to room temperature, poured into ice water and extracted with ethyl acetate. The extract was washed with water and with a saturated sodium chloride aqueous solution. An organic layer was dried over anhydrous sodium sulfate and filtered, and the solvent was distilled off. The residue was purified by column chromatography (silica gel; hexane/ethyl acetate=2/1)to give 0.84 g (yield 60%) of the titled compound.

$^1$H-NMR ppm (CDCl$_3$, TMS): δ1.5–2.1(2H,m), 2.21(3H, s), 2.27(3H,s), 3.0–3.8(5H,m), 3.37(3H,s), 7.75(1H,d, J=8 Hz), 7.88(1H,d, J=8 Hz)

72-5) Synthesis of 6-acetyl-4-methoxymethyl-5,8-dimethylthiochroman

To a solution of 0.84 g (3.78 mmol) of 4-methoxymethyl-5,8-dimethylthiochroman and 0.60 g (4.54 mmol) of aluminum chloride in dichloroethane was dropwise added 0.36 g (4.54 mmol) of acetyl chloride at 0° C., and the mixture was further allowed to react at 0° C. for 1 hour. The reaction mixture was poured into ice water, and extracted with ethyl acetate. The extract was washed with a saturated sodium chloride aqueous solution, and an organic layer was dried over anhydrous sodium sulfate and filtered. Then, the solvent was distilled off under reduced pressure to give 0.30 g (yield 30%) of the titled compound as a crude product.

$^1$H-NMR ppm (CDCl$_3$, TMS): δ1.5–2.1(2H,m), 2.25(3H, s), 2.44(3H,s), 2.54(3H,s), 3.1–3.9(3H,m), 3.37(3H,s), 7.33(1H,s)

72-6) Synthesis of 6-acetyl-4-methoxymethyl-5,8-dimethylthiochroman-1,1-dioxide

A mixture containing 0.30 g (1.1 mmol) of 6-acetyl-4-methoxymethyl-5,8-dimethylthiochroman, 0.39 ml of a30 wt % hydrogen peroxide aqueous solution and 0.3 ml of acetic acid was allowed to react at 60° C. for 2 hours, and further allowed to react at 80° C. for 1 hour. The reaction mixture was cooled to room temperature, and a 2 wt % sodium hydrosulfite aqueous solution was added. The mixture was extracted with ethyl acetate, and the extract was washed with a saturated sodium chloride aqueous solution. An organic layer was dried over anhydrous sodium sulfate and filtered, and the solvent was distilled off to give 0.32 g (yield 94%) of the titled compound as a crude product.

$^1$H-NMR ppm (CDCl$_3$, TMS): δ1.8–2.2(2H,m), 2.38(3H, s), 2.5793H,s), 2.64(3H,s), 3.38(3H,s), 3.3–4.0(5H,m), 7.37(1H,s)

72-2) Synthesis of 4-methoxymethyl-5,8-dimethyl-6-carboxythiochroman-1,1-dioxide To a solution of 0.32 g (1.1 mmol) of 6-acetyl-4-methoxymethyl-5,8-dimethylthiochroman-1,1-dioxide in 1 ml of dioxane was added 3.8 ml of a sodium hypochlorite aqueous solution, and the mixture was allowed to react at 0° C. for 1 hour and further allowed to react at room temperature overnight. A 20 wt % sodium sulfite aqueous solution was added to the reaction mixture, and the mixture was washed with ethyl acetate. An aqueous layer was acidified with concentrated hydrochloric acid, and extracted with ethyl acetate. The extract was washed with a saturated sodium chloride aqueous solution, and an organic layer was dried over anhydrous sodium sulfate and filtered. Then, the solvent was distilled off under reduced pressure to give 0.24 g (yield 75%) of the titled compound as a crude product.

$^1$H-NMR ppm (CDCl$_3$, TMS): δ1.8–2.2(2H,m), 2.56(3H, s),2.64(3H,s), 3.4–4.0(5H,m), 7.83(1H,s)

Preparation Example 73

4-Propanesulfonyloxy-5-methyl-6-(1-ethyl-5-propane-sulfonyloxypyrazol-4-ylcarbonyl)thiochroman-1,1-dioxide The titled compound was obtained in the same manner as in Preparation Example 61 except that the 4-hydroxy-5- methyl-6-(1-ethyl-5-hydroxypyrazol-4-ylcarbonyl) thiochroman-1,1-dioxide synthesized in Preparation Example 71 was used in place and that the molar amount of propanesulfonyl chloride was two-fold excess. The yield of product was 7%. Table 31 shows the physical property values of product.

Preparation Example 74

4-(-Methyl-N-propanesulfonylamino)-5-methyl-6-(1-ethyl-5-propanesulfonyloxypyrazol-4-ylcarbonyl) thiochroman-1,1-dioxide The titled compound was obtained in the same manner as in Preparation Example 61 except that the 4-N-methylamino-5-methyl-6-(1-ethyl-5-propanesulfonyloxypyrazol-4-ylcarbonyl)thiochroman-1,1-dioxide synthesized in Preparation Example 69 was used in place. The yield of product was 15%. Table 31 shows the physical property values of product.

Preparation Example 75

4-Ethylthio-5-methyl-6-(1,3-dimethyl-5-(4-methylphenyl-sulfonyloxy)pyrazol-4-ylcarbonyl) thiochroman-1,1-dioxide 4-Ethylthio-5-methyl-6-(1,3-dimethyl-5-hydroxypyrazol-4-ylcarbonyl)thiochroman-1,1-dioxide was obtained from the 4-ethylthio-5-methyl-6-carboxythiochroman-1,1-dioxide synthesized in Preparation Example 53 and 1,3-dimethyl-5-hydroxypyrazole in the same manner as in Preparation Example 62, and the titled compound was obtained from the above 4-ethylthio-5-methyl-6-(1,3-dimethyl-5-hydroxypyrazol-4-ylcarbonyl)thiochroman-1,1-dioxide and p-toluenesulfonyl chloride in the same manner as in Preparation Example 63. The yield of product was 54%. Table 31 shows the physical property values of product.

Preparation Example 76

4-Chloro-6-(1-ethyl-5-hydroxypyrazol-4-ylcarbonyl) thiochroman

The titled compound was obtained in the same manner as in Preparation Example 62 except that 4-chloro-6-carboxythiochroman was used in place. The yield of product was 28%. Table 31 shows the physical property values of the product.

Preparation Example 77

4-Chloro-6-(1-ethyl-5-hydroxypyrazol-4-ylcarbonyl) thiochroman-1,1-dioxide

The titled compound was obtained in the same manner as in Preparation Example 52 except that 4-chloro-6-(1-ethyl-5-hydroxypyrazol-4-ylcarbonyl)thiochroman was used in place. The yield of product was 100%. Table 31 shows the physical property values of product.

Preparation Example 78

4-Acetamido-5,8-dimethyl-6-(1-ethyl-5-hydroxypyrazol-4-ylcarbonyl)thiochroman

The titled compound was obtained in the same manner as in Preparation Example 62 except that 4-acetamido-5,8-dimethyl-6-carboxythiochroman was used in place. The yield of product was 80%. Table 31 shows the physical property values of product.

Preparation Example 79

4-Acetamido-5,8-dimethyl-6-(1-ethyl-5-hydroxypyrazol-4-ylcarbonyl)thiochroman-1,1-dioxide The titled compound was obtained in the same manner as in Preparation Example 62 except that 4-acetamido-5,8-dimethyl-6-carboxythiochroman-1,1-dioxide was used in place. The yield of product was 83%. Table 31 shows the physical property values of product.

Preparation Example 80

4-Methoxymethyl-5,8-dimethyl-6-(1-ethyl-5-hydroxypyrazol-4-ylcarbonyl)thiochroman-1,1-dioxide The titled compound was obtained in the same manner as in preparation Example 62 except that 4-methoxymethyl-5,8-dimethyl-6-carboxythiochroman-1,1-dioxide obtained in Preparation Example 72 was used in place. The yield of product was 81%. Table 31 shows the physical property values of product.

Preparation Example 81

6-(1-Ethyl-5-hydroxypyrazol-4-yl)carbonyl-3,3-bis (fluoromethyl)-5-methylthiochroman-4-one-1,1-dioxide 0.49 Gram (purity 68%, 1.0 mmol) of 3,3-bis (fluoromethyl-6-carboxy-5-methylthiochroman-4-one-1,1-dioxide was dissolved in 10 ml of 1,2-dichloroethane, and 0.15 ml (2.1 mmol) of thionyl chloride was added. The mixture was stirred under heat at 80° C. for 1.5 hours. The solvent and excess thionyl chloride were distilled off under reduced pressure, and the residue was dissolved in 2.5 ml of acetonitrile. A separately prepared solution of 0.17 g (1.5 mmol) of 1-ethyl-5-hydroxypyrazole and 0.21 ml (1.5 mmol) of triethylamine in 2.5 ml of acetonitrile was dropwise added at 0° C., and the mixture was stirred for 30 minutes. Then, the reaction mixture was allowed to warm to room temperature, and stirred for 2 hours. To the reaction mixture were added 0.21 ml (1.5 mmol) of triethylamine and 0.05 ml (0.55 mmol) of acetonecyanhydrin, and the mixture was further stirred at room temperature for 3 hours. To the reaction mixture were added water and 10 wt % sodium hydroxide, and the mixture was washed with methylene chloride. An aqueous layer was acidified with concentrated hydrochloric acid and extracted with methylene chloride. The extract was dried over anhydrous sodium sulfate, and the solvent was distilled off under reduced pressure. The resultant substance in the form of glass was dissolved in 3 ml of methylene chloride and 3 ml of water, and 0.12 g (0.87 mmol) of potassium carbonate, 0.10 ml (0.89 mmol) of propanesulfonyl chloride and a catalytic amount of benzyl-triethylammonium chloride were added. The mixture was stirred at room temperature for 3 hours. Water and 10 wt % hydrochloric acid were added, and the mixture was extracted with methylene chloride. The extract was dried over anhydrous sodium sulfate, and the solvent was distilled off under reduced pressure, and the resultant substance in the form of glass was purified by silica gel column chromatography (hexane:ethyl acetate=2:1) to give 0.12 g (yield 22%) of 6-(1-ethyl-5-hydroxypyrazol-4-yl)carbonyl-3,3-bis (fluoromethyl)-5-methylthiochroman-4-one-1,1-dioxide. Table 31 shows the physical property values thereof.

Table 30 shows pyrazole derivatives obtained in Preparation Examples 73 to 81.

TABLE 30 pyrazole derivative

| Ex. No. | structure | Comp'd. No. |
|---|---|---|
| 73 | [structure] | 48 |
| 74 | [structure] | 49 |
| 75 | [structure] | 50 |
| 76 | [structure] | 51 |
| 77 | [structure] | 52 |
| 78 | [structure] | 53 |

TABLE 30-continued pyrazole derivative

| Ex. No. | structure | Comp'd. No. |
|---|---|---|
| 79 | [structure] | 54 |
| 80 | [structure] | 55 |
| 81 | [structure] | 56 |

TABLE 31

| Comp'd. No. | $^1$H-NMR (ppm) (internal standard:TMS) | IR (cm$^{-1}$) |
|---|---|---|
| 48 | 1.15(3H, t), 1.18(3H, t), 1.51(3H, t), 1.9–2.3(4H, m), 2.3–4.2(4H, m), 2.47(3H, s), 3.6–3.8(4H, m), 4.21(2H, q), 5.47(1H, t), 7.47(1H, s), 7.52(1H, d), 7.91(1H,d) (CDCl$_3$) | 2980, 1760, 1650, 1300, 1130 |
| 49 | 1.20(6H, t), 1.51(3H, t), 1.7–2.3(4H, m), 2.38(3H, s), 2.54(3H, s), 2.6–3.2(4H, m), 3.3–3.9(4H, m), 4.22(2H, q), 5.54(1H, t), 7.35(1H, s), 7.52(1H, d), 7.98(1H, d) (CDCl$_3$) | 2950, 1740, 1650, 1130 |
| 50 | 1.34(3H, t), 2.24(3H, s), 2.46(3H, s), 2.55(3H, s), 2.3–3.1(4H, m), 3.2–3.4(1H, m), 3.65(3H, s), 4.1–4.5(2H, m), 7.2–7.6(4H, m), 7.65(1H, d), 7.85(1H, d), (CDCl$_3$) | 2950, 1740, 1300, 1140 |
| 51 | 1.45(3H, t), 2.2–3.0(2H, m), 3.2–3.5(2H, m), 4.07(2H, q), 4.8–5.0(1H, m), 7.25(1H, d), 7.72(1H, dd), 7.80(1H, s), 7.92(1H, d) (CDCl$_3$) | — |
| 52 | 1.30(3H, t), 2.3–2.7(2H, m), 3.6–3.8(2H, m), 3.95(2H, q), 4.8–5.0(1H, m), 7.8–8.2(4H, m) (DMSO-d$_6$) | — |
| 53 | 1.46(3H, t), 2.00(3H, s), 2.27(3H, s), 2.33(3H, s), 2.5–2.8(2H, m), 2.9–3.2(2H, m), 4.06(2H, q), 5.6–5.8 (1H, m), 7.21(1H, s), 7.39.(1H, s) (CDCl$_3$) | 2950, 1710, 1620 |
| 54 | 1.45(3H, t), 2.03(3H, s), 2.25(3H, s), 2.64(3H, s), 2.5–2.7(2H, m), 3.3–3.7(2H, m), 4.05(2H, q), 4.40(1H, bs), 5.2–5.5(1H, m), 7.30(1H, s), 7.60(1H, s) (CDCl$_3$) | 2950, 1640, 1295, 1120 |

TABLE 31-continued

| Comp'd. No. | $^1$H-NMR (ppm) (internal standard:TMS) | IR (cm$^{-1}$) |
|---|---|---|
| 55 | 1.46(3H, t), 1.8–2.2(2H, m), 2.35(3H, s), 2.64(3H, s), 3.3–4.0(5H, m), 3.38(3H, s), 4.08(2H, q), 7.28(1H, s), 7.35(1H, s) (CDCl$_3$) | 3000, 1750, 1640, 1310, 1120 |
| 56 | 1.19(3H, t), 1.50(3H, t), 1.9–2.4(2H, m), 2.41(3H, s), 3.6–3.9(2H, m), 3.80(2H, s), 4.22(2H, q), 4.4–5.4(4H, m), 7.43(1H, s), 7.67(1H, d), 7.97(1H, d) (CDCl$_3$) | 3000, 1720, 1670, 1340, 1120 |

Herbicide Examples (1) Preparation of Herbicide

97 Parts by weight of talc (trade name: Zeaklite) as a carrier, 1.5 parts by weight of alkylarylsulfonic acid (trade name: Neoplex, supplied by Kao-Atlas K. K.) as a surfactant and 1.5 parts by weight of a nonionic and anionic surfactant (trade name: Sorpol 800A, supplied by Toho Chemical Co., Ltd.) were uniformly pulverized and mixed to prepare a carrier for a wettable powder.

90 Parts by weight of the above carrier and 10 parts by weight of one of the compounds obtained in the above Preparation Examples (or 10 parts by weight of one of the following compounds (D), (A), (C) and (B) for Comparative Examples) were uniformly pulverized and mixed to obtain herbicides.

The compound (D) used as a comparative chemical is disclosed in International Laid-open Publication WO095/04054 and has the following structure.

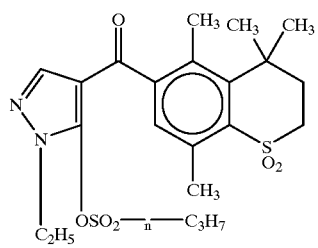
(D)

The compound (A) used as a comparative chemical is disclosed in International Laid-open Publication WO093/18031 and has the following structure.

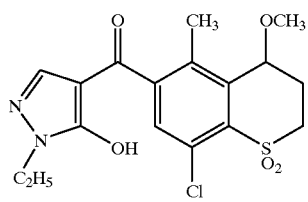
(A)

The compound (C) used as a comparative chemical is disclosed in International Laid-open Publication WO095/04054 and has the following structure.

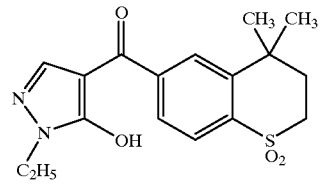
(C)

The compound (B) used as a comparative chemical is disclosed in International Laid-open Publication WO093/18031 and has the following structure.

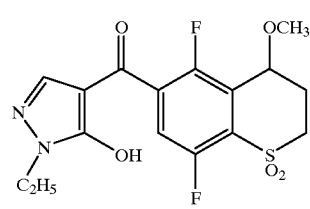
(B)

The herbicidal efficacy and phytotoxicity of each compound to crops were shown on the basis of the following ratings.

| (Ratings) | Ratio of remaining plant weight to non-treated (%) |
|---|---|
| Herbicidal efficacy | |
| 0 | 81–100 |
| 1 | 61–80 |
| 2 | 41–60 |
| 3 | 21–40 |
| 4 | 1–20 |
| 5 | 0 |
| Phytotoxicity to crops | |
| – | 100 |
| ± | 95–99 |
| + | 90–94 |
| ++ | 80–89 |
| +++ | 0–79 |

The ratio of remaining plant weight to non-treated was determined on the basis of the ratio of remaining plant weight to non-treated=(remaining plant weight in treated plot/remaining plant weight in non-treated plot)×100.

(2) Upland pre-emergence treatment test 1

Seeds of weeds such as large crabgrass, barnyardgrass, green foxtail, shattercane or black nightshade, cocklebur and velvetleaf and seeds of corn were sown in 1/5,000-are Wagner pots filled with upland soil, and covered with upland soil. Then, a predetermined amount of the herbicide prepared in the above (1) was suspended in water and uniformly sprayed onto the soil surface at a dosage of 2,000 liters/hectare. Thereafter, the plants were grown in a greenhouse, and on 20th day after the treatment, the herbicide was evaluated for herbicidal efficacy and phytotoxicity to the crop. Table 32 shows the results.

TABLE 32

(pre-emergence treatment)

| comp'd No. used | dosage (ga.i./ hectare) | herbicide efficacy | | | | | | | pytoto-xicity corn |
|---|---|---|---|---|---|---|---|---|---|
| | | (a) | (b) | (c) | (d) | (e) | (f) | (g) | |
| 1 | 300 | 5 | 5 | 4 | 4 | n.d. | 5 | 5 | — |
| 2 | 300 | 5 | 4 | 5 | 4 | n.d. | 5 | 5 | — |
| 38 | 300 | 3 | 3 | 3 | n.d. | 5 | 2 | 4 | — |
| 39 | 300 | 4 | 3 | 3 | n.d. | 4 | 2 | 4 | — |
| 41 | 300 | 3 | 3 | 3 | n.d. | 5 | 2 | 4 | — |
| 46 | 300 | 5 | 5 | 5 | n.d. | 5 | 5 | 5 | — |
| 47 | 300 | 5 | 5 | 5 | n.d. | 5 | 5 | 5 | — |
| (D) | 300 | 2 | 2 | 1 | 1 | n.d. | 5 | 5 | — |
| (A) | 300 | 0 | 0 | 0 | n.d. | 4 | 1 | 2 | — | a.i. = active ingredient
n.d. = not detected
(a): large crabgrass
(b): barnyardgrass
(c): green foxtail
(d): shattercane
(e): black nightshade
(f): cocklebur
(g): velvetleaf Table 32 shows the following: In pre-emergence treatment, the comparative herbicides have no efficacy on grass weeds, whereas all the herbicides according to the present invention exhibit an excellent efficacy not only on the broad-leaved weeds but also on the grass weeds. Further, all the herbicides according to the present invention exhibit excellent selectivity for corn.

(3) Post-emergence treatment test

Seeds of weeds such as large crabgrass, barnyardgrass, green foxtail, shattercane or black nightshade, cocklebur and velvetleaf and seeds of corn were sown in 1/5,000-are Wagner pots filled with upland soil, and covered with upland soil. The seeds were grown in a greenhouse, and at the stage of 3–4 leaves of these plants, a predetermeind amount of the herbicide prepared in the above (1) was suspended in water and uniformly sprayed onto leaf and stalk portions at a dosage of 2,000 liters/hectare. Thereafter, the plants were grown in the greenhouse, and on 30th day after the treatment, the herbicide was evaluated for herbicidal efficacy. Table 33 shows the results.

TABLE 33

(post-emergence treatment)

| comp'd No. used | dosage (g$^{a.i.}$/ hectare) | herbicide efficacy | | | | | | | pytoto-xicity corn |
|---|---|---|---|---|---|---|---|---|---|
| | | (a) | (b) | (c) | (d) | (e) | (f) | (g) | |
| 1 | 300 | 4 | 5 | 5 | 4 | — | 5 | 5 | — |
| 2 | 300 | 4 | 5 | 5 | 4 | — | 5 | 5 | — |
| 38 | 300 | 5 | 3 | 4 | — | 3 | 4 | 2 | — |
| 39 | 300 | 2 | 2 | 2 | — | 3 | 4 | 3 | — |
| 40 | 300 | 2 | 2 | 2 | — | 5 | 5 | 5 | — |
| 41 | 300 | 5 | 5 | 5 | — | 5 | 5 | 5 | — |
| 43 | 300 | 3 | 2 | 2 | — | 5 | 5 | 2 | — |
| 46 | 300 | 3 | 4 | 4 | — | 5 | 5 | 5 | — |
| 71 | 300 | 3 | 3 | 4 | — | 5 | 5 | 5 | — |
| (D) | 300 | 2 | 2 | 2 | 1 | — | 5 | 5 | — |
| (A) | 300 | 0 | 0 | 0 | — | 3 | 2 | 1 | — | a.i. = active ingredient
n.d. = not detected
(a): large crabgrass
(b): barnyardgrass
(c): green foxtail
(d): shattercane
(e): black nightshade
(f): cocklebur
(g): velvetleaf Table 33 shows the following: In post-emergence treatment, the comparative herbicides have no efficacy on grass weeds, whereas all the herbicides according to the present invention exhibit an excellent efficacy not only on the broad-leaved weeds but also on the grass weeds. Further, all the herbicides according to the present invention exhibit excellent selectivity for corn.

(4) Upland pre-emergence treatment test 2

Seeds of weeds such as large crabgrass, barnyardgrass, green foxtail, cocklebur and velveleaft and seeds of corn were sown in 1/5,000-are Wagner pots filled with upland soil, and covered with upland soil. Then, a predetermined amount of the herbicide prepared in the above (1) was suspended in water and uniformly sprayed onto the soil surface at a dosage of 2,000 liters/hectare. Thereafter, the plants were grown in a greenhouse, and on 20th day after the treatment, the herbicide was evaluated for herbicidal efficacy and phytotoxicity to the crop. Table 34 shows the results.

TABLE 34

(pre-emergence treatment)

| comp'd No. used | dosage (g$^{a.i.}$/ hectare) | herbicide efficacy | | | | | phytoto-xicity corn |
|---|---|---|---|---|---|---|---|
| | | (a) | (b) | (c) | (d) | (e) | |
| 6 | 300 | 5 | 3 | 5 | 5 | 5 | — |
| 8 | 300 | 5 | 5 | 5 | 5 | 5 | — |
| 13 | 300 | 5 | 5 | 4 | 5 | 5 | — |
| 14 | 300 | 4 | 4 | 4 | 3 | 3 | — |
| 18 | 300 | 4 | 5 | 4 | 4 | 5 | — |
| 21 | 300 | 5 | 5 | 5 | 4 | 5 | — |
| 22 | 300 | 5 | 3 | 3 | 5 | 4 | — |
| 23 | 300 | 5 | 3 | 3 | 3 | 5 | — |
| 24 | 300 | 5 | 5 | 5 | 4 | 5 | — |
| 25 | 300 | 5 | 5 | 5 | 4 | 5 | — |
| 26 | 300 | 5 | 5 | 5 | 5 | 5 | — |
| 27 | 300 | 3 | 3 | 3 | 3 | 3 | — |
| 29 | 300 | 5 | 3 | 3 | 5 | 5 | — |
| 30 | 300 | 3 | 4 | 4 | 3 | 3 | — |
| 31 | 300 | 5 | 5 | 5 | 5 | 5 | — |
| 32 | 300 | 5 | 5 | 5 | 5 | 5 | — |
| 33 | 300 | 5 | 5 | 5 | 4 | 5 | — |
| 34 | 300 | 3 | 3 | 4 | 4 | 3 | — |
| 35 | 300 | 5 | 5 | 5 | 5 | 5 | — |
| (C) | 300 | 1 | 0 | 0 | 0 | 0 | — | a.i. = active ingredient
(a): large crabgrass
(b): barnyardgrass
(c): green foxtail
(d): cocklebur
(e): velvetleaf Table 34 shows the following. In upland pre-emergence treatment, the comparative herbicide has a very low herbicidal efficacy, while all the herbicides according to the present invention can selectively control a broad range of grass and broad-leaved weeds at a low dosage. Further, all the herbicides according to the present invention have excellent selectivity for corn.

(5) Post-emergence treatment test 2

Seeds of weeds such as large crabgrass, barnyardgrass, green foxtail, cocklebur and velvetleaf and seeds of corn were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a dosage of 2,000 liters/ hectare. Thereafter, the plants were grown in the greenhouse, and on 30th day after the treatment, the herbicide was evaluated for herbicidal efficacy. Table 35 shows the results.

TABLE 35

(post-emergence treatment)

| comp'd No. used | dosage ($g^{a.i.}$/ hectare) | herbicide efficacy | | | | | phytotoxicity corn |
|---|---|---|---|---|---|---|---|
| | | (a) | (b) | (c) | (d) | (e) | |
| 6 | 300 | 5 | 3 | 5 | 5 | 5 | — |
| 14 | 300 | 4 | 4 | 4 | 3 | 3 | — |
| 18 | 300 | 3 | 4 | 4 | 5 | 4 | — |
| 21 | 300 | 5 | 5 | 4 | 5 | 5 | — |
| 22 | 300 | 5 | 3 | 3 | 5 | 4 | — |
| 23 | 300 | 5 | 4 | 5 | 5 | 5 | — |
| 24 | 300 | 5 | 5 | 4 | 5 | 5 | — |
| 25 | 300 | 3 | 3 | 3 | 4 | 5 | — |
| 26 | 300 | 3 | 4 | 5 | 5 | 4 | — |
| 30 | 300 | 3 | 4 | 4 | 3 | 3 | — |
| 31 | 300 | 3 | 3 | 3 | 4 | 5 | — |
| 32 | 300 | 3 | 4 | 3 | 3 | 5 | — |
| 34 | 300 | 3 | 3 | 4 | 4 | 3 | — |
| (C) | 300 | 1 | 0 | 0 | 0 | 1 | — | a.i. = active ingredient
(a): large crabgrass
(b): barnyardgrass
(c): green foxtail
(d): cocklebur
(e): velvetleaf Table 35 shows the following. In post-emergence treatment, the comparative herbicide has a very low herbicidal efficacy, while all the herbicides according to the present invention can selectively control a broad range of grass and broad-leaved weeds at a low dosage. Further, all the herbicides according to the present invention have excellent selectivity for corn.

(6) Upland pre-emergence treatment test 3

Seeds of weeds such as large crabgrass, barnyardgrass, green foxtail, black nightshade, cocklebur and velvetleaf and seeds of corn were sown in 1/5,000-are Wagner pots filled with upland soil, and covered with upland soil. Then, a predetermined amount of the herbicide prepared in the above (1) was suspended in water and uniformly sprayed onto the soil surface at a dosage of 2,000 liters/hectare. Thereafter, the plants were grown in a greenhouse, and on 20th day after the treatment, the herbicide was evaluated for herbicidal efficacy and phytotoxicity to the crop. Table 36 shows the results.

TABLE 36

(pre-emergence treatment)

| comp'd No. used | dosage ($g^{a.i.}$/ hectare) | herbicide efficacy | | | | | | phytotoxicity corn |
|---|---|---|---|---|---|---|---|---|
| | | (a) | (b) | (c) | (d) | (e) | (f) | |
| 55 | 300 | 5 | 5 | 5 | 5 | 5 | 5 | — |
| (B) | 300 | 0 | 1 | 0 | 1 | 1 | 1 | — | a.i. = active ingredient
(a): large crabgrass
(b): barnyardgrass
(c): green foxtail
(d): black nightshade
(e): cocklebur
(f): velvetleaf Table 36 shows the following. In upland pre-emergence treatment, the comparative herbicide has a very low herbicidal efficacy, while the herbicide containing Compound No. 55 according to the present invention exhibits a herbicidal efficacy on a broad range of upland weeds. In particular, Compound No. 55 has an excellent herbicidal efficacy on grass weeds. Further, the herbicide according to the present invention has excellent selectivity for corn.

(7) Post-emergence treatment test 3

Seeds of weeds such as large crabgrass, barnyardgrass, green foxtail, black nightshade, cocklebur and velvetleaf and seeds of corn were sown in 1/5,000-are Wagner pots filled with upland soil, and covered with upland soil. The seeds were grown in a greenhouse, and at the stage of 3~4 leaves of these plants, a predetermined amount of the herbicide prepared in the above (1) was suspended in water and uniformly sprayed onto leaf and stalk portions at a dosage of 2,000 liters/hectare. Thereafter, the plants were grown in the greenhouse, and on 30th day after the treatment, the herbicide was evaluated for herbicidal efficacy. Table 37 shows the results.

TABLE 37

(post-emergence treatment)

| comp'd No. used | dosage ($g^{a.i.}$/ hectare) | herbicide efficacy | | | | | | phytotoxicity corn |
|---|---|---|---|---|---|---|---|---|
| | | (a) | (b) | (c) | (d) | (e) | (f) | |
| 50 | 300 | 3 | 3 | 3 | 5 | 5 | 5 | — |
| 55 | 300 | 3 | 3 | 5 | 3 | 5 | 4 | — |
| (B) | 300 | 1 | 0 | 0 | 0 | 0 | 2 | — | a.i. = active ingredient
(a): large crabgrass
(b): barnyardgrass
(c): green foxtail
(d): black nightshade
(e): cocklebur
(f): velvetleaf Table 37 shows the following. In post-emergence treatment, the comparative herbicide has a very low herbicidal efficacy, while all the herbicides according to the present invention can selectively control a broad range of grass and broad-leaved weeds at a low dosage. Further, all the herbicides according to the present invention have excellent selectivity for corn.

Utility in Industry

The pyrazole derivatives of the present invention are very useful as active ingredients for herbicides for controlling upland field weeds since they cause no phytotoxicity on upland field crops such as corn, etc., and can selectively control a broad range of upland weeds such as grass weeds and broad-leaved weeds at a low dosage in pre-emergence treatment and in post-emergence treatment. The aromatic carboxylic acid derivatives of the present invention are suitable as intermediates for producing the above pyrazole derivatives.

We claim:

1. A pyrazole derivative of formula (I), or salt thereof,

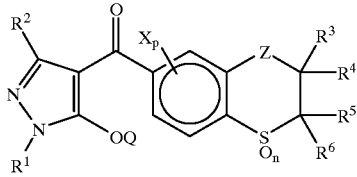
(I)

wherein $R^1$ is a $C_1$–$C_4$ alkyl group, a $C_2$–$C_4$ alkenyl group or a $C_2$–$C_4$ haloalkenyl group, $R^2$ is a hydrogen atom, a $C_1$–$C_4$ alkyl group, a $C_1$–$C_4$ haloalkyl group or a $C_2$–$C_4$ alkoxyalkyl group, X is a $C_1$–$C_4$ alkyl group, a $C_1$–$C_4$ haloalkyl group, $C_2$–$C_4$ alkoxyalkyl group, a halogen atom, a $C_1$–$C_4$ alkoxy group or a $C_1$–$C_4$ haloalkoxy group, p is 0 or an integer of 1 or 2, each of $R^3$, $R^4$, $R^5$ and $R^6$ is independently a hydrogen atom, a $C_1$–$C_4$ alkyl group, a $C_1$–$C_4$ haloalkyl group, a $C_2$–$C_4$ alkoxyalkyl group or a halogen atom, or $R^3$ or $R^4$ may form a bond with $R^5$ or $R^6$, n is 0 or an integer of 1 or 2, Q is a hydrogen atom or a group -A-B in which A is

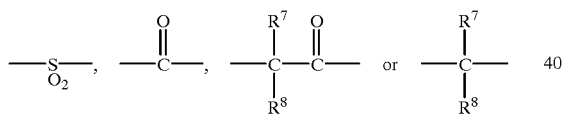

in which each of $R^7$ and $R^8$ is independently a hydrogen atom or a $C_1$–$C_4$ alkyl group, and B is a $C_1$–$C_{12}$ alkyl group, a $C_3$–$C_{10}$ cycloalkyl group or

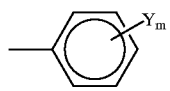

in which Y is a $C_1$–$C_4$ alkyl group, a $C_1$–$C_4$ alkoxy group, a $C_1$–$C_4$ haloalkyl group, a nitro group or a halogen atom, and m is 0 or an integer of 1 to 3, and Z is a group of the following (b),

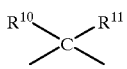
(b)

in which $R^{10}$ in the formula (b) is a halogen atom, a $C_2$–$C_6$ alkoxyalkyl group or any group of the following formula, in which each of $R^{14}$ and $R^{15}$ is independently a hydrogen atom, an oxygen atom or a $C_1$–$C_4$ alkyl group, $R^{16}$ is a hydrogen atom or a $C_1$–$C_4$ alkyl group, each of $R^{17}$ and $R^{18}$ is

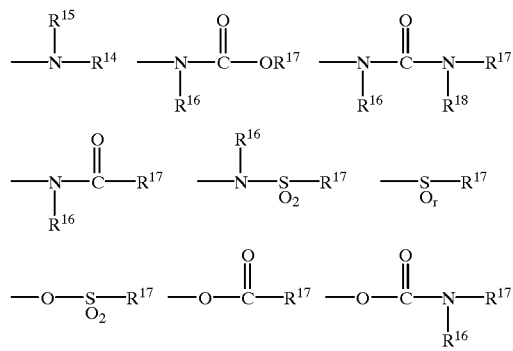

independently a $C_1$–$C_4$ alkyl group or a $C_1$–$C_4$ haloalkyl group, and r is an integer of 1 or 2, $R^{11}$ is a hydrogen atom, a $C_1$–$C_4$ alkyl group, a $C_1$–$C_4$ alkoxy group or a $C_1$–$C_4$ alkylthio group, or $R^{11}$ may form a bond with $R^3$.

2. The pyrazole derivative of claim 1, wherein the pyrazole derivative has formula (I-1) or salt thereof,

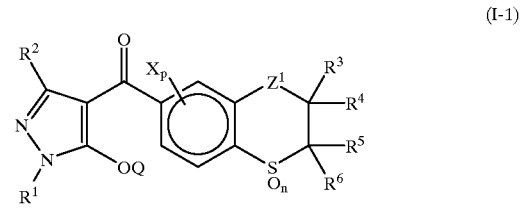
(I-1)

wherein $R^1$ is a $C_1$–$C_4$ alkyl group, a $C_2$–$C_4$ alkenyl group or a $C_2$–$C_4$ haloalkenyl group, $R^2$ is a hydrogen atom, a $C_1$–$C_4$ alkyl group, a $C_1$–$C_4$ haloalkyl group or a $C_2$–$C_4$ alkoxyalkyl group, X is a $C_1$–$C_4$ alkyl group, a $C_1$–$C_4$ haloalkyl group, $C_2$–$C_4$ alkoxyalkyl group, a halogen atom, a $C_1$–$C_4$ alkoxy group or a $C_1$–$C_4$ haloalkoxy group, p is 0 or an integer of 1 or 2, each of $R^3$, $R^4$, $R^5$ and $R^6$ is independently a hydrogen atom, a $C_1$–$C_4$ alkyl group, a $C_1$–$C_4$ haloalkyl group, a $C_2$–$C_4$ alkoxyalkyl group or a halogen atom, or $R^3$ or $R^4$ may form a bond with $R^5$ or $R^6$, n is 0 or an integer of 1 or 2, Q is a hydrogen atom or a group -A-B in which A is

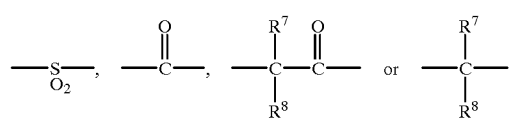

in which each of $R^7$ and $R^8$ is independently a hydrogen atom or a $C_1$–$C_4$ alkyl group, and B is a $C_1$–$C_{12}$ alkyl group, a $C_3$–$C_{10}$ cycloalkyl group or

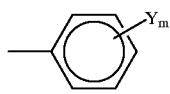

in which Y is a $C_1$–$C_4$ alkyl group, a $C_1$–$C_4$ alkoxy group, a $C_1$–$C_4$ haloalkyl group, a nitro group or a halogen atom, and m is 0 or an integer of 1 to 3, and $Z^1$ is a group of the following (b-1),

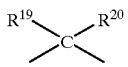

(b-1)

in which R-hu 19in the formula (b-1) is a halogen atom or any group of the following formula,

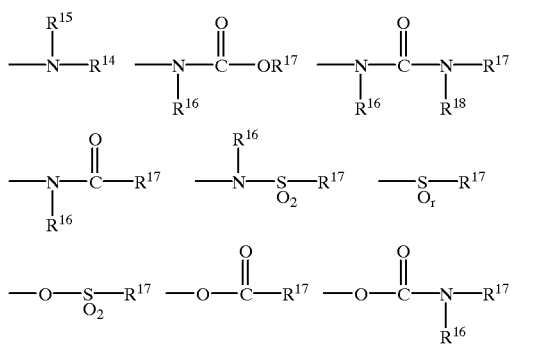

in which each of $R^{14}$ and $R^{15}$ is independently a hydrogen atom, an oxygen atom or a $C_1$–$C_4$ alkyl group, $R^{16}$ is a hydrogen atom or a $C_1$–$C_4$ alkyl group, each of $R^{17}$ and $R^{18}$ is independently a $C_1$–$C_4$ alkyl group or a $C_1$–$C_4$ haloalkyl group, and r is an integer of 1 or 2, $R^{20}$ is a hydrogen atom, a $C_1$–$C_4$ alkyl group, a $C_1$–$C_4$ alkoxy group or a $C_1$–$C_4$ alkylthio group, or $R^{20}$ may form a bond with $R^3$.

3. The pyrazole derivative of claim 1, wherein the pyrazole derivative has formula (I-3), or salt thereof,

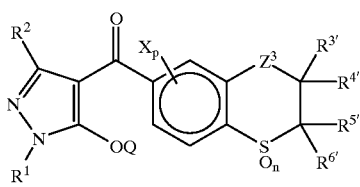

(I-3)

wherein $R^1$ is a $C_1$–$C_4$ alkyl group, a $C_2$–$C_4$ alkenyl group or a $C_2$–$C_4$ haloalkenyl group, $R^2$ is a hydrogen atom, a $C_1$–$C_4$ alkyl group, a $C_1$–$C_4$ haloalkyl group or a $C_2$–$C_4$ alkoxyalkyl group, X is a $C_1$–$C_4$ alkyl group, a $C_1$–$C_4$ haloalkyl group, $C_2$–$C_4$ alkoxyalkyl group, a halogen atom, a $C_1$–$C_4$ alkoxy group or a $C_1$–$C_4$ haloalkoxy group, p is 0 or an integer of 1 or 2, each of $R^{3'}$, $R^{4'}$, $R^{5'}$ and $R^{6'}$ is independently a hydrogen atom, a $C_1$–$C_4$ alkyl group, a $C_1$–$C_4$ haloalkyl group, a $C_2$–$C_4$ alkoxyalkyl group or a halogen atom, n is 0 or an integer of 1 or 2, Q is a hydrogen atom or a group -A-B in which A is

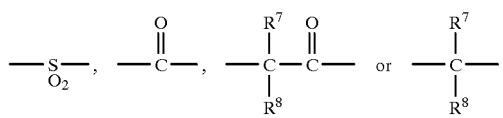

in which each of $R^7$ and $R^8$ is independently a hydrogen atom or a $C_1$–$C_4$ alkyl group, and B is a $C_1$–$C_{12}$ alkyl group, a $C_3$–$C_{10}$ cycloalkyl group or

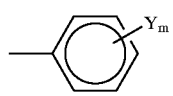

in which Y is a $C_1$–$C_4$ alkyl group, a $C_1$–$C_4$ alkoxy group, a $C_1$–$C_4$ haloalkyl group, a nitro group or a halogen atom, and m is 0 or an integer of 1 to 3, and $Z^3$ is a group of

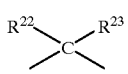

in which $R^{22}$ is a halogen atom, a $C_1$–$C_4$ alkylthio group, a $C_2$–$C_6$ alkoxyalkyl group or any group of the following formulae,

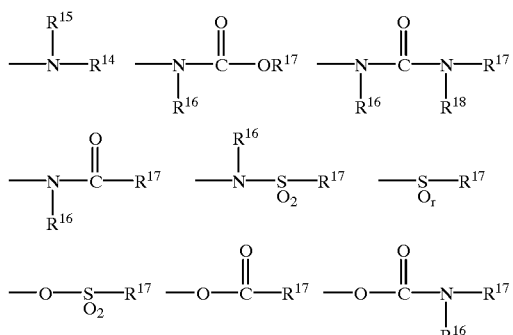

in which each of $R^{14}$ and $R^{15}$ is independently a hydrogen atom, an oxygen atom or a $C_1$–$C_4$ alkyl group, $R^{16}$ is a hydrogen atom or a $C_1$–$C_4$ alkyl group, each of $R^{17}$ and $R^{18}$ is independently a $C_1$–$C_4$ alkyl group or a $C_1$–$C_4$ haloalkyl group, and r is an integer of 1 or 2, $R^{23}$ is a hydrogen atom or a $C_1$–$C_4$ alkyl group, or $R^{23}$ may form a bond with $R^{3'}$.

4. The pyrazole derivative or salt of claim 1, wherein $R^1$ is methyl or ethyl.

5. The pyrazole derivative or salt of claim 1, wherein $R^2$ is hydrogen or methyl.

6. The pyrazole derivative or salt of claim 1, wherein each of $R^3$, $R^4$, $R^5$ and $R^6$ is independently a hydrogen atom, a chlorine atom or methyl.

7. The pyrazole derivative or salt of claim 1, wherein X is methyl or a chlorine atom.

8. The pyrazole derivative or salt of claim 1, wherein X is methoxy.

9. The pyrazole derivative or salt of claim 1, wherein a substituent X is substituted on the 5-position on the thiochroman ring, or substituents X are substituted on the 5- and 8-positions on the thiochroman ring.

10. The pyrazole derivative or salt of claim 1, wherein n is 0 or 2.

11. The pyrazole derivative or salt of claim 1, wherein Q is a hydrogen atom.

12. The pyrazole derivative or salt of claim 1, wherein Q is the group of -A-B in which A is —$SO_2$—.

13. The pyrazole derivative or salt of claim 1, wherein Q is the group of -A-B in which B is ethyl or n-propyl.

14. The pyrazole derivative or salt of claim 1, wherein B is a group of

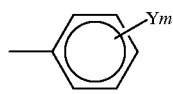

in which Y is methyl and m is 1.

15. The pyrazole derivative or salt of claim 5, wherein $Z^2$ is a group of

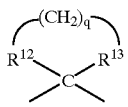

in which q is 2 and $R^{12}$ is oxygen or sulfur.

16. The pyrazole derivative or salt of claim 5, wherein $Z^2$ is carbonyl.

17. The pyrazole derivative or salt of claim 6, wherein $Z^4$ is a group of

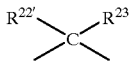

in which $R^{22}$ is chlorine, ethylthio, methylamino, N-methylcarbamoyloxy or N-methyl-N-methoxycarbonylamino.

18. A herbicide containing, as an active ingredient, at least one compound selected from the pyrazole derivative of claim 1, or salts thereof, as recited in claim 1.

19. A carboxylic acid derivative of formula (II) or salt thereof,

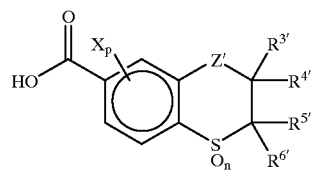 (II)

wherein:
X is a $C_1$–$C_4$ alkyl group, a $C_1$–$C_4$ haloalkyl group, a $C_2$–$C_4$ alkoxyalkyl group, a halogen atom, a $C_1$–$C_4$ haloalkoxy group,
p is 0 or an interger of 1 or 2,
each of $R^3$, $R^4$, $R^5$ and $R^6$ is independently a hydrogen atom, a $C_1$–$C_4$ alkyl group, $C_1$–$C_4$ haloalkyl group, a $C_2$–$C_4$ alkoxyalkyl group or a halogen atom, or $R^3$ or $R^4$ may form a bond with $R^5$ or $R^6$,
n is 0 or an interger of 1 or 2, and
Z' is a group of the following (b'):

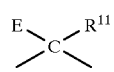 (b')

in which $R^{11}$ in the formula (b') is a hydrogen atom, a $C_1$–$C_4$ alkyl group, a $C_1$–$C_4$ alkoxy group or a $C_1$–$C_4$ alkylthio group, or $R^{11}$ may form a bond with $R^3$,
E is a hydroxyl group, a halogen atom, a $C_2$–$C_6$ alkoxyalkyl group or any group of the following formula,

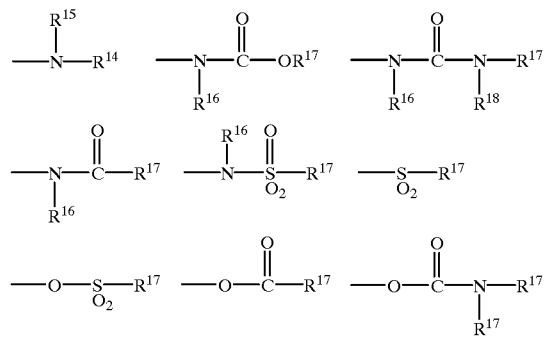

in which each of $R^{14}$ and $R^{15}$ is independently a hydrogen atom, an oxygen atom or a $C_1$–$C_4$ alkyl group, $R^{16}$ is a hydrogen atom or a $C_1$–$C_4$ alkyl group, each of $R^{17}$ and $R^{18}$ is independently a $C_1$–$C_4$ alkyl group or a $C_1$–$C_4$ haloalkyl group, and r is an integer of 1 or 2,
provided that when $R^{11}$ and $R^3$ do not form a bond, E may form a bond with $R^3$.

* * * * *